US011613736B2

(12) United States Patent
Ameri et al.

(10) Patent No.: US 11,613,736 B2
(45) Date of Patent: Mar. 28, 2023

(54) ISOLATION OF BONA FIDE PANCREATIC PROGENITOR CELLS

(71) Applicant: University of Copenhagen, Copenhagen K (DK)

(72) Inventors: Jacqueline Ameri, Genarp (SE); Henrik Semb, Bjärred (SE)

(73) Assignee: University of Copenhagen, Copenhagen K (DK)

( * ) Notice: Subject to any disclaimer, the term of this patent is extended or adjusted under 35 U.S.C. 154(b) by 568 days.

(21) Appl. No.: 16/653,245

(22) Filed: Oct. 15, 2019

(65) Prior Publication Data
US 2020/0080062 A1 Mar. 12, 2020

Related U.S. Application Data

(62) Division of application No. 15/568,978, filed as application No. PCT/EP2016/058920 on Apr. 21, 2016, now Pat. No. 10,494,608.

(30) Foreign Application Priority Data

Apr. 24, 2015 (EP) ..................................... 15164999

(51) Int. Cl.
C12N 5/071 (2010.01)
C12N 5/00 (2006.01)
A61P 3/08 (2006.01)
C07K 16/28 (2006.01)
G01N 33/566 (2006.01)

(52) U.S. Cl.
CPC ............. *C12N 5/0678* (2013.01); *A61P 3/08* (2018.01); *C07K 16/2863* (2013.01); *C12N 5/0081* (2013.01); *C12N 5/0676* (2013.01); *G01N 33/566* (2013.01); *C12N 2501/50* (2013.01); *C12N 2501/58* (2013.01); *C12N 2501/585* (2013.01); *C12N 2506/02* (2013.01)

(58) Field of Classification Search
CPC ............................ C12N 5/0678; C12N 5/0676
See application file for complete search history.

(56) References Cited

U.S. PATENT DOCUMENTS

| | | | |
|---|---|---|---|
| 7,510,876 | B2 | 3/2009 | D'Amour et al. |
| 7,534,608 | B2 | 5/2009 | Martinson et al. |
| 7,695,965 | B2 | 4/2010 | Martinson et al. |
| 7,993,920 | B2 | 8/2011 | Martinson et al. |
| 8,129,182 | B2 | 3/2012 | D'Amour et al. |
| 8,278,106 | B2 | 10/2012 | Martinson et al. |
| 8,338,170 | B2 | 12/2012 | Kelly et al. |
| 8,425,928 | B2 | 4/2013 | Martinson et al. |
| 8,551,779 | B2 | 10/2013 | Hald et al. |
| 8,603,811 | B2 | 12/2013 | D'Amour et al. |
| 8,633,024 | B2 | 1/2014 | D'Amour et al. |
| 8,647,873 | B2 | 2/2014 | D'Amour et al. |
| 8,741,643 | B2 | 6/2014 | Rezania et al. |
| 8,927,274 | B2 | 1/2015 | Itskovitz-Eldor et al. |
| 9,045,736 | B2 | 6/2015 | Kelly et al. |
| 9,096,832 | B2 | 8/2015 | Xu |
| 9,175,260 | B2 | 11/2015 | Dalton et al. |
| 9,506,034 | B2 | 11/2016 | Kelly et al. |
| 9,585,917 | B2 | 3/2017 | Martinson et al. |
| 9,725,699 | B2 | 8/2017 | Rezania et al. |
| 9,744,195 | B2 | 8/2017 | Xu |
| 9,764,062 | B2 | 9/2017 | Martinson et al. |
| 9,913,930 | B2 | 3/2018 | Martinson et al. |
| 9,980,986 | B2 | 5/2018 | Martinson et al. |
| 10,000,739 | B2 | 6/2018 | Kume et al. |
| 10,266,808 | B2 | 4/2019 | Kelly et al. |
| 10,272,179 | B2 | 4/2019 | Martinson et al. |
| 10,370,645 | B2 | 8/2019 | D'Amour et al. |
| 10,456,424 | B2 | 10/2019 | Xu |
| 10,517,901 | B2 | 12/2019 | Martinson |
| 2005/0196784 | A1 | 9/2005 | Reynisdottir et al. |
| 2009/0263896 | A1 | 10/2009 | Kelly et al. |
| 2009/0280096 | A1 | 11/2009 | Kubo et al. |
| 2009/0311782 | A1 | 12/2009 | Chiou et al. |
| 2010/0255580 | A1 | 10/2010 | Rezania |
| 2013/0309769 | A1 | 11/2013 | Benvenisty |
| 2014/0030234 | A1 | 1/2014 | Kim et al. |
| 2014/0329704 | A1 | 11/2014 | Melton et al. |
| 2015/0018235 | A1 | 1/2015 | Chapman et al. |
| 2015/0104430 | A1 | 4/2015 | Keller et al. |
| 2016/0355787 | A1 | 12/2016 | D'Amour et al. |
| 2017/0044498 | A1 | 2/2017 | Kelly et al. |
| 2018/0127724 | A1 | 5/2018 | Ameri et al. |
| 2018/0179593 | A1 | 6/2018 | Melton et al. |
| 2019/0128885 | A1 | 5/2019 | Nostro et al. |
| 2019/0201582 | A1 | 7/2019 | Martinson et al. |

(Continued)

FOREIGN PATENT DOCUMENTS

EP 1743663 1/2007
EP 2 562 248 A1 2/2013

(Continued)

OTHER PUBLICATIONS

Gao, L., et al., "Post-Passage rock inhibition induces cytoskeletal aberrations and apoptosis in Human embryonic stem cells", Stem Cell Research 41 (2019) 101641, 8 pages.
Ku, H.T., "Minireview: Pancreatic Progenitor Cells-Recent Studies" Endocrinology 149(9): 4312-4316 (2008).
Noguchi, H., "Pancreatic Stem/Progenitor Cells for the Treatment of Diabetes", The Review of Diabetic Studies, 7(2): 105-111 (2010).
Pederson, J.K., et al., "Endodermal expression of Nkx6 genes depends differentially on Pdx1", Developmental Biology, 288 (2005) 487-501.
Zhou, Q., et al., "A Multipotent Progenitor Domain Guides Pancreatic Organogenesis", Development Cell 13, 103-114 (2007).

(Continued)

*Primary Examiner* — Daniel C Gamett
(74) *Attorney, Agent, or Firm* — Julie K. Staple; Dinsmore & Shohl LLP

(57) ABSTRACT

The present invention relates to a method for isolating bona fide pancreatic progenitor cells and to cell populations enriched for bona fide pancreatic progenitor cells.

18 Claims, 42 Drawing Sheets

(56) References Cited

U.S. PATENT DOCUMENTS

| | | |
|---|---|---|
| 2019/0390169 A1 | 12/2019 | Osafune et al. |
| 2020/0030383 A1 | 1/2020 | Xu |
| 2020/0048614 A1 | 2/2020 | Rezania et al. |

FOREIGN PATENT DOCUMENTS

| | | |
|---|---|---|
| EP | 2610336 | 7/2013 |
| EP | 2 644 694 A1 | 10/2013 |
| EP | 2650360 | 10/2013 |
| EP | 2185695 | 2/2015 |
| EP | 3 3 63 444 A1 | 8/2018 |
| EP | 3 527 658 A1 | 2/2019 |
| EP | 2 356 213 B1 | 5/2019 |
| EP | 2 650 359 A1 | 10/2019 |
| EP | 3 591 040 A1 | 1/2020 |
| EP | 3 594 323 A1 | 1/2020 |
| WO | WO 03/055992 | 7/2003 |
| WO | 2003087349 A1 | 10/2003 |
| WO | WO 2004/010933 | 2/2004 |
| WO | WO 2005/045001 A2 | 5/2005 |
| WO | WO 2005/063971 | 7/2005 |
| WO | WO 2005/116073 | 12/2005 |
| WO | WO 2006/083782 | 8/2006 |
| WO | WO 2006/094286 | 9/2006 |
| WO | WO 2007/042225 | 4/2007 |
| WO | WO 2007/103282 | 9/2007 |
| WO | WO 2007/127927 | 11/2007 |
| WO | WO 2007/130474 | 11/2007 |
| WO | WO 2008/094597 | 8/2008 |
| WO | WO 2009/012428 | 1/2009 |
| WO | WO 2009/018453 | 2/2009 |
| WO | WO 2009/083502 | 7/2009 |
| WO | WO 2009/121958 | 10/2009 |
| WO | WO 2009/126927 | 10/2009 |
| WO | WO 2009/131568 | 10/2009 |
| WO | WO 2009/132063 | 10/2009 |
| WO | WO 2009/132063 A2 | 10/2009 |
| WO | WO 2010/053472 | 5/2010 |
| WO | WO 2010/057039 | 5/2010 |
| WO | WO 2011/128897 | 10/2011 |
| WO | WO 2012/056997 A1 | 5/2012 |
| WO | WO 2012/070014 | 5/2012 |
| WO | WO 2013086008 | 6/2013 |
| WO | WO 2013/163739 | 11/2013 |
| WO | WO 2013/188138 | 12/2013 |
| WO | WO 2014/024183 | 2/2014 |
| WO | WO 2014/127219 | 8/2014 |
| WO | WO 2014/160413 | 10/2014 |
| WO | WO 2014/201167 | 12/2014 |
| WO | WO 2015/173576 | 11/2015 |
| WO | WO 2015/173578 | 11/2015 |
| WO | WO 2016/138464 | 9/2016 |
| WO | WO 2018/159805 A1 | 9/2018 |
| WO | WO 2018/229179 A1 | 12/2018 |

OTHER PUBLICATIONS

Ameri, J. et al. (2010) Stem Cells 28(1):45-ii6, FGF2 Specifies hESC-Derived Definitive Endoderm into Foregut/Midgut Cell Lineages in a Concentration-Dependent Manner.

Ameri, J., et al., "Efficient Generation of Glucose-Responsive Beta Cells from Isolated GP2+ Human Pancreatic Progenitors", Cell Reports 19, 36-49, Apr. 4, 2017.

Aoi, T. et al. (2008) Nihon Rinsho. 66(5): 850-6, [Advance m study of induced pluripotent stem cells (iPS cells)].

Attali, M., et al., "Control of Beta-Cell Differentiation by the Pancreatic Mesenchyme", Diabetes, vol. 56, May 2007, 1248-1258.

Besson, A., et al., "CDK Inhibitors: Cell Cycle Regulators and Beyond", Developmental Cell, 14, Feb. 2008, 159-169.

Bhushan, A., et al., "Fgf10 is essential for maintaining the proliferative Capacity of Epithelial progenitor cells during early pancreatic organogenesis", Developmen 128, 5109-5117 (2001).

Bonfanti, P., et al., "Ex Vivo Expansion and Differentiation of Human and Mouse Fetal Pancreatic Progenitors Are Modulated by Epidermal Growth Factor", Stem Cells and Development, 24(15): 1766-1779 (2015).

Bruni, A., et al., "Islet cell transplantation for the treatment of type 1 diabetes: recent advances and future challenges", Diabetes, Metabolic Syndrome and Obesity: Targets and Teraphy 2014: 7, 211-223.

Castaing, M., et al., "Ex Vivo Analysis of Acinar and Endocrine Cell Development in the Human Embryonic Pancreas", Development Dynamics, 234: 339-345 (2005).

Cebola, I., et al., "TEAD and YAP regulate the enhancer network of human embryonic pancreatic progenitors", Nature Cell Biology, 17(5): 24 pages (May 2015).

Cheng, X., et al., "Self-Renewing Endodermal Progenitor Lines Generated from Human Pluripotent Stem Cells", Cell Stem Cell, Apr. 6, 2012, 10(4): 371-384.

Chung, Y. et al. (2008) Cell Stem Cell. 2(2): 113-7, Human Embryonic stem cell lines generated without embryo destruction.

Cogger, K., et al., "Glycoprotein 2 is a specific cell surface marker of human pancreatic progenitors", Nature Communications, 8: 331, 17 pages (2017).

D'Amour et al. 2006 "Production of pancreatic hormone-expressing endocrine cells from human embryonic stem cells" Nature Biotechnologl/, vol. 24, No. 11, 1392-1401.

D'Amour, K., et al., "Efficient differentiation of human embryonic stem cells to definitive endoderm", Nature Biotechnology, (2005), 8 pages.

Diep, C., et al., "Down-Regulation of Yes Associated Protein 1 Expression Reduces Cell Proliferation and Clonogenicity of Pancreatic Cancer Cells", PLoS One, 7(3): e32783, Mar. 2012.

Donovan, J., et al., "Transforming growth factor-beta and breast cancer cell cycle arrest by transforming growth factor-beta and its disruption in cancer", Breast Cancer Res. 2000, 2: 116-124.

Elghazi, L., et al., Role for FGFR1IIIb-mediated signals in controlling pancreatic endocrine progenitor cell proliferation, PNAS, Mar. 19, 2001, 99(6): 3884-3889.

Fateye, B., et al., Combination of Phosphatidylinositol 3-kinases pathway inhibitor and photodynamic therapy in endothelial and tumor cells, Photochemistry and Photobiology, 2012, 88: 1265-1272.

Fischer, Y., et al., NANOG Reporter Cell Lines Generated by Gene Targeting in Human Embryonic Stem Cells, PLoS One, Sep. 2010, 5(9): e12533, 11 pages.

Funa, N.S., et al., "Beta-Catenin Regulates Primitive Streak Induction through Collaborative Interactions with SMAD2/SMAD3 and OCT4", Cell Stem Cell, 16, 639-652, Jun. 4, 2015.

Gu, G., et al., "Direct evidence for the pancreatic lineage: NGN3+ cells are islet progenitors and are distinct from duct progenitors", Development 129, 2447-2457 (2002).

Guo, T., et al., "Factors Expressed by Murine Embryonic Pancreatic Mesenchyme Enhance Generation of Insulin-Producing Cells from hESCs", Diabetes, vol. 62 (May 2012), 1581-1592.

Haid et al., Diabetologia, Jan. 2012: 55(1): 154-165 (Year 2012).

Heins et.al. (2004) Stem Cells. 22(3):367-76. Derivation, characterization, and differentiation of human embryonic stem cells.

Herrera, P. "Defining the cell lineages of the islets of langerhans using transgenic mice", Int. J. Dev. Biol, 46: 97-103 (2002).

Hoebeeck, J., et al., "Rapid detection of VHL exon deletions using real-time quantitative PCR", Laboratory Investigation (2005) 85, 24-33.

Holland et al. (2006) Genesis 44(6):304-307, A mouse carrying the green fluorescent protein gene targeted to the Pdx1 locus facilitates the study of pancreas development and function.

Hoops, T., et al., "Isolation of the cDNA Encoding Glycoprotein-2 (GP-2), the Major Zymogen Granule Membrane Protein", The Journal of Biological Chemistry, 266(7): Mar. 5, 1991, 4257-4263.

Jennings et al.: Development of the Human Pancreas From Foregut to Endocrine Commitment, Diabetes, 62, 3514-22, 2013.

Jiang et al. 2011 "CD24: A Novel Surface Marker for PDX1-Positive Pancreatic Progenitors Derived from Human Embryonic Stem Cells" Stem Cells; 29, 609-617.

(56) References Cited

OTHER PUBLICATIONS

Jiang, J. et al. (2007), Stem Cells 25(8):1940-1953, Generation of Insulin-producing islet-like clusters from human embryonic stem cells.

Kawaguchi et al.: The role of the transcriptional regulator Ptf1 a in converting intestinal to pancreatic progenitors, Nat Genet, 32, 128-34, 2002.

Kelly, O. G. et al., (2011) Nat Biotechnol. (29'): 750-756, Cell-surface markers for the isolation of pancreatic cell types derived from human embryonic stem cells.

Kempf, H. et al. Adv. Drug Delivery Rev. (2016) 96, 18-30, Large-scale production of human pluripotent stem cell derived cardiomyocytes.

Kippin et al.: p21 loss compromises the relative quiescence of forebrain stem cell proliferation leading to exhaustion of their proliferation capacity, Genes Dev, 19, 756-67, 2005.

Koike et al.: Ring1B Promotes Hepatic Stem/Progenitor Cell Expansion Through Simultaneous Suppression of Cdkn1a and Cdkn2a in Mice, Hepatology, 60, 323-33, 2014.

Kopp et al.: Sox9+ ductal cells are multipotent progenitors throughout development but do not produce new endocrine cells in the normal or injured adult pancreas, Development, 138, 653-65, 2011.

Kroon, E. et al, (2008) Nat Biotechnol. 26(4):443-52, Pancreactic endoderm derived from human embryonic stem cells generates glucose-responsive insulin-secreting cells in vivo.

Kumar, S., et al., "Recent Developments in Beta-Cell Differentiation of Pluripotent Stem Cells Induced by Small and Large Molecules", Int. J. Mol. Sc. 2014, 15, 23418-23447.

Miyatsuka et al.: Neurogenin3 inhibits proliferation in endocrine progenitors by inducing Cdkn1a, Proc Natl Acad Sci U S A, 108, 185-90, 2010.

Nair et al.: Islet formation in mice and men: Lessons for the generation of functional insulin-producing β cells from human pluripotent stem cells, Curr Opin Genet Dev, 32, 171-80, 2015.

Naujok and Lenzen (2012) Stem Cell Rev. 8(3):779-91, A critical re-evaluation of CD24-positivity of human embryonic stem cells differentiated into pancreatic progenitors.

Naujok et al.: A Critical Re-Evaluation of CD24-Positivity of Human Embryonic Stem Cells Differentiated into Pancreatic Progenitors, Stem Cell Rev. 8(3):779-91, 2012.

Nelson et al., The transcription factors Nkx6.1 and Nkx6.2 possess equivalent activities in promoting beta-cell fate specification in Pdx1+ pancreatic progenitor cells, Development 134, 2491-2500, (2007).

Ogaki et al. 2011 "An expression profile analysis of ES ceil-derived definitive endodermal cells and Pdx1-expressing cells" BMC Developmental Biology; 11, 1-15.

Orford et al.: Deconstructing stem cell self-renewal: genetic insights into cell-cycle regulation, Nat Rev Genet, 9, 115-28, 2008.

Pagliuca et al. (2014) Cell. 159(2):428-39, Generation of functional human pancreatic beta cells in vitro.

Piccand et al.: Pak3 Promotes Cell Cycle Exit and Differentiation of b-Cells in the Embryonic Pancreas and is Necessary to Maintain Glucose Homeostasis in Adult Mice, Diabetes, 63, 203-15, 2014.

Ramond et al.: Reconstructing human pancreatic differentiation by mapping specific populations during development. eLife 2017;6:e27564, doi: 10,7554/eLife.27564.

Rezania et al. (2010) Eur J Pharmacol. 627(1-3):265-8, The effect of litium chloride an WIN 55,212-2-induced tolerance in isolated guinea pig ileum.

Rezania et al. 2013 "Enrichment of Human Embryonic Stem Cell-Derived NKX6.1-Expressing Pancreatic Progenitor Cells Accelerates the Maturation of Insulin-Secreting Cells In Vivo" Stem Cells; 31, 2432-2442.

Rezania, A. et al, (2014) Nat Biotechnol. (32): 1121-33, Reversal of diabetes with insulin-producing cells derived in vitro from human pluripotent stem cells.

Rezania, A. et al, (2012) Diabetes. Aug. 2012,61 (8):2016-2, Maturation of human embryonic stem cell-derived pancreatic progenitors into functional islets capable of treating pre-existing diabetes in mice.

Russ et al.: Controlled induction of human pancreatic progenitors produces functional beta-like cells in vitro, EMBO J, 34, 1759-72, 2015.

Schaffer et al., Nkx6.1 Controls a Gene Regulatory Network Required for Establishing and Maintaining Pancreatic Beta Cell Identity, PLoS Genetics, vol. 9, No. 1, 2013.

Schaffer et al.: Ptf1a and Nkx6 transcription factors function as antagonistic lineage determinants in multipotent pancreatic progenitors, Dev Cell, 18, 1022-9, 2010.

Schulz et al.: A Scalable System for Production of Functional Pancreatic Progenitors from Human Embryonic Stem Cells, PLoS One, 7, e37004, 2012.

Seymour et al. 2007 "SOX9 is required for maintenance of the pancreatic progenitor cell pool" PNAS, vol. 104, No. 6, 1865-1870.

Seymour, Sox9: A Master Regulator of the Pancreatic Program, The Review of Diabetic Studies, vol. 11, No. 1, 2014.

Shapiro et al. (2000) N Engl J Med 343:230-238, Islet transplantation in seven patients with type 1 diabetes mellitus using a glucocorticoid-free immunosuppressive regimen.

Shapiro et al. (2001a) Best Pract Res Clin Endocrinol Metab 15:241-264, Pancreatic islet transplantation in the tratment of diabetes mellitus.

Shapiro et al. (2001b) British Medical Journal 322:861, Could fewer islet cells be transplanted in type 1 diabetes? Insulin independence should be dominant force in islet transplantation.

Sneddon et al.: Self-renewal of embtyonic-stem-cell-derived progenitors by organ-matched mesenchyme, Nature, 491, 765-8, 2012.

Stadtfeld and Hochedlinger (2010) Genes Dev. 24(20):2239-63, Induced pluripotency: history, mechanism, and applications.

Stanger et al.: Organ size is limited by the No. of embryonic progenitor cells in the pancreas but not the liver, Nature, 445, 886-91, 2007.

Takahashi and Yamanaka (2006) Cell. Aug. 25, 2006;126(4):663-76, Induction of pluripotent stem cells from mouse embryonic and adult fibroblast cultures by defined factors.

Takahashi et al. (2007) Cell 131 (5): 861-872, Induction of pluiripotent stem cells from adult human fibroblasts by defined factors.

Takashima et al. (2014) Cell. 158(6): 1254-1269, Resetting transcription factor control circuitry toward ground-state pluripotency in human.

Taylor et al., Nkx6.1 is essential for maintaining the functional state of pancreatic beta cells, Cell Rep. Sep. 26, 2013; 4(6): 1262-1275.

Tesar et al. (2007) Nature 448(7150): 196-9, New cell lines from mouse epiblast share defining features with human embryonic stem cells.

Thomson, A. et al. (1998) Science. 6;282(5391):1145-7, Embryonic stem cell lines derived from human blastocysts.

Tumaneng K. et al, (2012) Nat. Cell. Biol. 14(12), 1322-1329, YAP mediates crosstalk between the Hippo and PI3K-TOR pathways by suppressing PTEN via miR-29.

Wernig, M. et al. (2007) Nature. 448(7151):318-24, In vitro reprogamming of fibroblasts into a pluripotent ES-cell-like state.

Xie et al.: Dynamic chromatin remodeling mediated by Polycomb proteins orchestrates pancreatic differentiation of human embryonic stem cells, Cell Stem Cell, 12, 224-37, 2013.

Ye et al.: Fibroblast growth factors 7 and 10 are expressed in the human embryonic pancreatic mesenchyme and promote the proliferation of embryonic pancreatic epithelial cells, Diabetologia, 48, 277-81, 2005.

Yoon et al.: Cell cycle regulation by the intrinsically disordered proteins p21 and p27, Biochem Soc Trans, 40, 981-8, 2012.

Yu et al., (2007) Science 318:5858 1917-1920, Induced pluripotent stem cell lines derived from human somatic cells.

Yu et al.: Absence of the Major Zymogen Granule Membrane Protein, GP2, Does Not Affect Pancreatic Morphology or Secretion, J Biol Chem, 279, 50274-9, 2004.

Yu J, et al. (2009) Science vol. 324 797-801, Human induced pluripotent stem cells free of vector and transgene sequences.

(56) References Cited

OTHER PUBLICATIONS

Zhang et al. 2013 "miR-375 Inhibits Proliferation of Mouse Pancreatic Progenitor Cells by Targeting YAPI" Cell Physiol Biochem; 32, 1808-1817.

Zhang et al.: Highly efficient differentiation of human ES cells and iPS cells into mature pancreatic insulin-producing cells, Cell Res, 19, 429-38, 2009.

Zhu et al.: Human pancreatic beta-like cells converted from fibroblasts, Nat Commun, 7, 10080, 2016.

Notice of Allowance for U.S. Appl. No. 15/568,978, "Isolation of Bona Fide Pancreatic Progenitor Cells", dated Jul. 15, 2019.

Final Office Action for U.S. Appl. No. 15/568,978, "Isolation of Bona Fide Pancreatic Progenitor Cells", dated Apr. 29, 2019.

Office Action for U.S. Appl. No. 15/568,978, "Isolation of Bona Fide Pancreatic Progenitor Cells", dated Oct. 16, 2018.

Danielsson, A., et al., "The Human Pancreas Proteome Defined by Transcriptomics and Antibody-Based Profiling", PLoS One 9(12): e115421. doi:10.1371/journal.pone.0115421, 21 pages, Dec. 29, 2014.

Roggenbuck, D. et al., Autoantibodies to GP2, the major zymogen granule membrane glycoprotein, are new markers in Crohn's disease, Clinica Chimica Acta, 412: 718-724, Dec. 31, 2010.

Yang, Y. et al., Multiparameter Screening Reveals a Role for Na+ Channels in Cytokine-Induced β-Cell Death, Mol Endocrinol, 28(3): 406-417, Mar. 2014.

Szabat, M. et al., High-content screening identifies a role for Na+ channels in insulin production, Royal Society Open Science, 2: 150306, Dec. 2015, 13 pages.

(Author unknown), Cell type atlas—MPZ—The Human Protein Atlas, 6 pages, downloaded Aug. 24, 2021 https://www.proteinatlas.org/ENSG00000158887-MPZ/celltype, 6 pages.

Pruunsild, P. et al., Structure, alternative splicing, and expression of the human and mouse KCNIP gene family, Genomics, 86: 581-593, Aug. 19, 2005.

Chen, B. et al., Identification of microRNAs expressed highly in pancreatic islet-like cell clusters differentiated from human embryonic stem cells, Cell Biology International, 35: 29-37, Aug. 25. 2010.

| | SA121 | H9 | HUES-4 |
|---|---|---|---|
| Transfected cells | 74,5 M | 42 M | 168 M |
| G418$^R$ clones | 57 | 248 | 353 |
| Targeted clones | 0 | 0 | 4 |
| Absolute targeting efficiency | 0 | 0 | 2,4E-8 |
| Relative targeting efficiency | 0% | 0% | 1,1% |

| Definitive Endoderm | | Primitive GT | PE |
|---|---|---|---|
| AA + Wnt3a | AA | RA | FGF2 +/- Nog |
| RPMI | RPMI + B27 | DMEM + B27 | DMEM + B27 |
| 1 day | 4 days | 3 days | ≥12 days |

Sub 3a: GATA2, MEIS2, TBX2, TOX2, CDH10, EDN1, EYA1, FGFR1, HEY2, HOXA2, HOXA3, HOXA4, HOXB2, ITGA3, ITGA4, NCAM2, PBX3, TGFB2, TWIST1, VIM

Sub 5: NKX6-2, SOX9, CALB1, CTNND2, CUX2, CCND1, CCND2, EGFR, GP2, MPZ, NFE2, ONECUT2, OTX2, TGFA, TTYH1, ERBB2, ZFHX2

Sub 6: ELF5, GATA4, HNF1A, SMAD9, SOX13, CDH1, F3, DLK1, EPCAM, FOLR1, FOXA2, FOXA3, HES1, HNF4G, LYZ, NR4A2, PDX1, RXRA, ZHX2

Sub 7: ELF1, ELF3, GATA6, KLF5, PRDM16, TGIF2, AGR2, AGR3, CTNND1, CXCR4, FGFR2, FGFR4, ONECUT1, RELN, STAT4, ERBB3

FIG. 3C (CONT'D)

| ChIR | AA | AA | P7 | P7+SantInhog+RA | TBP+Nog |
|---|---|---|---|---|---|
| RPMI | RPMI | RPMI +B27 | DF12+B27+ NAHCO3+VitC | DMEM High Glucose + B27+NAHCO3+VitC | DMEM High Glucose+ B27+NAHCO3+VitC |
| 1 day | 1 day | 2 days | 2 days | 4 days | 8 days |

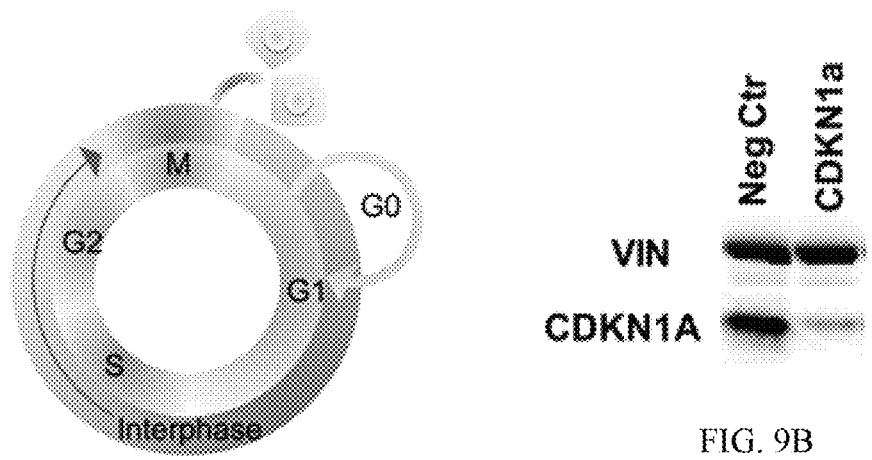
FIG. 9A
FIG. 9B
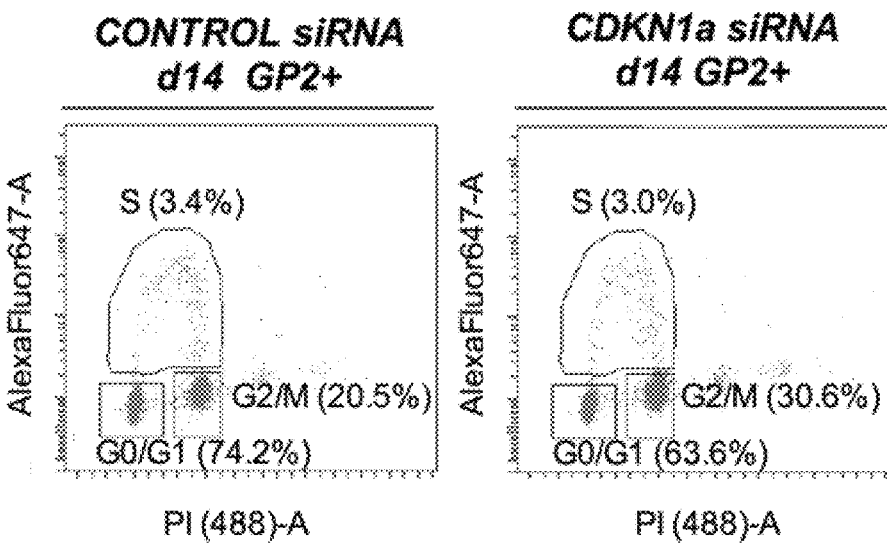
FIG. 9C
FIG. 9D
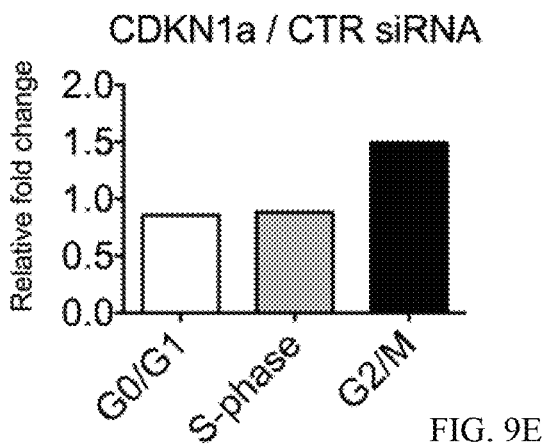
FIG. 9E

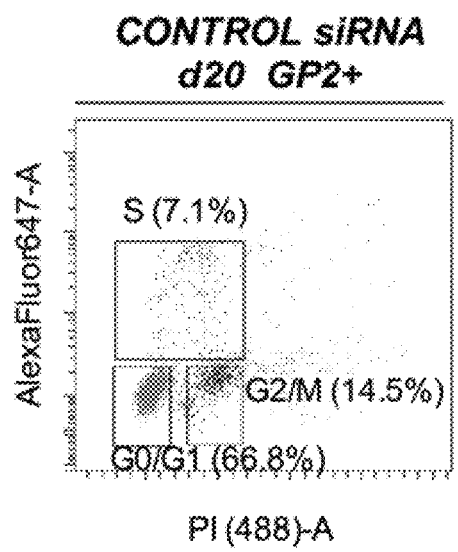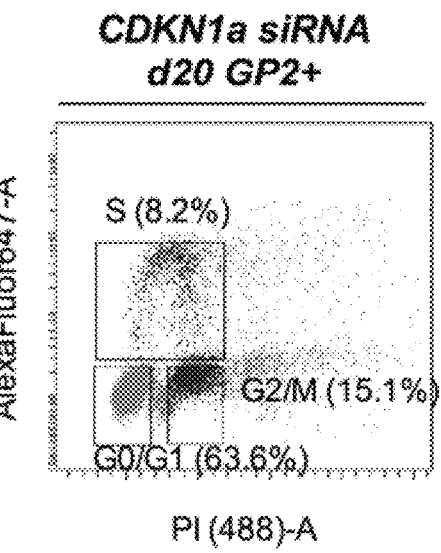
FIG. 9F    FIG. 9G
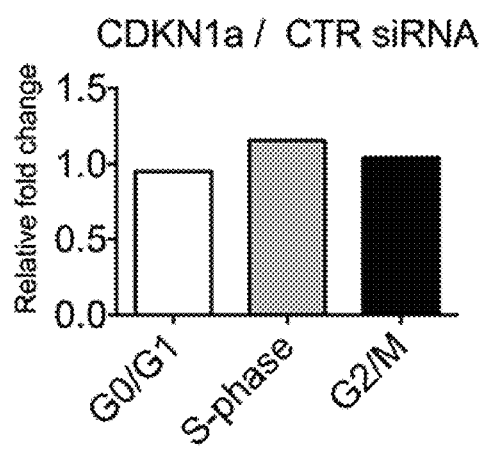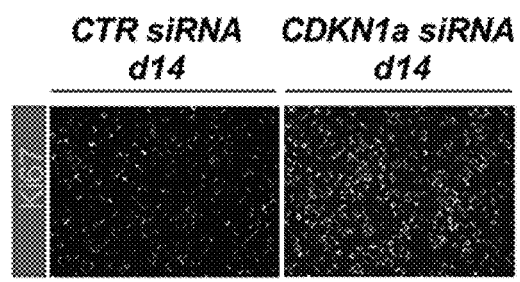
FIG. 9H    FIG. 9I

ISOLATION OF BONA FIDE PANCREATIC PROGENITOR CELLS

RELATED APPLICATIONS

This application is a divisional of U.S. application Ser. No. 15/568,978, filed Oct. 24, 2017, which is the U.S. National Stage Application of International Application No. PCT/EP2016/058920 filed on Apr. 21, 2016, published in English, which claims priority under 35 U.S.C. § 119 or 365 to European Application No. 15164999.3, filed Apr. 24, 2015. The entire teachings of the above applications are incorporated herein by reference.

FIELD OF INVENTION

The present invention relates to a method for isolating bona fide pancreatic progenitor cells.

BACKGROUND OF INVENTION

Cell therapy treatment of insulin dependent diabetes is facilitated by the production of unlimited numbers of pancreatic cells that can and will be able to function similarly to human islets. Accordingly, there is a need for producing these pancreatic cell types derived from human embryonic stem (hES) cells, as well as reliable methods for purifying such cells. For example, the use of insulin-producing β-cells derived from human embryonic stem cells (hESCs) would offer a vast improvement over current cell therapy procedures that utilize cells from donor pancreases. Currently cell therapy treatments for diabetes mellitus, such as type 1 or type 2 diabetes, which utilize cells from donor pancreases, are limited by the scarcity of high quality islet cells needed for transplant. For example, cell therapy for a single type 1 diabetic patient requires a transplant of approximately $8 \times 10^8$ pancreatic islet cells (Shapiro et al, 2000, N Engl J Med 343:230-238; Shapiro et al, 2001a, Best Pract Res Clin Endocrinol Metab 15:241-264; Shapiro et al, 2001b, British Medical Journal 322:861). As such, at least two healthy donor organs are required to obtain sufficient islet cells for a successful transplant.

Embryonic stem (ES) cells thus represent a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of ES cells can potentially be used to generate an unlimited source of cells suited to transplantation for treatment of diseases that result from cell damage or dysfunction. Other pluripotent cells and cell lines including early primitive ectoderm-like (EPL) cells, in vivo or in vitro derived ICM/epiblast, in vivo or in vitro derived primitive ectoderm, primordial germ cells (EG cells), teratocarcinoma cells (EC cells), and pluripotent cells derived by dedifferentiation or by nuclear transfer can also be used.

Accordingly, there is a need for methods for isolation of bona fide pancreatic progenitor cells.

SUMMARY OF INVENTION

The present invention provides methods for isolating bona fide pancreatic progenitor cells expressing PDX1 and NKX6.1. The present methods are based on the use of markers specific for PDX1 and/or NKX6.1-expressing cells, or on the use of markers specific for cells that do not express PDX1. Also provided are cell populations obtainable by such methods, as well as their use for treating metabolic disorders.

DESCRIPTION OF DRAWINGS

FIG. 1A) The gene encoding green fluorescent protein (eGFP) was inserted into the 5' untranslated region (UTR) of the PDX1 gene in the hPS cell line HUES-4. BD primers amplify the WT allele, AC primers amplify all transgenic clones, and AD primers amplify the targeted allele (3'HA). FIG. 1B) A representative PCR screen of 4 targeting events is shown for 4 individual clones (lane 1 and 4: clones positive for gene targeting; lane 2) with Neo/F and Ex3/R primers (fragment size 5,1 kb). The PDX1eGFP BAC containing the reporter cassette integrated into the PDX1 locus was used as positive control (BAC). FIG. 1C) A table showing the relative targeting efficiency that was obtained in 3 different hPS cell lines. FIG. 1D) Fluorescence and corresponding phase contrast images are shown of the targeted PDX1-eGFP hES cell line at day 13. Scale bar=100 μm. FIG. 1E) Immunofluorescence images of the PDX1-GFP targeted cell line showing co-localization of the endogenous PDX1 expression (red) with GFP (green) at day 16. Scale bar=50 μm. FIG. 1F) Immunofluorescence analysis of the PDX1-eGFP+ cell population at day 17. A significant number of the GFP+/PDX1+ cells co-expressed NKX6-1, and SOX9. The majority of the PDX1+ cells also expressed ECAD and HES1 (data not shown). Scale bars=50 μm.

FIG. 2A) hPSCs were differentiated according to two different differentiation protocols to obtain either pancreatic progenitors co-expressing PDX1 and NKX6-1 (protocol A (PE)) or posterior foregut cells expressing PDX1 but lacking NKX6-1 (protocol B (PFG)). FIG. 2B Schematic depicting the differentiation protocol referred to as "protocol A", generating pancretic endoderm (PE). FIG. 2C) FACS isolation of eGFP+ and eGFP- fractions at day 17 in hPSCs treated according to protocol A. FIG. 2D) Gene expression analysis of sorted eGFP+ and eGFP—cells showed significant enrichment of pancreatic endoderm markers (importantly PDX1 and NKX6-1) in the eGFP+ cells obtained with protocol A. The data are shown as mean expression±SEM (n=5). The graphs represent the fold increase in comparison to that detected in the control samples (eGFP- cells) at day seventeen. The control sample was arbitrarily set to a value of one. FIG. 2D) Schematic depicting the differentiation protocol referred to as "protocol B", generating posterior foregut cells. FIG. 2F) FACS isolation of eGFP+ and eGFP- cells (from day 17) differentiated according to protocol B. FIG. 2G) Gene expression analysis of sorted eGFP+ and eGFP— cells showed that whereas posterior foregut markers such as PDX1, ECAD, HNF6, and SOX9 were enriched in the eGFP+ cells, neither NKX6-1 nor MNX1 were significantly up-regulated in the eGFP+ cells obtained by protocol B. The data are shown as mean expression±SEM (n=2-4). The graphs represent the fold increase in comparison to that detected in the control samples (eGFP- cells) at day seventeen. The control sample was arbitrarily set to a value of one.

FIG. 3A) Hierarchical clustering of genes differentially expressed in the pancreatic progenitors (PDX1+/NKX6-1+), posterior foregut cells (PDX1+/NKX6-1−), and GFP− cells. FIG. 3B) Venn diagrams showing the distribution of genes up-regulated in PPCs vs GFP−, PPCs vs PFG, and PFG vs GFP− cells at day 17. FIG. 3C) Hierarchical clustering of the genes differentially expressed in the 3-comparison analysis depicted in A (average expression levels are shown). The bars indicate sub-clusters with relevant genes; nine different sub-clusters were created in total. Sub-cluster 3a shows genes enriched in the GFP− cell population, including the novel cell surface marker CD49d (ITGA4), whereas sub-cluster 5 displays genes enriched in the pancreatic progenitor cells (GFP+ cell fraction), also including the novel cell surface marker GP2. Sub-cluster 6 indicates genes enriched in PDX1+ cells irrespective of NKX6-1 expression (F2 GFP+ and GFP+ cells), such as CDH1 (ECAD), EPCAM, F3 (CD142) and the novel cell surface marker FOLR1. FIG. 3D) Gene ontology (GO) analysis showing enrichment of genes in the PDX1+/NKX6-1+ pancreatic progenitor cells. Representative GO categories are shown and plotted against −log (p-value).

FIG. 4A) Heatmap showing enrichment of genes localized in the plasma membrane or the extracellular region in the GFP+ and GFP− fractions. Arrows indicate selected cell surface markers enriched in the different cell populations. FIG. 4B) Flow cytometric analysis of the selected cell surface markers GP2, and CD49d (ITGA4) performed on differentiated hPSCs cultured on MEFs (d17), confirmed that GP2 were highly expressed in the GFP+ cells whereas CD49d was enriched in the GFP− cells. More specifically, the majority of the GFP− cells (70-72%) at d17 expressed CD49d while 64-76% of the GFP+ cells co-expressed GP2. Importantly, only a low fraction of the GFP− cells (3-7%) expressed GP2 and basically none (1-2%) of the GFP+ cells expressed CD49d. FIG. 4C) Gene expression analysis of the sorted cell populations showed that the pancreatic endoderm markers and the novel cell surface markers were highly enriched in GP2+/CD49d−sorted cell population. FIG. 4D) The expression of GP2 and CD49d, was analyzed by flow cytometry in a genetically untagged cell line, HUES-4, cultured in a feeder free system. FIG. 4E) GP2+CD49d−, CD49d+GP2−, and GP2-CD49d− cell fractions were sorted out and the gene expression patterns were analyzed. Pancreatic endoderm markers such as PDX1, SOX9, MNX1, and NKX6-1 and the novel cell surface markers GP2 and FOLR1 were significantly enriched in the GP2+CD49d− cell fractions. The remaining PDX1+ cells in the GP2-CD49d− cell fractions express only low levels of NKX6-1, confirming that GP2 specifically enrich for PDX1+/NKX6-1+ cells. FIG. 4F) Flow cytometric analysis of GP2 and CD49d expression in human fetal pancreas (9.1 WD) gated on non-hematopoietic and non-endothelial cells (CD45-CD31−). FIG. 4G) qPCR analysis of PDX1, and NKX6-1 expression in FACS sorted GP2+ and CD49d+ (gated on CD45-CD31−) cell populations, showed significant enrichment of PDX1 and NKX6- in the GP2+ vs. the CD49d+ cells. Results are presented in arbitrary units (AU) relative to expression of the control gene Hprt or Gapdh. *P=0.023 and **P=0.010. ND=Non Detected. FIG. 4H) Flow cytometric analysis of PDX1 and NKX6-1 expression in GP2+ (CD45−/CD31−) and CD45+/CD31+ cells at 8.7 WD. 91% of the GP2+(PDX1+) cells co-expressed NKX6.1. CD45+CD31+ cells were used as a negative control for PDX1 and NKX6-1 expression. FACS plots are representative of 3 independent experiments. This result corroborates our previous findings indicating that GP2 specifically marks pancreatic progenitors co-expressing PDX1 and NKX6.1.

FIG. 5A) FACS analysis of the markers FOLR1 in combination with CD49d in the PDXeG cell line cultured on MEFs. FIG. 5B) FOLR1−/+CD49d+, CD49d−/FOLR1+, and GFP+/FOLR1− cell fractions were sorted out and the gene expression pattern was analyzed. FIG. 5C) FACS analysis of FOLR1 and CD49d in the genetically untagged cell line HUES4, cultured in a feeder free system. FIG. 5D) qPCR analysis was also performed on FOLR1−Cd49d+, FOLR1−Cd49d−, and FOLR1+Cd49d− cells. Pancreatic endoderm markers such as PDX1, SOX9, MNX1, and NKX6-1 and the novel cell surface markers GP2 and FOLR1 were significantly enriched in the FOLR1+ CD49d− cell fractions. The data are shown as mean expression±SEM. The graphs represent the fold increase in comparison to that detected in the control samples (eGFP− cells) at day seventeen. As FOLR1 is expressed in both PDX1+/NKX6-1+ and PDX1/NKX6-1− cells it's not as specific/efficient as GP2 in marking PPCs, consequently FOLR1−CD49d− cell fraction still contain PDX1, NKX6-1 expressing cells.

FIG. 6A) Scheme for inducing hPSC-derived pancreatic progenitors according to a slightly modified version of the differentiation protocol published by Rezania et al., 2013. FIG. 6B) Using the PDXeG cell line, differentiated hPSCs were sorted out based on GFP and GP2 expression and analyzed by qPCR.

FIG. 7A) Flow cytometric analysis of the previously identified cell surface markers CD142 and CD200 in the PDXeG reporter cell line cultured on MEFs. The majority of the GFP+ and GFP− cells are stained with CD142 and CD200, showing that these markers are not specific enough in recognizing the PDX1+/NKX6-1+ cells in a heterogeneous cell culture. FIG. 7B) A genetically untagged cell line (HUES4) was differentiated according to a slightly modified version of the differentiation protocol published by Rezania et al 2013) in a feeder free culture system and stained with GP2 in combination with CD49d, CD142, and CD200. FIG. 7C) qPCR analysis of the different sorted populations (GP2−, GP2+, CD142+, and CD200+) confirmed significant enrichment of PDX1 and NKX6-1 in the GP2+ cells. These results illustrate that GP2 is superior in labeling PDX1+/ NKX6-1+ pancreatic progenitors in comparison to the previously published markers CD142 and CD200.

FIG. 8A) Schematic illustrating differentiation of hPSCs into pancreatic progenitors that are dissociated and stained with the cell surface markers CD49d and GP2. FIG. 8B) A table depicting the differentiation protocol that was applied to differentiate the replated FACS sorted GP2+/CD49d− pancreatic progenitor cells into insulin expressing cells. For: Forskolin (10 uM), Alki: Alk5 inhibitor (4.5 uM), Nic: Nicotinamide (10 mM), Rocki: Rock inhibitor (10-15 uM)), DF12: DMEM/F-12, B27: B27 Supplement. FIG. 8C). FACS plot displaying GP2 and CD49d staining of differentiated hPCS at d18. FIG. 8D) Differentiated GP2+(CD49d−) PPCs, and GP2low(CD49d−) cells isolated from the genetically untagged cell line HUES4 displays a significant enrichment of C-peptide+ cells in the GP2+(CD49d−) cells. FIG. 8E) Immunofluorescence analysis of purified and replated GP2+(CD49d−) pancreatic progenitor cells (isolated from the genetically untagged cell line HUES4) differentiated into insulin expressing cells. FIG. 8F). Percentage of CPEP expressing cells in Gp2 low vs GP2+ cells at d18. FIG. 8G) The release of human C-peptide was measured in the differentiated GP2+(CD49d−) cells by a static glucose-stimulated insulin secretion assay (GSIS). The results showed that stimulation with high concentration of glucose results in a statistically significant increase of C-peptide, indicating that the main triggering (K-ATP channel dependent) pathway is functional in the GP2+ PPC-derived beta cells.

FIGS. 9A-9I. CDKN1a knockdown results in a significant increase of proliferating GP2+ PPCs. FIG. 9A) A schematic showing the various stages of the cell cycle. FIG. 9B) Differentiated hPSCs from day 11 were transfected with control and CDKN1 siRNA. 72 h after transfection samples were taken and analyzed by western blot analysis. Knock down of CDKN1a in hPSCs consisting of premature GP2+ pancreatic progenitors, results in a significant increase in number of cells at the G2/M phase by d14 FIGS. 9C-9E). This increase correlates with a reduction in the number of G0/G1 cells, suggesting that reducing the levels of p21 promotes the transition of cells from G0/G1 into a proliferative state (G2/M). If p21 is however knocked down at a later time point (d17), when more mature GP2+ pancreatic progenitors are present in the hPSC-culture, the proliferative effect is abolished FIGS. 9F-9H). FIG. 9I) Immunofluorescence analysis of siRNA treated hPSCs from day 14 reveals a significant up-regulation of Ki67+ cells after 72 h of knockdown of CDKN1a. These data provide evidence that CDKN1a knock down in early pancreatic progenitor can be utilized to expand the pool of GP2+ hPPCs during in vitro culture.

DETAILED DESCRIPTION OF THE INVENTION

Figure 1A:
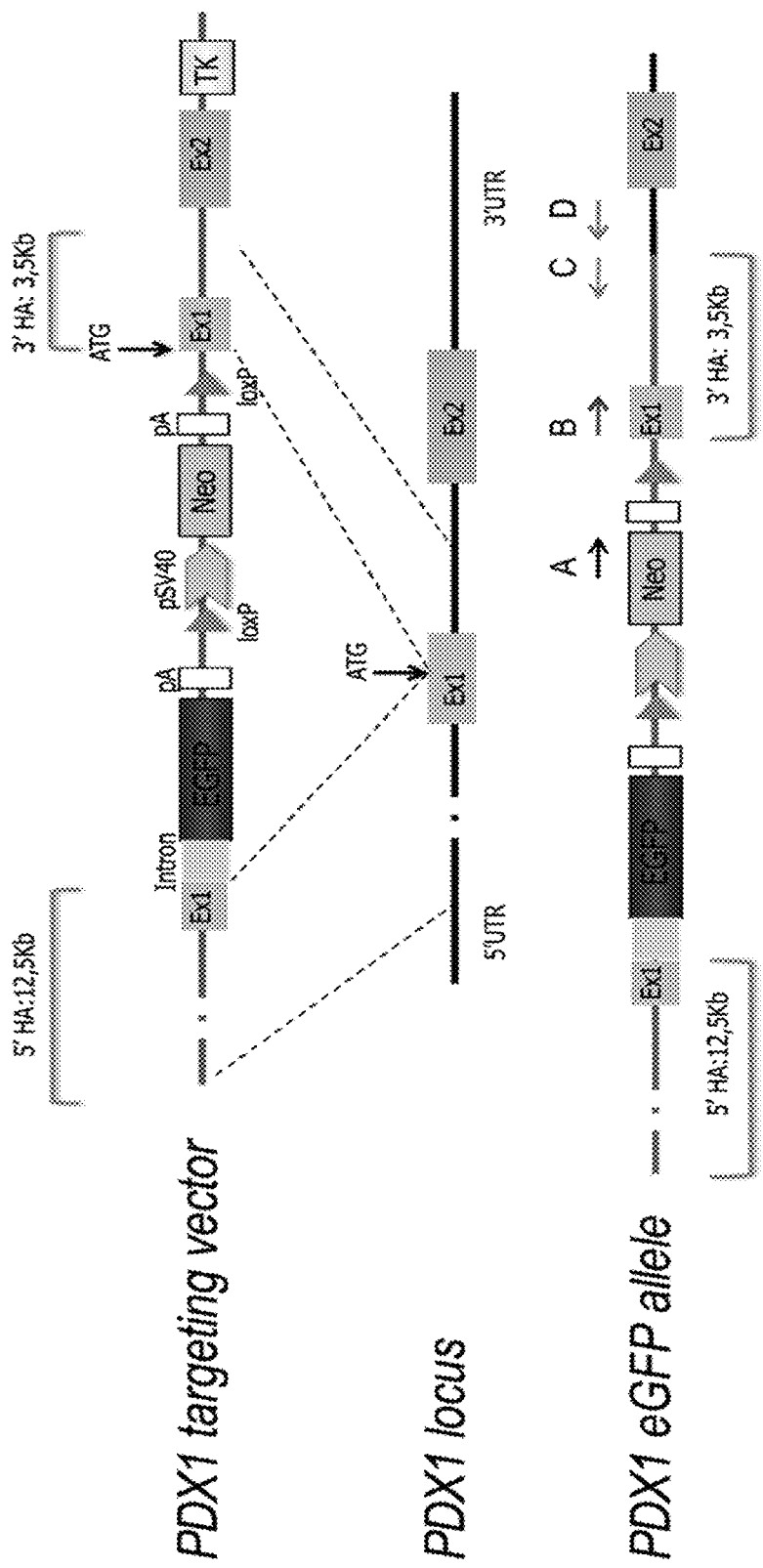
FIGS. 1A-1F. Targeting of eGFP into the human PDX1 Locus.

The invention is as defined in the claims.

The present inventors have identified novel markers useful for the isolation of true pancreatic progenitor cells.

The most recent success in generating hPSC-derived glucose responsive insulin-producing cells that share functional properties with normal beta cells (Pagliuca et al., 2014, Rezania et al., 2014), have made the implementation of a cell-based therapy for the treatment of type I diabetes a palpable reality. The therapeutic success of this approach will depend on the ability to upscale production of hPSC-derivatives. Estimates put the number of functional cells required for organ repair and disease recovery in the order of $10^9$ per patient (Pagliuca et al., 2014, Kempf et al., 2016). Thus, differentiation strategies will need to be adapted for mass production at an industrial scale. Currently, generation of glucose-responsive insulin-producing cells requires tedious and complicated multistep protocols, where undifferentiated hPSCs with tumorigenic propensity are used as the starting cell population. By establishing strategies where more mature cells are used for generating beta cells, the potential contamination with tumor-causing cells in the final cell preparation to be used for cell therapy could be prevented, and safer and more reproducible manufacturing procedures could be achieved. However, stage-specific surface markers that can be used to purify late stage cell populations during pancreatic differentiation are lacking.

During normal embryonic development the highly proliferative human and mouse pancreatic progenitors, recognized by their co-expression of the transcription factors Pancreatic duodenal homeobox 1 (PDX1) and NK6 homeobox 1 (NKX6-1), are responsible for the proper growth of the pancreatic epithelium and give rise to all the pancreatic cell types including exocrine, ductal, and endocrine cells. Consequently, pancreatic progenitor cells could serve as an ideal starting population for the generation of hormone producing endocrine cells such as the beta cells. Furthermore, previous publications support the notion that enrichment of pancreatic progenitors would reduce the risk of teratoma formation upon transplantation. Isolation of hPPCs could be obtained using tissue-specific cell surface molecules, and in fact markers for hPSC-derived pancreatic cell populations (CD142 for pancreatic progenitors and CD200/CD318 for endocrine cells) have been reported (Kelly 2011). However, the specificity of the pancreatic progenitor marker CD142 was questionable, as the populations enriched with this molecule were not exclusively composed of pancreatic progenitor cells as pointed out by the authors. Hence, the need for new and more specific markers to enrich for a progenitor population remains to be fulfilled.

Generation of tissue specific reporter cell lines could aid in the process of identifying pancreas-specific cell surface markers. Thus we established a PDX1-eGFP reporter cell line (PDXeG) by gene targeting in order to enable the isolation of pure PDX1+ pancreatic progenitor cells from hPSCs. By using the PDXeG reporter cell line as a genetic tool, we were able to isolate different subpopulations of PDX1+ cells and perform a genome wide expression analysis that allowed us to identify novel cell surface markers for isolation of hPPCs. Specifically, we identified three novel cell surface markers allowing us to separate true pancreatic progenitors from posterior foregut endoderm cells: glycoprotein 2 (zymogen granule membrane) (GP2) as a marker for isolation of PDX1+/NKX6-1+ hPPCs, Integrin Alpha-4 (ITGA4 or CD49d) as a negative selection marker labeling the PDX1− cell fraction, and finally a third marker, Folate receptor 1 (adult) (FOLR1) recognizing the PDX1+/NKX6-1− cells.

The specificity of these markers was demonstrated by using human fetal pancreas tissue. Furthermore, using a simplified and defined differentiation strategy, we show that the GP2+/CD49d− pancreatic progenitors retain the capacity to mature into endocrine cells and differentiated into glucose responsive insulin producing cells. Finally, we performed a siRNA screen, targeting candidate genes identified by microarray and found a new gene involved in the expansion of the hPPCs. Altogether, the inventors provide I) novel cell surface markers for isolation of hPPCs, II) a simplified and defined differentiation strategy to obtain glucose responsive insulin producing cells from isolated hPPCs, III) and novel insight into how hPPCs can be expanded in vitro, permitting not only further in depth characterization of hPPCs but also promoting development of novel strategies for expanding these progenitors for future cell replacement therapy of diabetes.

Accordingly, in a first aspect the invention relates to a method for isolating a population enriched for bona fide pancreatic progenitor cell, said method comprising the steps of:
  i) providing a cell population comprising at least one bona fide pancreatic progenitor cell, wherein the bona fide pancreatic progenitor cell expresses PDX1 and NKX6-1; and
  ii) exposing said cell population to:
    a) a first ligand which binds to a first marker specific for PDX1− cells and selecting the cells that do not bind to said first ligand from said cell population, thereby enriching the cell population for PDX1+ cells;
    and/or
    b) a second ligand which binds to a second marker specific for PDX1+ cells and selecting the cells that bind to said second ligand from the cells that do not bind to said second ligand, thereby enriching the cell population for PDX1+ cells;
    and/or
    c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
    thereby obtaining a cell population enriched for bona fide pancreatic progenitor cells.

In a further aspect, the invention relates to a method for producing a cell population enriched for bona fide pancreatic progenitor cells, said enriched cell population comprising at least 70% bona fide pancreatic progenitor cells.

In yet a further aspect, the invention relates to a cell population comprising at least 70% bona fide pancreatic progenitor cells.

In yet a further aspect, the invention relates to a cell population comprising bona fide pancreatic progenitor cells, obtainable by the method disclosed herein.

In yet a further aspect, the invention relates to a cell population comprising bona fide pancreatic progenitor cells, obtainable by the method disclosed herein for treatment of a metabolic disorder in an individual in need thereof.

In yet a further aspect, the invention relates to a cell population enriched for bona fide pancreatic progenitor cells as disclosed herein for treatment of a metabolic disorder in an individual in need thereof.

In yet a further aspect, the invention relates to a method of treatment of a metabolic disorder in an individual in need thereof, wherein the method comprises a step of providing a cell population as described herein.

Definitions

Antibody. The term 'antibody' describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein is used in the broadest sense and covers intact antibodies, chimeric, humanized, fully human and single chain antibodies, as well as binding fragments of antibodies, such as Fab, $F(ab')_2$, Fv fragments or scFv fragments, as well as multimeric forms such as dimeric IgA molecules or pentavalent IgM.

Antigen. An antigen is a molecule comprising at least one epitope. The antigen may for example be a polypeptide, polysaccharide, protein, lipoprotein or glycoprotein.

Bona fide pancreatic progenitor cell. The term 'bona fide pancreatic progenitor cell' or 'true pancreatic progenitor' refers herein to a cell, which is capable of differentiating into all pancreatic lineages, including acinar, duct and endocrine, such as insulin-producing cells.

Definitive endoderm. As used herein, "definitive endoderm" or "DE" refers to a multipotent cell that can differentiate into cells of the gut tube or organs derived from the gut tube. In accordance with certain embodiments, the definitive endoderm cells and cells derived therefrom are mammalian cells, and in a preferred embodiment, the definitive endoderm cells are human cells. In some embodiments, definitive endoderm cells express or fail to significantly express certain markers. In some embodiments, one or more markers selected from SOX17, CXCR4, MIXL1, GAT A4, FOXA2, GSC, FGF 17, VWF, CALCR, FOXQ1, CMKOR1, CER and CRIP1 are expressed in definitive endoderm cells. In other embodiments, one or more markers selected from OCT4, HNF4A, alpha-fetoprotein (AFP), Thrombomodulin (TM), SPARC and SOX7 are not significantly expressed in definitive endoderm cells. Definitive endoderm cells do not express PDX-1.

Differentiable or differentiated cell. As used herein, the phrase, "differentiable cell" or "differentiated cell" or "hES-derived cell" can refer to pluripotent, multipotent, oligopotent or even unipotent cells, as defined in detail below. In certain embodiments, the differentiable cells are pluripotent differentiable cells. In more specific embodiments, the pluripotent differentiable cells are selected from the group consisting of embryonic stem cells, ICM/epiblast cells, primitive ectoderm cells, primordial germ cells, and teratocarcinoma cells. In one particular embodiment, the differentiable cells are mammalian embryonic stem cells. In a more particular embodiment, the differentiable cells are human embryonic stem cells. Certain embodiments also contemplate differentiable cells from any source within an animal, provided the cells are differentiable as defined herein. For example, differentiable cells can be harvested from embryos, or any primordial germ layer therein, from placental or chorion tissue, or from more mature tissue such as adult stem cells including, but not limited to adipose, bone marrow, nervous tissue, mammary tissue, liver tissue, pancreas, epithelial, respiratory, gonadal and muscle tissue. In specific embodiments, the differentiable cells are embryonic stem cells. In other specific embodiments, the differentiable cells are adult stem cells. In still other specific embodiments, the stem cells are placental- or chorionic-derived stem cells.

Differentiation. As used herein, the term "differentiation" refers to the production of a cell type that is more differentiated than the cell type from which it is derived. The term therefore encompasses cell types that are partially and terminally differentiated. Similarly, "produced from hESCs," "derived from hESCs," "differentiated from hESCs," "hES derived cell" and equivalent expressions refer to the production of a differentiated cell type from hESCs in vitro and in vivo.

Embryonic. As used herein, "embryonic" refers to a range of developmental stages of an organism beginning with a single zygote and ending with a multicellular structure that no longer comprises pluripotent or totipotent cells other than developed gametic cells. In addition to embryos derived by gamete fusion, the term "embryonic" refers to embryos derived by somatic cell nuclear transfer.

Expression level. As used herein, the term "expression level" can refer to the level of transcript (mRNA) or to the level of protein for a particular gene or protein, respectively. Expression levels can thus be determined by methods known in the art, by determining transcription level or protein level. Transcription levels can be measured by quantifying the amount of transcript by methods such as, but not limited to, Northern blot, RT-PCR or microarray-based methods. Protein levels can be measured by methods such as, but not limited to, Western blot and immunostaining.

Human embryonic stem cells. The human embryonic stem cells are derived from the undifferentiated inner cell mass of the human embryo. These cells are pluripotent and are able to differentiate into all derivatives of the three primary germ layers namely: ectoderm, endoderm and mesoderm (Thomson et al., 1998). As used herein, the term "human pluripotent stem cells" (hPS) refers to cells that may be derived from any source and that are capable, under appropriate conditions, of producing human progeny of different cell types that are derivatives of all of the 3 germinal layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in literature often denoted as human embryonic stem (hES) cells (see, e.g., Thomson et al. (1998), Heins et. al. (2004), as well as induced pluripotent stem cells (see, e.g. Yu et al. (2007) Science 318:5858; Takahashi et al. (2007) Cell 131 (5):861). The various methods and other embodiments described herein may require or utilise hPS cells (hPSCs) from a variety of sources. For example, hPS cells suitable for use may be obtained from developing embryos. Additionally or alternatively, suitable hPS cells may be obtained from established cell lines and/or human induced pluripotent stem (hiPS) cells by methods, which do not require the destruction of embryos (Chung et al. 2008).

As used herein "hiPS cells" refers to human induced pluripotent stem cells.

As used herein, the term "blastocyst-derived stem cell" is denoted BS cell, and the human form is termed "hBS cells". In literature the cells are often referred to as embryonic stem cells, and more specifically human embryonic stem cells (hESCs). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent cells by e.g. the treating adult cells with certain transcription factors, such as OCT4, SOX2, NANOG, and LIN28 as disclosed in Yu, et al., 2007, Takahashi et al. 2007 and Yu et al 2009.

Inactivation: The term 'inactivation' is herein used in connection with inactivation of the function of a given protein in a cell and refers to manipulations of the cell in order to obtain a loss of function. Inactivation may be achieved as known in the art, e.g. by using an inhibitor capable of inhibiting the function of the protein. Inactivation can also be achieved by mutation or deletion of the gene encoding the protein. Silencing, for example by using siRNAs, can also be used to achieve inactivation, as known to the person skilled in the art. Inactivation may be transient or permanent. Inactivation may also be reversible or irreversible. For example, incubation of a cell population with an inhibitor will typically result in transient inactivation for as long as the inhibitor is effective or present. Removing the inhibitor from the environment will generally result in alleviation of the inactivation. Likewise, siRNAs will typically only have a silencing effect for as long as they are expressed or present. Deletion or mutation of a gene on the other hand will typically result in permanent inactivation, although the person skilled in the art will know how to reverse the effects of deletion or mutation, for example by gene editing methods.

Induced pluripotent stem cell. Induced pluripotent stem cells (or iPSCs) can be derived directly from adult cells by reprogramming (Takashashi et al., 2006). iPSCs can be induced by proteins and are then termed protein-induced pluripotent stem cells (piPSCs).

Ligand. As used herein, "ligand" refers to a moiety or binding partner that specifically binds or cross-reacts to the marker or target or receptor or membrane protein on the cell or to the soluble analyte in a sample or solution. The target on the cell includes but is not limited to a marker. Examples of such ligands include, but are not limited to, an antibody that binds a cellular antigen, an antibody that binds a soluble antigen, an antigen that binds an antibody already bound to the cellular or soluble antigen; a lectin that binds to a soluble carbohydrate or to a carbohydrate moiety which is a part of a glycoprotein or glycolipid; or functional fragments of such antibodies and antigens that are capable of binding; a nucleic acid sequence sufficiently complementary to a target nucleic acid sequence of the cellular target or soluble analyte to bind the target or analyte sequence, a nucleic acid sequence sufficiently complementary to a ligand nucleic acid sequence already bound to the cellular marker or target or soluble analyte, or a chemical or proteinaceous compound, such as biotin or avidin. Ligands can be soluble or can be immobilized on the capture medium (i.e., synthetically covalently linked to a bead), as indicated by the assay format, e.g., antibody affinity chromatography. As defined herein, ligands include, but are not limited to, various agents that detect and react with one or more specific cellular markers or targets or soluble analytes.

Marker. As used herein, "marker", "epitope", "target", "receptor" or equivalents thereof can refer to any molecule that can be observed or detected. For example, a marker can include, but is not limited to, a nucleic acid, such as a transcript of a specific gene, a polypeptide product of a gene, such as a membrane protein, a non-gene product polypeptide, a glycoprotein, a carbohydrate, a glycolipid, a lipid, a lipoprotein or a small molecule (for example, molecules having a molecular weight of less than 10,000 amu). A "cell surface marker" is a marker present at the cell surface.

Multipotent cell. As used herein, "multipotent" or "multipotent cell" refers to a cell type that can give rise to a limited number of other particular cell types. Multipotent cells are committed to one or more embryonic cell fates, and thus, in contrast to pluripotent cells, cannot give rise to each of the three germ layer lineages as well as extraembryonic cells.

Naïve stem cell and primed stem cell. Naïve stem cells have the potential to develop into any kind of cell, unlike primed stem cells, which are able to differentiate into several types of cells but are already predetermined to some extent. Naïve stem cells have been known to exist in mice but human naïve stem cells have only been described recently (Takashima et al., 2014). Naïve stem cells can self-renew continuously without ERK signalling, are phenotypically stable, and are karyotypically intact. They differentiate in vitro and form teratomas in vivo. Metabolism is reprogrammed with activation of mitochondrial respiration as in ESC. The pluripotent state of human cells can be reset by short-term expression of two components, NANOG and KLF2, as described in Takashima et al., 2014. Naive PSCs share many properties with the inner cell mass of the blastocyst, while the primed PSCs resemble epiblast cells of a more advanced, pregastrulating stage embryo. In the mouse, the naive state is represented by embryonic stem cells (mESCs) and the primed state by epiblast stem cells (EpiSCs). In humans, blastocyst derived ESCs have been regarded until recently as the human equivalent of mESCs. However, without being bound by theory, based on multiple characteristics such as flat morphology, dependence on growth factors, or X-chromosome inactivation, hESCs (and human induced pluripotent stem cell (hiPSCs)) are closer to mouse EpiSCs than to mESCs and, as such, more likely correspond to the primed rather than the naive state of pluripotency (Tesar et al. 2007; Stadtfeld and Hochedlinger 2010).

Naturally occurring antibody. The term 'naturally occurring antibody' refers to heterotetrameric glycoproteins capable of recognising and binding an antigen and comprising two identical heavy (H) chains and two identical light (L) chains inter-connected by disulfide bonds. Each heavy chain comprises a heavy chain variable region (abbreviated herein as $V_H$) and a heavy chain constant region (abbreviated herein as $C_H$). Each light chain comprises a light chain variable region (abbreviated herein as $V_L$) and a light chain constant region (abbreviated herein as $C_L$). The $V_H$ and $V_L$ regions can be further subdivided into regions of hypervariability, termed complementarity determining regions (CDRs), interspersed with regions that are more conserved, termed framework regions (FRs). Antibodies may comprise several identical heterotetramers.

Pancreatic progenitor cell or multipotent pancreatic progenitor cell. A progenitor cell is a cell that is committed to differentiate into a certain type of cell. Pancreatic progenitor cells are thus multipotent and can differentiate and give rise to all cell types of the pancreas.

Partially mature cell. As used herein, "partially mature cells" refer to cells that exhibit at least one characteristic of the phenotype, such as morphology or protein expression, of a mature cell from the same organ or tissue. Some embodiments contemplate using differentiable cells from any animal capable of generating differentiable cells, e.g., pancreatic type cells such as beta cells. The animals from which the differentiable cells are harvested can be vertebrate or invertebrate, mammalian or non-mammalian, human or non-human. Examples of animal sources include, but are not limited to, primates, rodents, canines, felines, equines, bovines and porcines.

Pluripotent cell. By "pluripotent" is meant that the cell can give rise to each of the three germ layer lineages. Pluripotent cells, however, may not be capable of producing an entire organism. In certain embodiments, the pluripotent cells used as starting material are stem cells, including human embryonic stem cells. Pluripotent cells can be derived by explanting cells from embryos at different stages of development. PSCs (pluripotent stem cells) can be classified into two distinct states, naive and primed, depending on which stage they are during embryonic development.

Stem cell. A stem cell is an undifferentiated cell that can differentiate into specialized cells and can divide to produce more stem cells. The term stem cell comprises embryonic stem cells, adult stem cells, naïve stem cells as well as induced pluripotent stem cells. Stem cells are defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Totipotent stem cell: The term refers to a cell having the potential to give rise to any and all types of human cells such as all three germ layer lineages and extraembryonic lineages. It can give rise to an entire functional organism.

In the present disclosure, any gene or protein name can refer to the gene or the protein in any species. For example, PDX1 or Pdx1 are used interchangeably and can refer to either murine Pdx1 or human PDX1 or to Pdx1 in another species.

In the present disclosure, a "−" sign after a gene or protein name means that the gene or protein is not expressed, while a "+" sign after a gene or protein name means that the gene or protein is expressed. Thus PDX1− or PDX1− cells are cells that do not express PDX1, while PDX1+ or PDX1+ cells are cells that express PDX1.

Method for Isolating Bona Fide Pancreatic Progenitor Cells

It is an object of the present disclosure to provide a method for isolating a population enriched for bona fide pancreatic progenitor cell, said method comprising the steps of:
  i) providing a cell population comprising at least one bona fide pancreatic progenitor cell, wherein the bona fide pancreatic progenitor cell expresses PDX1 and NKX6-1; and
  ii) exposing said cell population to:
    a) a first ligand which binds to a first marker specific for PDX1− cells and selecting the cells that do not bind to said first ligand from said cell population, thereby enriching the cell population for PDX1+ cells;
and/or
b) a second ligand which binds to a second marker specific for PDX1+ cells and selecting the cells that bind to said second ligand from the cells that do not bind to said second ligand, thereby enriching the cell population for PDX1+ cells;
and/or
c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
thereby obtaining a cell population enriched for bona fide pancreatic progenitor cells.

Bona Fide Pancreatic Progenitor Cells

Figure 10:
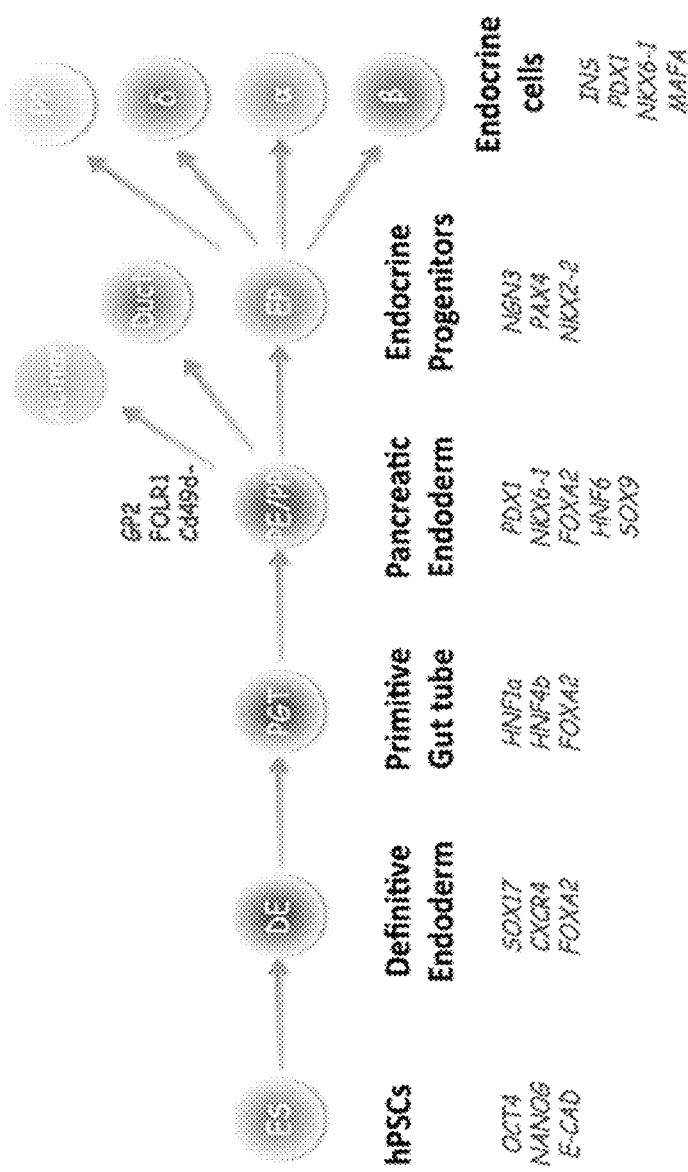
FIG. 10. Schematic showing the intermediate stages of hESC differentiation towards insulin producing cells. The novel cell surface markers GP2, FOLR1 and CD49d can be used to isolate pancreatic progenitor cells at PE stage. These pancreatic progenitor cells have the capacity to differentiate into acinar-, ductal-, and also the endocrine cells that comprise the pancreas.

In the pancreas several different types of pancreatic cells may be found. The pancreatic cells include for example multi-potent pancreatic progenitor cells, ductal/acinar progenitor cells, fully differentiated acinar/exocrine cells, ductal/endocrine progenitor cells, endocrine progenitor cells, early endocrine cells, and/or fully differentiated endocrine cells. The different stages of hPSCs towards endocrine cells are represented in FIG. 10. Pancreatic endoderm progenitor cells expressing PDX1 and NKX6-1 have the capacity to differentiate into acinar cells, ductal cells or endocrine cells. The term 'bona fide pancreatic progenitor cell' or 'true pancreatic progenitor' refers herein to a cell, which is capable of differentiating into all pancreatic lineages, including acinar, duct and endocrine, such as insulin-producing cells.

Pancreatic early endocrine cells are cells, which have initiated expression of one of the pancreatic endocrine hormones (insulin, glucagon, somatostatin and pancreatic polypeptide) but do not share all the characteristics of fully mature pancreatic endocrine cells found in the Islet of Langerhans in the adult pancreas. These cells may be endocrine cells which have turned off Ngn3 but do not share all the characteristics of fully differentiated pancreatic endocrine cells found in the Islet of Langerhans in the adult pancreas, such as responsiveness to glucose, and are positive for one of the pancreatic endocrine hormones (insulin, glucagon, somatostatin, pancreatic polypeptide, and ghrelin).

Pancreatic endocrine cells, or pancreatic hormone-producing cells, are cells capable of expressing at least one of the following hormones: insulin, glucagon, somatostatin, pancreatic polypeptide and ghrelin.

"Pancreatic fully differentiated endocrine cells" (also termed "fully differentiated endocrine cells", "pancreatic mature endocrine cells", "pancreatic endocrine cells" or "pancreatic adult endocrine cells") are cells, which share all the characteristics of fully differentiated pancreatic endocrine cells found in the Islet of Langerhans in the adult pancreas.

The methods disclosed herein can be used to isolate pancreatic progenitor cells at the pancreatic endoderm stage. These cells may have the potential to differentiate further, for example into pancreatic hormone-producing cells such as β-cells and/or insulin-producing cells. The insulin-producing cells may be responsive to glucose. However, the cells obtained by the present methods can differentiate into any type of pancreatic cell.

Markers and Ligands

PDX1 (Pancreatic and duodenal homeobox 1), also known as insulin promoter factor 1, is a transcription factor necessary for pancreatic development and β-cell maturation. In embryonic development, PDX1 is expressed by a population of cells in the posterior foregut region of the definitive endoderm, and PDX1+ epithelial cells give rise to the developing pancreatic buds, and eventually, the whole of the pancreas—its exocrine, endocrine, and ductal cell populations (FIG. 11). Pdx1 is also necessary for β-cell maturation: developing β-cells co-express PDX1, NKX6-1, and insulin, a process that results in the silencing of MafB and the expression of MafA, a necessary switch in maturation of β-cells. PDX1+ pancreatic progenitor cells also co-express Hlxb9, Hnf6, Ptf1a and Nkx6-1 (homeobox protein Nkx-6.1), and these progenitor cells form the initial pancreatic buds, which may further proliferate. Pancreatic endocrine cells express PDX1 and NKX6-1 (PDX1+ NKX6-1+ cells).

The present method is based on the identification of surface markers specific for cells that do not express PDX1 (PDX1− cells), while other markers were identified as being specific for cells that express PDX1 (PDX1+), and yet others as being specific for cells that express PDX1 and NKX6-1. Molecules capable of binding to such markers shall herein be referred to as "ligands" and can be used to isolate true pancreatic progenitor cells.

Accordingly, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) exposing said cell population to:
a) a first ligand which binds to a first marker specific for PDX1− cells and selecting the cells that do not bind to said first ligand from said cell population, thereby enriching the cell population for PDX1+ cells;
and/or
b) a second ligand which binds to a second marker specific for PDX1+ cells and selecting the cells that bind to said second ligand from the cells that do not bind to said second ligand, thereby enriching the cell population for PDX1+ cells;
and/or
c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
thereby obtaining a cell population enriched for bona fide pancreatic progenitor cells.

It will be understood that the cell population can be exposed to any of the first and/or second and/or third ligand in simultaneous steps or in subsequent steps and that the steps can be performed in any order. In some embodiments, the cell population is exposed only to only one of the first, second or third ligand. In other embodiments, the cell population is exposed to two or three of the first, second or third ligand. In some embodiments, the cell population is exposed to the first, the second and the third ligand simultaneously. In some embodiments, the cell population is exposed to the first ligand and to the second ligand in separate steps. In other embodiments, the cell population is exposed to the first ligand and to the third ligand in separate steps. In other embodiments, the cell population is exposed to the first ligand and to the second or third ligand simultaneously. In other embodiments, the cell population is exposed to the first ligand and in a separate step is exposed to the second and third ligand simultaneously. In other embodiments, the cell population is exposed simultaneously to the first and second or third ligand. In other embodiments, the cell population is exposed simultaneously to the first and second ligand, and is exposed to the third ligand in a separate step. In other embodiments, the cell population is exposed simultaneously to the first and third ligand, and is exposed to the second ligand in a separate step.

Starting Cell Population

In a first step, a cell population comprising at least one bona fide pancreatic progenitor cell is provided, where the bona fide pancreatic progenitor cell expresses PDX1 and NKX6-1.

In some embodiments, the starting cell population comprises at least 5% bona fide pancreatic progenitor cells, such as at least 10% bona fide pancreatic progenitor cells, such as at least 15% bona fide pancreatic progenitor cells, such as at least 20% bona fide pancreatic progenitor cells, such as at least 25% bona fide pancreatic progenitor cells, such as at least 30% bona fide pancreatic progenitor cells, such as at least 35% bona fide pancreatic progenitor cells, such as at least 40% bona fide pancreatic progenitor cells, such as at least 45% bona fide pancreatic progenitor cells, such as at least 50% bona fide pancreatic progenitor cells, such as at least 55% bona fide pancreatic progenitor cells, such as at least 60% bona fide pancreatic progenitor cells, such as at least 65 bona fide pancreatic progenitor cells, such as at least 70% bona fide pancreatic progenitor cells, such as at least 75% bona fide pancreatic progenitor cells, such as at least 80% bona fide pancreatic progenitor cells.

In order to determine the fraction of bona fide progenitor cells comprised in the enriched population, methods known in the art can be employed, such as, but not limited to, immunostaining or flow cytometry methods.

Without being bound by theory, the percentage of bona fide pancreatic progenitor cells in the starting cell population can be estimated by the expression of GP2. Thus in some embodiments, the starting cell population comprises at least 5% cells expressing GP2, such as at least 10% cells expressing GP2, such as at least 15% cells expressing GP2, such as at least 20% cells expressing GP2, such as at least 25% cells expressing GP2, such as at least 30% cells expressing GP2, such as at least 35% cells expressing GP2, such as at least 40% cells expressing GP2, such as at least 45% cells expressing GP2, such as at least 50% cells expressing GP2, such as at least 55% cells expressing GP2, such as at least 60% cells expressing GP2, such as at least 65% cells expressing GP2, such as at least 70% cells expressing GP2, such as at least 75% cells expressing GP2, such as at least 80% cells expressing GP2, such as at least 85% cells expressing GP2. GP2 expression can be determined by methods known in the art, such as immunostaining methods, flow cytometry methods or quantitative measurements of transcription levels.

Likewise, without being bound by theory, the percentage of PDX1+ NKX6-1+ cells in the starting cell population can be estimated by the expression of GP2. Thus in some embodiments, the starting cell population comprises at least 5% cells expressing GP2, such as at least 10% cells expressing GP2, such as at least 15% cells expressing GP2, such as at least 20% cells expressing GP2, such as at least 25% cells expressing GP2, such as at least 30% cells expressing GP2, such as at least 35% cells expressing GP2, such as at least 40% cells expressing GP2, such as at least 45% cells expressing GP2, such as at least 50% cells expressing GP2, such as at least 55% cells expressing GP2, such as at least 60% cells expressing GP2, such as at least 65% cells expressing GP2, such as at least 70% cells expressing GP2, such as at least 75% cells expressing GP2, such as at least 80% cells expressing GP2, such as at least 85% cells expressing GP2. GP2 expression can be determined by methods known in the art, such as immunostaining methods, flow cytometry methods or quantitative measurements of transcription levels.

In some embodiments, the cell population may be derived or isolated from an individual, such as, but not limited to, a mammal, for example a human.

In some embodiments, the cells are derived from cells capable of differentiation, such as pluripotent stem cells, for example human pluripotent stem cells (hPSCs). hPSCs include human induced pluripotent stem cells (hiPSCs), human embryonic stem cells (hESCs) and naïve human stem cells (NhSCs).

In one embodiment, the cell population comprising pancreatic cells is obtained from a pancreas, including a foetal pancreas. In some aspects of the invention, the cell population comprising at least one bona fide pancreatic progenitor cell expressing PDX1 and NKX6-1 is obtained from a pancreas, including a foetal pancreas or an adult pancreas. In one aspect, the pancreas is from a mammal, such as a human.

In another embodiment, the cell population comprising pancreatic cells is a somatic cell population. In some embodiments, the cell population comprising at least one bona fide pancreatic progenitor cell expressing PDX1 and NKX6-1 is obtained from a somatic cell population. In a further aspect of the invention, the somatic cell population has been induced to de-differentiate into an embryonic-like stem cell (ESC, e.g. a pluripotent cell, or hESCs for human ESCs). Such dedifferentiated cells are also termed induced pluri-potent stem cells (IPSCs, or hIPSCs for human IPSCs).

In yet another embodiment, the cell population comprising at least one bona fide pancreatic progenitor cell is ESCs or hESCs. In one embodiment, the cell population comprising at least one bona fide pancreatic progenitor cell is obtained from ESCs or hESCs. In some embodiments, the cell population comprising at least one bona fide pancreatic progenitor cell is a population of pluripotent cells such as ESC like-cells.

In some embodiments, differentiation of the cell population comprising at least one bona fide pancreatic progenitor cell is induced by methods known in the art. For example, differentiation can be induced in embryoid bodies and/or in monolayer cell cultures or a combination thereof.

In one aspect of the invention, the cell population comprising at least one bona fide pancreatic progenitor cell is of mammalian origin. In one aspect of the invention, the cell population comprising at least one bona fide pancreatic progenitor cell is of human origin. In some aspects of the invention, the cell population has been differentiated to the pancreatic endocrine lineage.

In one aspect of the invention, the cell population comprising pancreatic cells is obtained from one or more donated pancreases. The methods described herein are not dependent on the age of the donated pancreas. Accordingly, pancreatic material isolated from donors ranging in age from embryos to adults can be used.

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, lipase preparations and other enzymes are contemplated for use with the methods disclosed herein.

Isolated source material can be further processed to enrich for one or more desired cell populations prior to performing the present methods. In some aspects unfractionated pancreatic tissue, once dissociated for culture, can also be used directly in the culture methods of the invention without further separation. However, unfractionated pancreatic tissue, once dissociated for culture, can also be used directly in the culture methods of the invention without further separation, and will yield the intermediate cell population. In one embodiment the isolated pancreatic cellular material is purified by centrifugation through a density gradient (e.g., Nycodenz, Ficoll, or Percoll). The mixture of cells harvested from the donor source will typically be heterogeneous and thus contain alpha cells, beta cells, delta cells, ductal cells, acinar cells, facultative progenitor cells, and other pancreatic cell types.

A typical purification procedure results in the separation of the isolated cellular mate-rial into a number of layers or interfaces. Typically, two interfaces are formed. The upper interface is islet-enriched and typically contains 10 to 100% islet cells in suspension.

The second interface is typically a mixed population of cells containing islets, acinar, and ductal cells. The bottom layer is the pellet, which is formed at the bottom of the gradient. This layer typically contains primarily acinar cells, some entrapped islets, and some ductal cells. Ductal tree components can be collected separately for further manipulation.

The cellular constituency of the fractions selected for further manipulation will vary depending on which fraction of the gradient is selected and the final results of each isolation. When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In one embodiment, intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped islet cells, respectively, can also be used in culture. While both layers contain cells capable of giving rise to the enriched bona fide pancreatic progenitor cell population described herein, each layer may have particular advantages for use with the disclosed methods.

In one embodiment, the cell population is a population of stem cells. In another embodiment, the cell population is a population of stem cells differentiated to the pancreatic endocrine lineage. In one embodiment, the cell population is a population of stem cells that is obtained without the destruction of an embryo. Methods for obtaining stem cells without destroying embryos are known in the art (Chung et al., 2008).

A protocol for obtaining pancreatic cells from stem cells is exemplified by, but not limited to, the protocols described in D'Amour, K. A. et al. (2006); Jiang, J. et al. (2007); and Kroon, E. et al. (2008), Rezania et al (2012, 2014), Felicia W. Pagliuca et al (2014).

A protocol for obtaining pancreatic cells from somatic cells or somatic cells induced to dedifferentiate into pluripotent cells such as ES like-cells is exemplified by, but not limited to, the protocols described in Aoi, T. et al. (2008), Jiang, J. et al. (2007), Takahashi, K. et al. (2007), Takahashi and Yamanaka (2006), and Wernig, M. et al. (2007). Other protocols have been described by D'Amour, K. A. et al. (2006) or Kroon, E. et al. (2008).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

In some aspects "differentiate" or "differentiation" as used herein refers to a process where cells progress from an immature state to a less immature state. In another aspect "differentiate" or "differentiation" as used herein refers to a process where cells progress from an undifferentiated state to a differentiated state or from an immature state to a mature state. For example, undifferentiated pancreatic cells may be able to proliferate and express characteristics markers, like PDX1. Early undifferentiated embryonic pancreatic cells may be able to proliferate and express characteristics markers, like PDX1. In one embodiment mature or differentiated pancreatic cells do not proliferate and secrete high levels of pancreatic endocrine hormones. In some embodiments mature or differentiated pancreatic cells do not proliferate and secrete high levels of pancreatic endocrine hormones or digestive enzymes. In one embodiment, e.g., mature beta cells secrete insulin at high levels. In some embodiments e.g., mature beta cells secrete insulin at high levels in response to glucose. Changes in cell interaction and maturation occur as cells lose markers of undifferentiated cells or gain markers of differentiated cells. In one embodiment loss or gain of a single marker can indicate that a cell has "matured or differentiated". In some embodiments loss or gain of a single marker can indicate that a cell has "matured or fully differentiated". The term "differentiation factors" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like-peptide 1. In one embodiment, differentiation of the cells comprises culturing the cells in a medium comprising one or more differentiation factors.

In some embodiments, the cell population comprising at least one bona fide pancreatic progenitor cell is analysed to identify whether at least one of the cells of the starting population expresses markers characteristic of the pancreatic endocrine lineage and selected from the group consisting of NGN3, NEUROD, ISL1, PDX1, NKX6.1, NKX2.2, MAFA, MAFB, ARX, BRN4, PAX4 and PAX6, GLUT2, INS, GCG, SST, pancreatic poly-peptide (PP). In some embodiments markers characteristic of the pancreatic endocrine lineage are selected from the group consisting of PDX1 and NKX6-1. In one embodiment, a pancreatic endocrine cell is capable of expressing at least one of the following hormones: insulin, glucagon, somatostatin, and PP. In some embodiments, a pancreatic endocrine cell is capable of expressing at least one of the following hormones: insulin, glucagon, somatostatin, PP and ghrelin. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one embodiment, the pancreatic endocrine cell is a cell expressing markers characteristic of the beta cell lineage. A cell expressing markers characteristic of the beta cell lineage expresses PDX1 and may further express at least one of the following transcription factors: NGN3, NKX2-2, NKX6-1, NEUROD, 1SL1, FOXA2, MAFA, PAX4, and PAX6. In one embodiment, a cell expressing markers characteristic of the beta cell lineage is a beta cell. In one embodiment, the pancreatic endocrine cell is a cell expressing the marker NKX6-1. In another aspect of the invention, the pancreatic endocrine cell is a cell expressing the marker PDX1. In a further aspect of the invention, the pancreatic endocrine cell is a cell expressing the markers NKX6-1 and PDX1. PDX1 is homeodomain transcription factor implicated in pancreas development. Pax-4 is a beta cell specific factor and Pax-6 is a pancreatic islet cell (specific) transcription factor; both are implicated in islet development. Hnf-3 beta (also known as FoxA2) belongs to the hepatic nuclear factor family of transcription factors, which is characterized by a highly conserved DNA binding domain and two short carboxy-terminal domains. NeuroD is basic helix-loop-helix (bHLH) transcription factor implicated in neurogenesis. Ngn3 is a member of the neurogenin family of basic loop-helix-loop transcription factors. NKX2-2 and NKX6-1 as used herein are members of the Nkx transcription factor family. Islet-1 or 1SL-1 is a member of the LIM/homeodomain family of transcription factors, and is expressed in the developing pancreas. MAFA is a transcription factor expressed in the pancreas, and controls the expression of genes involved in insulin biosynthesis and secretion. NKX6-1 and PDX1 are co-expressed with PTF1a in the early pancreatic multipotent cell that can develop into all cell types found in the adult pancreas (e.g., acinar, ductal, and endocrine cells). Within this cell population cells that also transiently express NGN3 are found. Once a cell express or has expressed NGN3 it will be part of the endocrine lineage, giving rise to endocrine cells (one type being the insulin producing beta cell) that will later form the Islets of Langerhans. In the absence of NGN3 no endocrine cells form during pancreas development. As development progress NKX6-1 and PDX1 are co-expressed in the more central domain of the pancreas, which now becomes devoid of PTF1a expression and the NKX6-1 and PDX1 positive cells can no longer give rise to acinar cells. Within this NKX6-1 and PDX1 positive cell population a significant number of cells transiently co-express NGN3, marking them for the endocrine lineage like earlier in development.

In one embodiment, the bona fide pancreatic progenitor cells are derived from cells capable of differentiation. In a specific embodiment, the cells capable of differentiation are human pluripotent stem cells. In some embodiments, the cells capable of differentiation are selected from the group consisting of human iPS cells (hIPSCs), human ES cells (hESCs) and naive human stem cells (NhSCs).

The cells capable of differentiation may be derived from cells isolated from an individual.

CDKN1a, also dubbed P21, and CDKN2a, also P16, are cell cycle specific genes. CDKN1a (cyclin-dependent kinase inhibitor 1 or CDK-interacting protein 1), is a cyclin-dependent kinase inhibitor that inhibits the complexes of CDK2 and CDK1. CDKN1 thus functions as a regulator of cell cycle progression at G1 and S phase. CDKN2a (cyclin-dependent kinase inhibitor 2A, multiple tumor suppressor 1) is a tumor suppressor protein. It plays an important role in cell cycle regulation by decelerating cells progression from G1 phase to S phase, and therefore acts as a tumor suppressor that is implicated in the prevention of cancers.

The inventors have surprisingly found that inactivation of CDKN1a or CDKN2a in the starting cell population facilitates entry of the cell population in a replicating state corresponding to the G2/M phase, in particular when the starting cell population is PDX1 expressing pancreatic progenitor cells. Inactivation of CDKN1a or CDKN2a in the starting cell population may also facilitate entry of the cell population in the S phase. Thus inactivation of CDKN1a or CDKN2a may be useful for obtaining mature beta cells from expanded pancreatic progenitor cells.

In some embodiments, expression of CDKN1a and/or CDKN2a in the starting cell population is inactivated. In some embodiments, the starting cell population is a population of pancreatic progenitor cells expressing PDX1. The starting cell population may also be any of the populations described above. The skilled person knows how to inactivate expression of CDKN1a and/or CDKN2a. This may be done for instance by mutating or deleting the corresponding genes, by known gene editing methods. Alternatively, silencing means may be employed such as siRNA in order to prevent expression of CDKN1a and/or CDKN2a. Alternatively, inhibitors preventing correct function of CDKN1a and/or CDKN2a may be used.

Ligands

After a cell population comprising at least one bona fide pancreatic progenitor cell has been provided, said population is exposed to a first ligand which binds to a first marker specific for PDX1− cells and the cells that do not bind to said first ligand are selected. This negative separation results in a cell population enriched for PDX1+ cells. The cell population is exposed to a second ligand which binds a marker specific for PDX1+ cells and/or to a third ligand binding a third marker specific for PDX1+ NKX6-1+ cells and the cells binding to the second and/or third ligand are selected. It will be understood that exposure to each of the first and second and/or third ligand can be performed simultaneously or in separate steps.

Accordingly, in one embodiment, the cell population is exposed to a first ligand which binds to a first marker specific for PDX1− cells. After the cells that do not bind to the first ligand have been selected, the cell population, now enriched for PDX1+ cells, is exposed to a second ligand which binds a marker specific for PDX1+ cells and/or to a third ligand binding a third marker specific for PDX1+ NKX6-1+ cells and the cells binding to the second and/or third ligand are selected.

In another embodiment, the cell population is exposed to the first ligand, to the second ligand and/or to the third ligand simultaneously, and the cells that do not bind the first ligand but that bind to the second and/or third ligand are selected.

Each of the ligands disclosed herein is a moiety that specifically binds or cross-reacts to a marker, i.e. a marker specific for PDX1+ cells, PDX1− cells or PDX1+ NKX6-1+ cells. The term 'ligand' or 'ligands' will be used as a generic term to refer to any of the first, second or third ligand.

The ligand may be an antibody or a fragment thereof, wherein the antibody or fragment thereof is capable of recognising and binding a marker specific for a certain type of cells. The antibody may be monoclonal or polyclonal. Thus in some embodiments, at least one of the first, second and third ligands is a monoclonal or polyclonal antibody or fragment thereof. In other embodiments, at least two of the first, second and third ligands are monoclonal or polyclonal antibodies or fragments thereof. In other embodiments, the first, second and third ligands are monoclonal or polyclonal antibodies or fragments thereof.

In some embodiments, the marker to which the ligand binds is a cell surface marker.

The ligands and/or antibodies employed in the embodiments described herein may in some embodiments be associated with detectable labels. Hence, as used herein, the term "label" or "detectable label" refers to, for example, radioactive, fluorescent, luminescent, chemiluminescent, biological or enzymatic tags or labels of standard use in the art. Detectable labels for attachment to components useful in certain embodiments described herein can be easily selected from among numerous compositions known and readily available to one skilled in the art of diagnostic assays. In some embodiments, the label can be a small chemical molecule that is capable, acting alone, or in concert with other molecules or proteins, of providing a signal, that is detectable either directly or indirectly. In preferred embodiments, the marker or target is associated with the various ligands or competing analytes used in the assays. The reagents, ligands, competing analytes, or capture medium described herein are not limited by the particular detectable label or label system employed. In some cases, the detectable label can include the refractive index of a cell surface or bead. A detectable label can be conjugated, or otherwise bound, to nucleic acids, polypeptides, such as antibodies, or small molecules. For example, oligonucleotides described herein can be labeled subsequent to synthesis, by incorporating biotinylated dNTPs or rNTP, or some similar means (e.g., photo-cross-linking a protein derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythirin, rhodamine, Cy2, Cy3, Cy3.5, Cy5, Cy5.5, Cy7, FluorX and others, can be attached to nucleic acids. Non-limiting examples of detectable labels that can be conjugated to polypeptides such as antibodies include but are not limited to radioactive labels, such as $^{3}$H, $^{11}$C, $^{14}$C, $^{18}$F, $^{32}$P, $^{35}$S, $^{64}$Cu, $^{76}$Br, $^{86}$Y, $^{99}$Tc, $^{111}$In, $^{123}$I, $^{125}$I, or $^{177}$Lu, enzymes, such as horseradish peroxidase, fluorophores, chromophores, chemiluminescent agents, chelating complexes, dyes, colloidal gold or latex particles.

In one embodiment, particular labels enable detection by emitting a detectable signal of a particular wavelength upon excitation by a laser. Phycobiliproteins, tandem dyes, certain fluorescent proteins, small chemical molecules, and certain molecules detectable by other means can all be considered labels for flow cytometry analyses. See, e.g., the labels listed in Handbook of Fluorescent Probes and Research Chemicals, 6th Ed., R. P. Haugland, Molecular Probes, Inc., Eugene, Oreg. (1996). A ligand such as an antibody molecule, for example, directly labeled by conjugation with a biliprotein can have as many as 34 associated chromophores, each with an absorbance and quantum yield roughly comparable to those of fluorescein. Examples of biliproteins useful in the certain embodiments described herein are phycocyanin, allophycocyanin (APC), allophycocyanin B, phycoerythrin and preferably R-phycoerythrin. Phycoerythrin (PE) is among the brightest fluorescent dyes currently available.

Still other labels that can be directly conjugated to the components of the certain methods described herein or used with the biliproteins or tandem dyes to add additional numbers of labeled ligands to the method include small molecules that upon excitation emit wavelengths of less than 550 nm. Hence, as used herein, a "small molecule" label or equivalents thereof refers to such molecules do not overlap with the emissions of the biliproteins. One example of such a marker is fluorescein isothiocyanate (FITC). Still other labels that can be employed in this method to provide additional colors are the proteins known as the green fluorescent proteins (GFPs) and blue fluorescent proteins (BFPs); also, in certain embodiments, labels that emit upon excitation by ultraviolet light are useful.

A detectable label can also be an enzyme that interacts with a substrate to produce the detectable signal; or a protein that is detectable by antibody binding or by binding to a suitably labeled ligand. A variety of enzyme systems operate to reveal a colorimetric signal in an assay, for example, glucose oxidase, horseradish peroxidase (FIRP) or alkaline phosphatase (AP), and hexokinase in conjunction with glucose-6-phosphate dehydrogenase that reacts with ATP, glucose, and NAD+ to yield NADH that is detected as increased absorbance at 340 nm wavelength. Still additional labels such as colored latex microparticles whereby a dye is embedded and forms conjugates with an inhibitor sequence or ligand and provide a visual signal indicative of the presence of the resulting complex can be applicable for some assays described in certain embodiments. Other label systems that can be used include nanoparticles or quantum dots. Thus, any number of additional, and conventionally employed, labeling systems can be adapted to the methods described herein. One of skill in the art understands that selection and/or implementation of a label system involves only routine experimentation. The labels and markers discussed above can be obtained commercially from known sources.

As used herein, a "solid matrix" or a "solid phase capture medium" refers to any matrix or medium which allows it to be separated from the cell population sample, for example, a physiologically compatible bead. Characteristics of such a matrix or medium include refractive index, size, light scatter intensity, or carrying a fluorescent detector dye to provide a unique fluorescent signature. Such beads are conventionally available in the art. For example, one subset of solid phase capture medium includes stable colloidal particles, such as polystyrene beads ranging in size from between about 0.2 to about 5.0 μm in diameter (i.e., colloidal-sized). Such polystyrene substrates or beads can contain aldehyde and/or sulfate functional groups, such as the commercially available beads.

First Ligand

The present method for isolating a population enriched for bona fide pancreatic progenitor cell comprises the steps of:
  i) providing a cell population comprising at least one bona fide pancreatic progenitor cell, wherein the bona fide pancreatic progenitor cell expresses PDX1 and NKX6-1; and
  ii) exposing said cell population to:
    a) a first ligand which binds to a first marker specific for PDX1− cells and selecting the cells that do not bind to said first ligand from said cell population, thereby enriching the cell population for PDX1+ cells; and/or
    b) a second ligand which binds to a second marker specific for PDX1+ cells and selecting the cells that bind to said second ligand from the cells that do not bind to said second ligand, thereby enriching the cell population for PDX1+ cells; and/or
    c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
  thereby obtaining a cell population enriched for bona fide pancreatic progenitor cells.

Accordingly, after providing a cell population comprising at least one bona fide pancreatic progenitor cell, wherein the bona fide pancreatic progenitor cell expresses PDX1 and NKX6-1, the cell population is exposed to a first ligand which binds a first marker specific for PDX1− cells and the cells that do not bind to said first ligand are selected, thereby enriching for PDX1-expressing (PDX1+) cells.

The first ligand can be a ligand as described above. In some embodiments, the first ligand is a ligand capable of recognising and binding a cell surface marker. In some embodiments, the cell surface marker is CD49d. In some embodiments, the first ligand is a monoclonal or polyclonal antibody or fragment thereof directed against CD49d. The first ligand may be conjugated to a label, for example in order to facilitate selection of the cells that do not bind to the first ligand, as detailed above.

Selection of the cells that do not bind to the first ligand may be performed by methods known in the art such as flow cytometry. Accordingly, in some embodiments, expression of the first marker may be detected by flow cytometry.

Second Ligand

The method further comprises the step of exposing the starting population (or the cells that do not express PDX1 after selection with a first ligand as described above) to a second ligand which binds to a second marker specific for PDX1+ cells and selecting the cells that bind to said second ligand from the cells that do not bind to said second ligand, thereby obtaining a cell population enriched for PDX1+ cells. As a result, a population enriched for bona fide pancreatic progenitor is obtained. The enriched population may in particular be enriched for posterior foregut PDX1+ cells.

The second ligand can be a ligand as described above. In some embodiments, the second ligand is a ligand capable of recognising and binding a cell surface marker. In some embodiments, the second ligand can recognise and bind to a second target selected from the group consisting of FOLR1, CDH1/ECAD, F3/CD142, PDX1, FOXA2, EPCAM, HES1, and GATA4. In some embodiments, the second ligand is a monoclonal or polyclonal antibody or fragment thereof directed against a second target selected from the group consisting of FOLR1, CDH1/ECAD, F3/CD142, PDX1, FOXA2, EPCAM, HES1, and GATA4. The second ligand may be conjugated to a label, for example in order to facilitate selection of the cells that bind to the second ligand, as detailed above. In a preferred embodiment, the second ligand is capable of recognising and binding to FOLR1.

Selection of the cells that bind to the second ligand may be performed by methods known in the art such as flow cytometry. Accordingly, in some embodiments, expression of the second marker may be detected by flow cytometry.

Exposure of the cell population to the second ligand may occur at the same time as exposure to the first ligand and optionally to the third ligand, or it may occur in a separate step.

Third Ligand

The method may comprise the step of exposing the cell population to a third ligand which binds to a third marker specific for PDX1+ NKX6-1+ cells and the cells that bind to said third ligand are selected, in order to obtain a cell population enriched for bona fide pancreatic progenitor cells expressing both PDX1 and NKX6-1. Exposure to the third ligand may be performed instead of exposure to the second ligand. In some embodiments, the cell population is exposed to the first and third ligand, where the exposure to the ligands can occur simultaneously or in separate steps. In other embodiments, the cell population is exposed to the first, the second and the third ligand, where the exposure to the ligands can occur simultaneously or in separate steps. As a result, a population enriched for bona fide pancreatic progenitor cells is obtained.

The third ligand can be a ligand as described above. In some embodiments, the third ligand is a ligand capable of recognising and binding a cell surface marker. In some embodiments, the third ligand can recognise and bind to a third target, where the third target is selected from the group consisting of GP2, SCN9A, MPZ, NAALADL2, KCNIP1, CALB1, SOX9, NKX6-2, and NKX6-1. In a preferred embodiment, the third target is GP2. In some embodiments, the third ligand is a monoclonal or polyclonal antibody or fragment thereof directed against a third target selected from the group consisting of GP2, SCN9A, MPZ, NAALADL2, KCNIP1, CALB1, SOX9, NKX6.2 and NKX6-1. In a preferred embodiment, the third ligand is a monoclonal or polyclonal antibody or fragment thereof directed against GP2. The third ligand may be conjugated to a label, for example in order to facilitate selection of the cells that bind to the third ligand, as detailed above.

Selection of the cells that bind to the third ligand may be performed by methods known in the art such as flow cytometry. Accordingly, in some embodiments, expression of the third marker may be detected by flow cytometry.

Accordingly, in some embodiments, the present method for isolating a population enriched for bona fide pancreatic progenitor cell comprises the steps of:
  i) providing a cell population comprising at least one bona fide pancreatic progenitor cell, wherein the bona fide pancreatic progenitor cell expresses PDX1 and NKX6-1; and
  ii) exposing said cell population to:
    a) a first ligand which binds to a first marker specific for PDX1− cells and selecting the cells that do not bind to said first ligand from said cell population, thereby enriching the cell population for PDX1+ cells; and/or
    b) a second ligand which binds to a second marker specific for PDX1+ cells and selecting the cells that bind to said second ligand from the cells that do not bind to said second ligand, thereby enriching the cell population for PDX1+ cells;
and/or
c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
wherein
the first ligand recognises and binds to CD49d,
the second ligand recognises and binds to a second marker selected from the group consisting of FOLR1, CDH1/ECAD, F3/CD142, PDX1, FOXA2, EPCAM, HES1, and GATA4, and
the third ligand recognises and binds to a third marker selected from the group consisting of GP2, SCN9A, MPZ, NAALADL2, KCNIP1, CALB1, SOX9, NKX6.2 and NKX6-1,
thereby obtaining a cell population enriched for bona fide pancreatic progenitor cells.

In some embodiments, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) exposing said cell population to:
a) a first ligand which binds to a first marker specific for PDX1− cells and selecting the cells that do not bind to said first ligand from said cell population, thereby enriching the cell population for PDX1+ cells; and
b) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
wherein
the first ligand recognises and binds to CD49d, and
the third ligand recognises and binds to a third marker selected from the group consisting of GP2, SCN9A, MPZ, NAALADL2, KCNIP1, CALB1, SOX9, NKX6.2 and NKX6-1,
thereby obtaining a cell population enriched for bona fide pancreatic progenitor cells.

Thus, in some embodiments, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) exposing said cell population to:
a) a first ligand which binds to a first marker specific for PDX1− cells and selecting the cells that do not bind to said first ligand from said cell population, thereby enriching the cell population for PDX1+ cells; and
b) a second ligand which binds to a second marker specific for PDX1+ cells and selecting the cells that bind to said second ligand from the cells that do not bind to said second ligand, thereby enriching the cell population for PDX1+ cells;
wherein
the first ligand recognises and binds to CD49d, and
the second ligand recognises and binds to a second marker selected from the group consisting of FOLR1, CDH1/ECAD, F3/CD142, PDX1, FOXA2, EPCAM, HES1, and GATA4,
thereby obtaining a cell population enriched for bona fide pancreatic progenitor cells. Thus, in some embodiments, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) exposing said cell population to:
a) a first ligand which binds to a first marker specific for PDX1− cells and selecting the cells that do not bind to said first ligand from said cell population, thereby enriching the cell population for PDX1+ cells;
b) a second ligand which binds to a second marker specific for PDX1+ cells and selecting the cells that bind to said second ligand from the cells that do not bind to said second ligand, thereby enriching the cell population for PDX1+ cells;
and
c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
wherein
the first ligand recognises and binds to CD49d,
the second ligand recognises and binds to FOLR1, and
the third ligand recognises and binds to GP2,
thereby obtaining a cell population enriched for bona fide pancreatic progenitor cells.

In some embodiments, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) exposing said cell population to:
a) a first ligand which binds to a first marker specific for PDX1− cells and selecting the cells that do not bind to said first ligand from said cell population, thereby enriching the cell population for PDX1+ cells; and
b) a second ligand which binds to a second marker specific for PDX1+ cells and selecting the cells that bind to said second ligand from the cells that do not bind to said second ligand, thereby enriching the cell population for PDX1+ cells;
wherein
the first ligand recognises and binds to CD49d,
the second ligand recognises and binds to FOLR1,
thereby obtaining a cell population enriched for bona fide pancreatic progenitor cells.

In some embodiments, the present method for isolating a population enriched for bona fide pancreatic progenitor cell comprises the steps of:
i) providing a cell population comprising at least one bona fide pancreatic progenitor cell, wherein the bona fide pancreatic progenitor cell expresses PDX1 and NKX6-1; and
ii) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
wherein
the third ligand recognises and binds to GP2,
thereby obtaining a cell population enriched for bona fide pancreatic progenitor cells.

In some embodiments, the present method for isolating a population enriched for bona fide pancreatic progenitor cell comprises the steps of:
  i) providing a cell population comprising at least one bona fide pancreatic progenitor cell, wherein the bona fide pancreatic progenitor cell expresses PDX1 and NKX6-1; and
  ii) exposing said cell population to a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
wherein the third ligand recognises and binds to GP2,
thereby obtaining a cell population enriched for bona fide pancreatic progenitor cells.

In some embodiments, the present method for isolating a population enriched for bona fide pancreatic progenitor cell comprises the steps of:
  i) providing a cell population comprising at least one bona fide pancreatic progenitor cell, wherein the bona fide pancreatic progenitor cell expresses PDX1 and NKX6-1; and
  ii) exposing said cell population to:
    a) a second ligand which binds to a second marker specific for PDX1+ cells and selecting the cells that bind to said second ligand from the cells that do not bind to said second ligand, thereby enriching the cell population for PDX1+ cells; and
    b) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
  wherein
  the second ligand recognises and binds to FOLR1,
  the third ligand recognises and binds to GP2,
thereby obtaining a cell population enriched for bona fide pancreatic progenitor cells.

It will be understood that methods for generating hormone producing beta cells such as insulin-producing beta cells include sorting GP2 positive cells isolated by flow cytometry or other similar methods and treated with Forskolin, Alk5 inhibitor, Noggin, Nicotinamide. Rock inhibitor may be added for 24-48 h after the sorting.

Bona Fide Pancreatic Progenitor Cell Population

The present methods provide a population enriched for bona fide pancreatic progenitor cells.

In one embodiment, at least one cell of the cell population enriched for bona fide pancreatic progenitor cells has the capability to differentiate further. The at least one cell of the cell population enriched for bona fide pancreatic progenitor cells may have the capability to differentiate further into pancreatic hormone-producing cells. In some embodiments, at least one of the pancreatic hormone-producing cells is an insulin-producing cell. In some embodiments, at least one of the pancreatic hormone-producing cells is responsive to glucose. In some embodiments, at least one of the pancreatic hormone-producing cells is an insulin-producing cell, which is also responsive to glucose. In some embodiments, at least one cell of the cell population enriched for bona fide pancreatic progenitor cells can produce insulin-producing islet cells.

In some embodiments, the at least one of the pancreatic hormone-producing cells has increased expression of at least one of insulin, C-peptide, Insm-1, Isl-1, MafA and MafB compared to a cell population that has been incubated in the absence of the Yap1 inhibitor. In one embodiment, the pancreatic hormone-producing cell is a mature β cell.

Another method for obtaining hormone-producing β-cells such as insulin-producing β-cells comprises the step of treating the cells isolated by the present methods with a Yap1 inhibitor, such as verteporfin. Such methods are described in the co-pending patent application entitled "Method for production of insulin-producing cells" (inventors Anant Mamidi and Henrik Semb, applicant: University of Copenhagen) filed on the same date.

YAP1 (Yes-associated protein 1) is a downstream nuclear effector of the Hippo signalling pathway, which is involved in development, growth, repair, and homeostasis. Verteporfin is a small molecule, which is capable of inhibiting Yap1 activity.

After a pancreatic progenitor cell population comprising at least one cell capable of differentiation has been provided as described above, the cell population can be incubated in the presence of a Yap1 inhibitor. In some embodiments, the Yap1 inhibitor is verteporfin.

In some embodiments, the cell population is incubated in the presence of verteporfin at a concentration of between 0.1 and 10 μg/mL, such as between 0.2 and 9 μg/mL, such as between 0.3 and 8 μg/mL, such as between 0.4 and 7 μg/mL, such as between 0.5 and 6 μg/mL, such as between 0.6 and 5 μg/mL, such as between 0.7 and 4 μg/mL, such as between 0.8 and 3 μg/mL, such as between 0.9 and 2 μg/mL, such as 1 μg/mL. In one embodiment, the cell population is incubated in the presence of 1 μg/mL verteporfin.

In some embodiments, the cell population is incubated in the presence of verteporfin for a duration of at least 3 days, such as at least 4 days, such as at least 5 days, such as at least 6 days, such as at least 7 days, such as at least 8 days, such as at least 9 days, such as at least 10 days. In some embodiments, the incubation in the presence of verteporfin is performed for a duration of 5 days.

In some embodiments, CDKN1a and/or CDKN2a is inactivated in the starting cell population. In one embodiment, CDKN1a is inactivated. In another embodiment, CDKN2a is inactivated. In another embodiment, CDKN1a and CDKN2a are both inactivated. In another embodiment, CDKN1a and CDKN2 are inactivated sequentially, i.e. one of CDKN1a and CDKN2a is inactivated in a first step, and the other of CDKN1a and CDKN2a is inactivated in a second step; the first and second steps may overlap in time or be independent.

Method for Producing a Cell Population Enriched for Bona Fide Pancreatic Progenitor Cells Also disclosed herein is a method for producing a cell population enriched for bona fide pancreatic progenitor cells, said enriched cell population comprising at least 70% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells. In one embodiment, the method is as described above.

Thus in some embodiments, the method is for producing a cell population enriched for bona fide pancreatic progenitor cells comprising at least 70% bona fide pancreatic progenitor cells, such as at least 71% bona fide pancreatic progenitor cells, such as at least 72% bona fide pancreatic progenitor cells, such as at least 73% bona fide pancreatic progenitor cells, such as at least 74% bona fide pancreatic progenitor cells, such as at least 75% bona fide pancreatic progenitor cells, such as at least 76% bona fide pancreatic progenitor cells, such as at least 77% bona fide pancreatic progenitor cells, such as at least 78% bona fide pancreatic progenitor cells, such as at least 79% bona fide pancreatic progenitor cells, such as at least 80% bona fide pancreatic progenitor cells, such as at least 81% bona fide pancreatic progenitor cells, such as at least 82% bona fide pancreatic progenitor cells, such as at least 83% bona fide pancreatic progenitor cells, such as at least 84% bona fide pancreatic progenitor cells, such as at least 85% bona fide pancreatic progenitor cells, such as at least 86% bona fide pancreatic progenitor cells, such as at least 87% bona fide pancreatic progenitor cells, such as at least 88% bona fide pancreatic progenitor cells, such as at least 89% bona fide pancreatic progenitor cells, such as at least 90% bona fide pancreatic progenitor cells.

In order to determine the fraction of bona fide progenitor cells comprised in the enriched population, methods known in the art can be employed, such as, but not limited to, immunostaining and/or flow cytometry methods.

Cell Population Enriched for Bona Fide Pancreatic Progenitor Cells

Also disclosed herein is a cell population comprising at least 70% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells. In some embodiments, the cell population is obtainable by any of the methods described above.

Thus in some embodiments, the cell population enriched for bona fide pancreatic progenitor cells comprises at least 70% bona fide pancreatic progenitor cells, such as at least 71% bona fide pancreatic progenitor cells, such as at least 72% bona fide pancreatic progenitor cells, such as at least 73% bona fide pancreatic progenitor cells, such as at least 74% bona fide pancreatic progenitor cells, such as at least 75% bona fide pancreatic progenitor cells, such as at least 76% bona fide pancreatic progenitor cells, such as at least 77% bona fide pancreatic progenitor cells, such as at least 78% bona fide pancreatic progenitor cells, such as at least 79% bona fide pancreatic progenitor cells, such as at least 80% bona fide pancreatic progenitor cells, such as at least 81% bona fide pancreatic progenitor cells, such as at least 82% bona fide pancreatic progenitor cells, such as at least 83% bona fide pancreatic progenitor cells, such as at least 84% bona fide pancreatic progenitor cells, such as at least 85% bona fide pancreatic progenitor cells, such as at least 86% bona fide pancreatic progenitor cells, such as at least 87% bona fide pancreatic progenitor cells, such as at least 88% bona fide pancreatic progenitor cells, such as at least 89% bona fide pancreatic progenitor cells, such as at least 90% bona fide pancreatic progenitor cells.

In order to determine the fraction of bona fide progenitor cells comprised in the enriched population, methods known in the art can be employed, such as, but not limited to, immunostaining and/or flow cytometry methods.

Treatment of Metabolic Disorder

Also disclosed herein is a cell population comprising bona fide pancreatic progenitor cells, obtainable any of the methods disclosed herein, for treatment of a metabolic disorder in an individual in need thereof.

The cell populations described herein can be used for treatment of metabolic disorders. Such cell populations comprising bona fide pancreatic progenitor cells can be enriched for bona bide progenitors as described, such that a cell population enriched in e.g. β-cell progenitors can be isolated. This can be done as described above, for example by the use of ligands binding markers as detailed above and isolation by flow cytometry. These isolated cells can be stored prior to use, or they can be used immediately. The cells may be differentiated further. Once a cell population with the desired characteristics is obtained, the cells are transplanted into an individual in need thereof. As an example, such cell-based therapy is useful for transplanting insulin-producing β-cells in individuals suffering from diabetes, whereby insulin production may be restored in vivo. If the starting cell population is derived from the patient him/herself, the risks of adverse immune reactions such as rejection of the transplanted cells may be reduced. As an alternative to transplanting insulin-producing β-cells into a patient, bona fide pancreatic progenitor cells, such as the cells obtainable by the methods described herein, can also be transplanted.

The term 'metabolic disorder' as used herein shall be construed to refer to endocrine, nutritional and metabolic diseases. Preferably, the disorder is related to a pancreatic disorder. Examples of metabolic disorders are: diabetes mellitus, including type 1 and type 2 diabetes.

Diabetes mellitus, commonly referred to as diabetes, is a group of metabolic diseases in which there are high blood sugar levels over a prolonged period. Several types of diabetes exist, including type 1 diabetes, type 2 diabetes and gestational diabetes. Type 1 diabetes is characterized by loss of the insulin-producing (3 cells of the islets of Langerhans in the pancreas, leading to insulin deficiency. Type 2 diabetes is characterized by insulin resistance, which may be combined with relatively reduced insulin secretion. The defective responsiveness of body tissues to insulin is believed to involve the insulin receptor. Gestational diabetes, which resembles type 2 diabetes, occurs in about 2-10% of all pregnancies. The type of diabetes can also be classified as insulin-dependent diabetes mellitus, non-insulin dependent diabetes mellitus, malnutrition-related diabetes mellitus or unspecified diabetes mellitus.

The methods disclosed herein can be used to obtain a cell population enriched for bona fide pancreatic progenitor cells. Accordingly, in some embodiments there is provided a cell population for treatment of a metabolic disorder in an individual in need thereof. In some embodiments, the metabolic disorder is selected from the group consisting of diabetes mellitus such as insulin-dependent diabetes mellitus, non-insulin dependent diabetes mellitus, malnutrition-related diabetes mellitus or unspecified diabetes mellitus.

In some embodiments, the cell population for treatment of a metabolic disorder is obtained by the methods described above, namely:

exposing a cell population comprising at least one bona fide pancreatic progenitor cell, wherein the bona fide pancreatic progenitor cell expresses PDX1 and NKX6-1, to a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells; wherein the third ligand recognises and binds to GP2; or exposing a cell population comprising at least one bona fide pancreatic progenitor cell, wherein the bona fide pancreatic progenitor cell expresses PDX1 and NKX6-

1, to a second ligand which binds to a second marker specific for PDX1+ cells and selecting the cells that bind to said second ligand from the cells that do not bind to said second ligand, thereby enriching the cell population for PDX1+ cells and to a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells, wherein the second ligand recognises and binds to FOLR1, and the third ligand recognises and binds to GP2; or exposing a cell population comprising at least one bona fide pancreatic progenitor cell, wherein the bona fide pancreatic progenitor cell expresses PDX1 and NKX6-1, to a first ligand which binds to a first marker specific for PDX1− cells and selecting the cells that do not bind to said first ligand from said cell population, thereby enriching the cell population for PDX1+ cells; and to a second ligand which binds to a second marker specific for PDX1+ cells and selecting the cells that bind to said second ligand from the cells that do not bind to said second ligand, thereby enriching the cell population for PDX1+ cells; and to a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells, wherein the first ligand recognises and binds to CD49d, the second ligand recognises and binds to FOLR1, and the third ligand recognises and binds to GP2;

or any of the methods described herein elsewhere.

In one aspect is provided a method of treatment of a metabolic disorder in an individual in need thereof, wherein the method comprises a step of providing a cell population enriched in bona fide pancreatic progenitor cells obtainable by the methods described herein.

In some embodiments, the present methods comprise a step of transplanting at least part of said enriched cell population into the individual suffering from a metabolic disorder.

In some embodiments, the enriched cell population may be further differentiated prior to transplantation. Bona fide pancreatic progenitor cells may thus be further differentiated into insulin-producing cells or to mature insulin-producing β-cells prior to transplantation, for example as described in the co-pending patent application entitled "Method for production of insulin-producing cells" (inventors Anant Mamidi and Henrik Semb, applicant: University of Copenhagen) filed on the same date. In other embodiments, the enriched cell population is further differentiated into endocrine cells found in the pancreatic islets. In some embodiments, the enriched cell population is further differentiated into insulin-producing β-cells having increased expression of MafA. Preferably, the insulin-producing β-cells are mature and/or insulin responsive.

Methods for further differentiating the enriched cell population are available to the skilled person (Rezania et al., 2014). In one embodiment, the method comprises the steps of providing a pancreatic progenitor cell population comprising at least one cell capable of differentiation; and incubating said cell population in the presence of a Yap1 inhibitor;

thereby obtaining a cell population enriched for insulin-producing β-cells. In one embodiment, the Yap1 inhibitor is verteporfin.

After a pancreatic progenitor cell population comprising at least one cell capable of differentiation has been provided as described above, the cell population can be incubated in the presence of a Yap1 inhibitor. In some embodiments, the Yap1 inhibitor is verteporfin.

In some embodiments, the cell population is incubated in the presence of verteporfin at a concentration of between 0.1 and 10 µg/mL, such as between 0.2 and 9 µg/mL, such as between 0.3 and 8 µg/mL, such as between 0.4 and 7 µg/mL, such as between 0.5 and 6 µg/mL, such as between 0.6 and 5 µg/mL, such as between 0.7 and 4 µg/mL, such as between 0.8 and 3 µg/mL, such as between 0.9 and 2 µg/mL, such as 1 µg/mL. In one embodiment, the cell population is incubated in the presence of 1 µg/mL verteporfin.

In some embodiments, the cell population is incubated in the presence of verteporfin for a duration of at least 3 days, such as at least 4 days, such as at least 5 days, such as at least 6 days, such as at least 7 days, such as at least 8 days, such as at least 9 days, such as at least 10 days. In some embodiments, the incubation in the presence of verteporfin is performed for a duration of 5 days.

In some embodiments, the cells that have thus been further differentiated may be isolated. In some embodiments, the isolated cells or a cell population comprising the cells that have been further differentiated are transplanted into the individual suffering from a metabolic disorder.

EXAMPLES

Example 1

Introduction

Curing diabetes would require the prevention of autoimmune destruction of beta cells together with the restoration of the beta cell mass already destroyed. The treatment would either be regeneration or transplantation of the insulin producing cells. Due to their inherent pluripotency and theoretically unlimited supply, human embryonic stem cells (hESCs) have become an attractive source for beta cell replacement therapies. This strategy relies on overcoming the risk of teratoma formation after transplantation. Engraftment of purified hESC derivatives could minimize the risk of tumorigenicity. In this study, we performed an in depth analysis of hESC-derived PDX1+ pancreatic progenitors by developing a targeted PDX1-eGFP reporter cell line. We identified novel cell surface markers for the isolation of hESC-derived PDX1+ beta cell progenitors. Specifically, we show enrichment of GP2 and FOLR1 in the GFP+ fraction corresponding to pancreatic progenitors and CD49d in the GFP− fraction. By combining these novel cell surface markers or using them individually, true beta cell progenitors can be isolated from heterogeneous cell populations derived during in vitro differentiation. These novel antibodies not only facilitate generation of insulin-producing cells from purified pancreatic progenitor cells, as well as further cultivation and transplantation of pure pancreatic progenitor cell populations for diabetes cell replacement therapy, but also enable further studies of human pancreas development.

Although functional glucose responsive insulin secreting cells have so far not been obtained through in vitro differentiation strategies, proof of principle have been obtained through transplantation of pancreatic progenitor cells and in vitro derived insulin expressing cells in diabetic mouse models, where the precursor cells/immature insulin+ cells differentiate and mature into glucose responsive insulin producing cells with the capacity to reverse diabetes in mice (Kroon et al. 2008, Rezania et al. 2014). This concept has become an attractive model for treatment of patients suffering from diabetes, as it offers an unlimited source of stem cell derived beta cells. However, before this vision can be realized two major concerns/obstacles have to be eliminated; (1) teratoma formation caused by transplantation of heterogeneous cell populations and (2) the implanted cells have to be protected to avoid subsequent immune rejection. It is shown/established that purification of pancreatic progenitor cells prior to transplantation could reduce the risk of teratoma formation. This enrichment can either be obtained through the use of tissue specific reporter cell lines or cell surface markers. Lack of available human reporter cell lines for isolation of pancreatic progenitors has hampered the identification of pancreas specific cell surface markers. The few publications relating to identification of human cell surface markers have made use of primary human pancreas or islet fractions as a source of material. In 2011, Kelly et al reported three cell surface markers for identification of pancreatic progenitors and endocrine cells by performing a flow cytometry-based screen of commercial antibodies. CD142 was identified as a surface marker for PDX1+/NKX6-1+ cells and CD200 or CD318 as surface markers for endocrine cells. Another group (Jiang et al 2011) reported an additional marker, CD24 to be a novel marker for PDX1+ progenitors. However, CD24 was later shown to be not a suitable marker for PDX1+ progenitors as its expression was detected in undifferentiated hESCs and during the differentiation process from early endoderm to pancreatic endoderm (Naujok and Lenzen, 2012). A widespread expression pattern for CD24 was also observed in the antibody screen performed by Kelly et al. Indeed, we examined the expression pattern of these published cell surface markers in our screen and could observe no significant change in expression between the GFP+ and GFP− cell fractions for the markers CD24, CD200. Additionally, CD318 was instead significantly enriched in the GFP− cells. While CD142/F3 was comparatively enriched in the GFP+ cells (relative to the GFP− cells) at transcript level, stainings with CD142 antibody showed CD142 expression in both GFP+ and GFP− cell populations. These observations highlight/illustrate the difficulties with identifying specific cell surface markers without the use of tissue specific reporter cell lines.

To enable the isolation of pure PDX1+ pancreatic progenitor cells from hESCs, we established a PDX1 reporter cell line by gene targeting. While this has been accomplished in mouse ES cells (Holland et al., 2006), this has so far not been published in hESCs. Furthermore, this reporter cell line not only allows the isolation and further characterization of hESC-derived pancreatic progenitors but also represents a novel tool for studying the development of human pancreatic progenitors.

In the present study, we identified GP2 as a novel cell surface marker for isolation of PDX1+/NKX6-1+ pancreatic progenitors, and CD49d as a cell surface marker for PDX1- cell fractions, allowing negative selection. An additional cell surface marker, FOLR1, was also identified. In contrast to GP2, this marker has a broader staining pattern, also labelling PDX1+/NKX6-1− progenitors.

These markers, in contrast to previously published markers, allow the enrichment of pancreatic progenitors from heterogeneous cell cultures and are extremely valuable for the development of diabetes therapies as they enable isolation of PDX1+ beta cell progenitors from other genetically untagged human ES cell lines.

Example 2—Targeting of eGFP into the Human PDX1 Locus

Figures 1B, 1C:
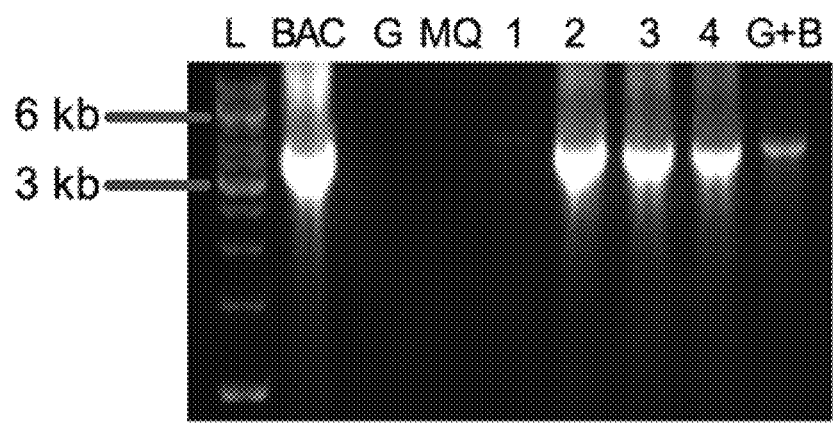
Figure 1D:
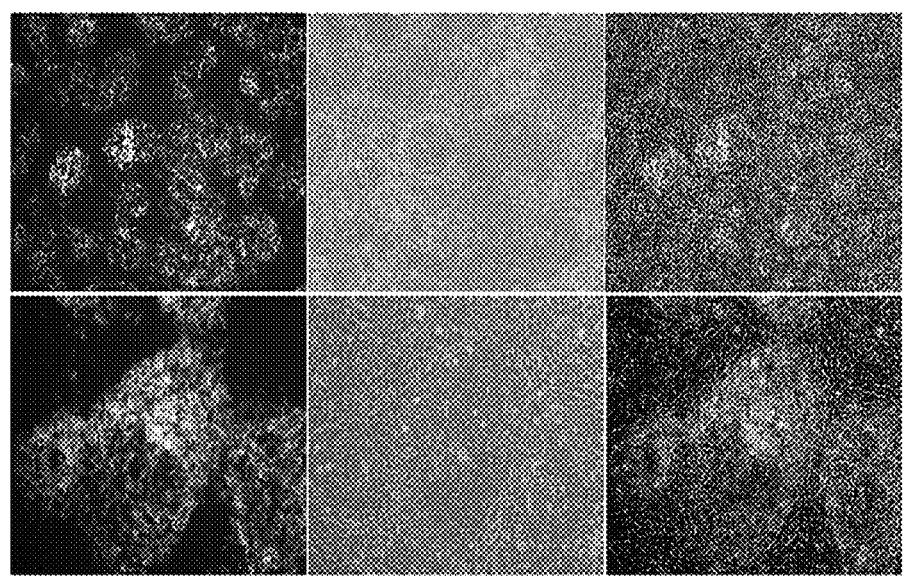
Figure 1E:
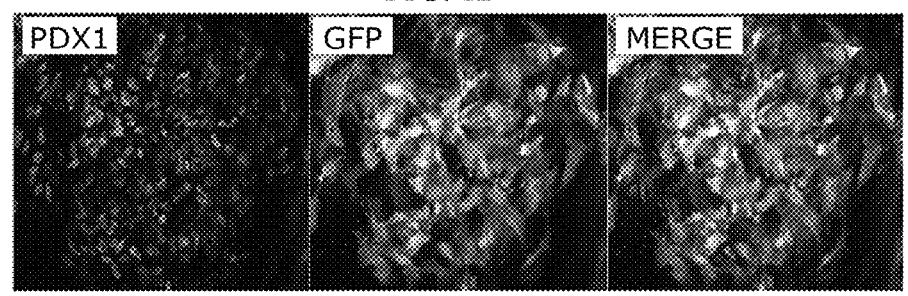
Figure 1F:
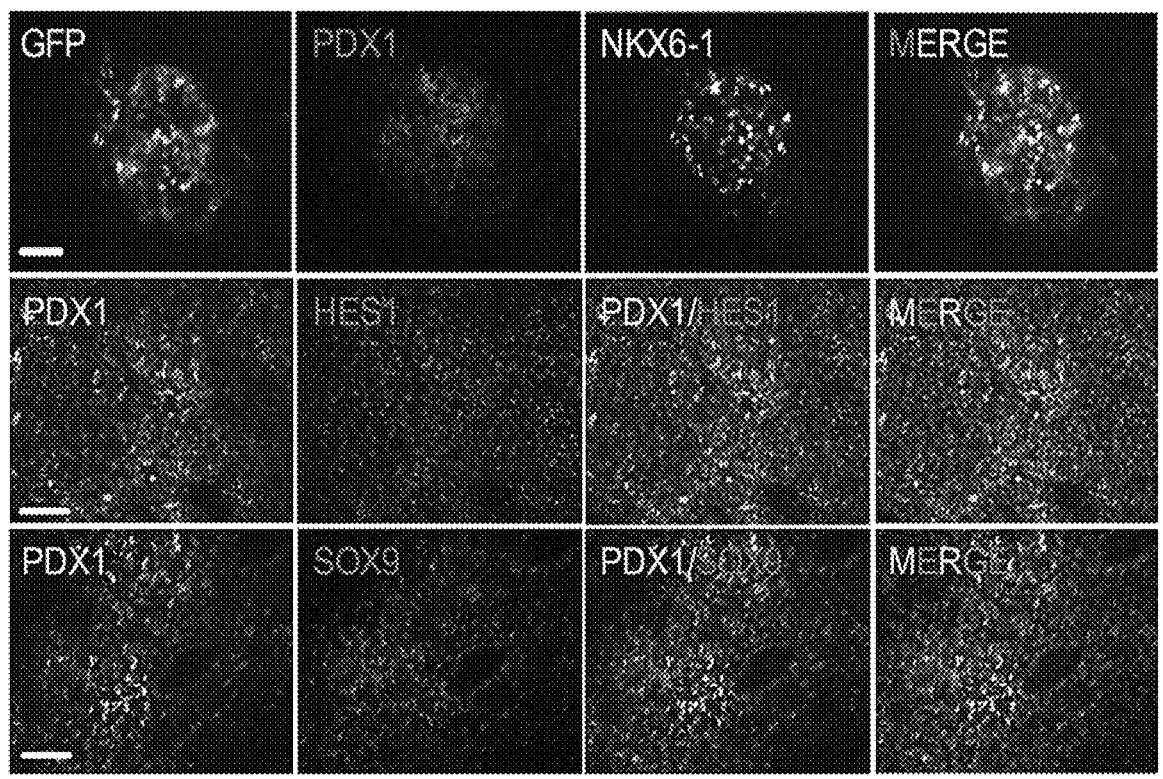

To monitor pancreatic endoderm formation in hESCs, the transcription factor Pancreatic duodenal homeobox 1 (PDX1), essential for pancreas development and beta cell function, was targeted by using bacterial artificial chromosome (BAC) recombineering (FIG. 1A). A BAC containing the human PDX1 gene was identified using the genome browser at http://genome.ucsc.edu. An eGFP-loxp-Sv40-Neo-loxp reporter cassette was inserted directly upstream of the PDX1 start codon. The targeting vector was retrieved into a bacterial plasmid and the neomycin cassette was excised by CRE recombinase to produce the final targeting vector containing homology arms of 12.5 kb and 3.5 kb. Notably, the excision of the Neo cassette was crucial to obtain eGFP expression. The HUES-4 cell line was electroporated with the linearized targeting vector and treated with G418 for two weeks until drug resistant colonies appeared. Screening of 353 clones resulted in 4 correctly targeted clones (FIGS. 1B and 1C). To confirm PDX1-eGFP expression in the targeted clone, we used a modified version of our previously published differentiation protocol (Ameri et al., 2010) (FIG. 1C). hESCs were exposed to Activin A and Wnt3a (used on hESCs cultured on MEFs) or Chir (used on hESCs cultured in ""DEF-CSTM" medium, Cellectis stem cells, Cellartis AB") to induce definitive endoderm induction (Stage 1). This stage was followed by addition of retinoid acid (RA) for three days (Stage 2) and then FGF2 (occasionally with Noggin) for remaining days to induce posterior foregut and pancreatic progenitors (Stage 3). Fluorescence and corresponding phase contrast images of the targeted PDX1-eGFP hES cell line at day 13 are shown in FIG. 1D. At day 17, 50-70% of the cells regularly express PDX1-eGFP. Immunostaining of clone PDXeG1 showed that eGFP was highly co-localized with PDX1 (FIG. 1E). These results confirm that the reporter cell line PDX1-eGFP can be used to monitor PDX1 expression during hESC differentiation. Immunostainings of stage 3 cells (d17) confirmed the expression of NKX6-1, ECAD, HES1 and SOX9 in the pancreatic progenitors at protein level (FIG. 2F).

Example 3—Analysis of In Vitro Differentiated PDX1-eGFP hESCs

Figure 2A:
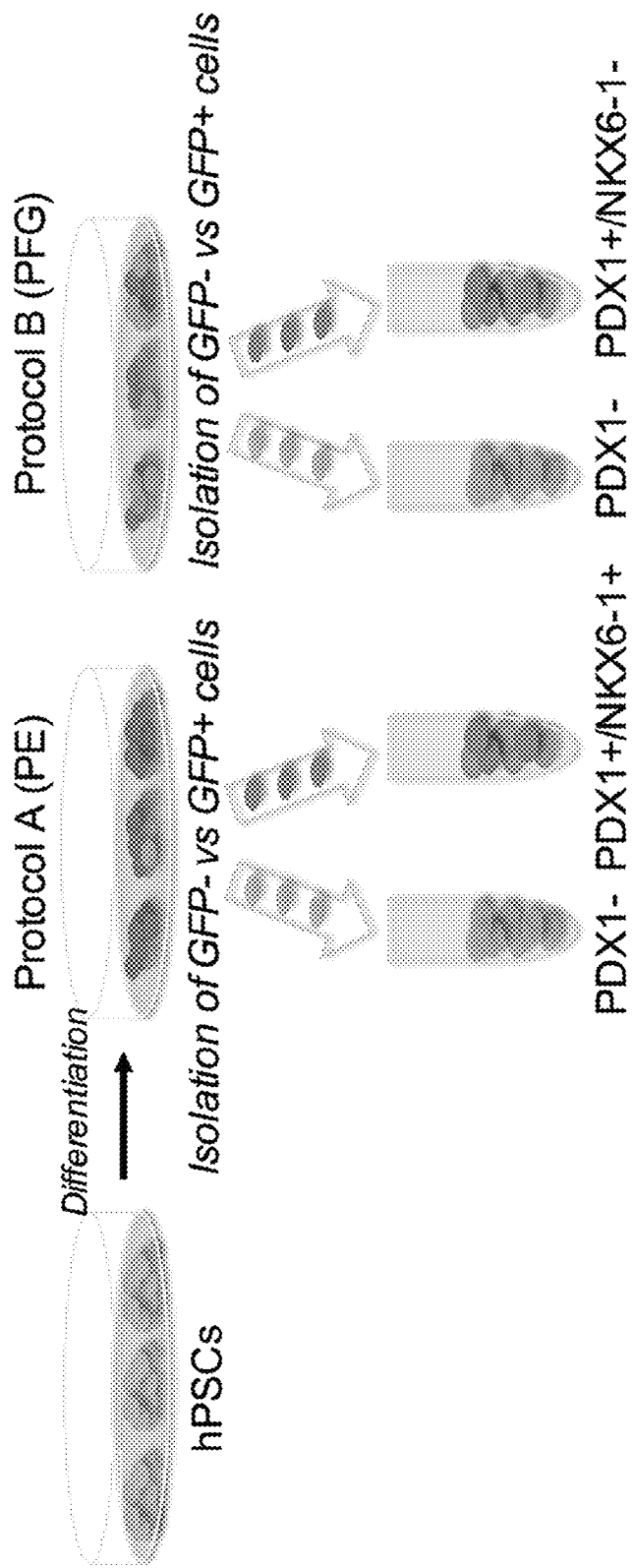
FIGS. 2A-2G. Analysis of in vitro differentiated PDX1-eGFP hPSCs.
Figures 2B, 2C:
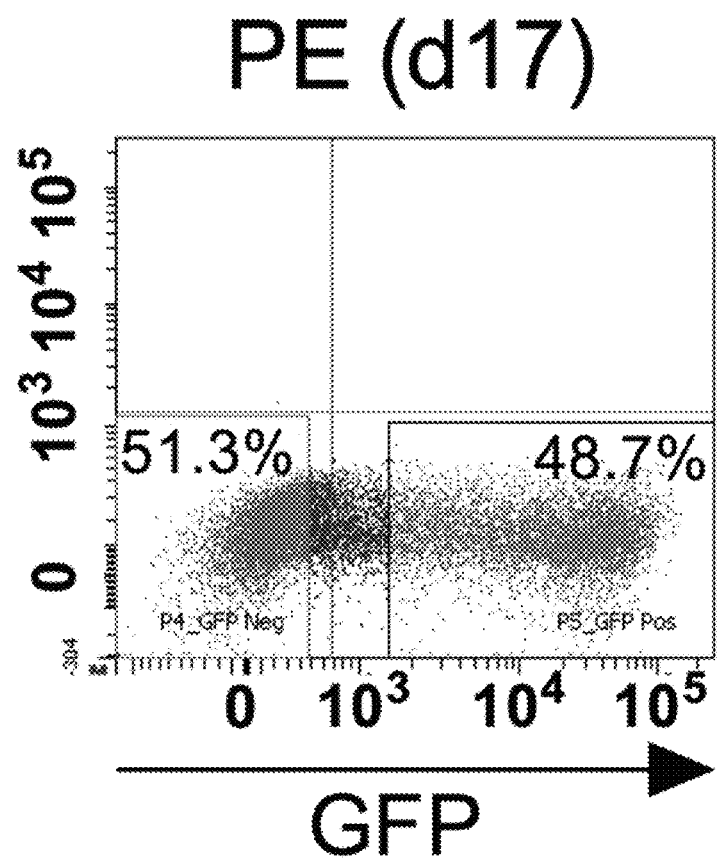
Figure 2D:
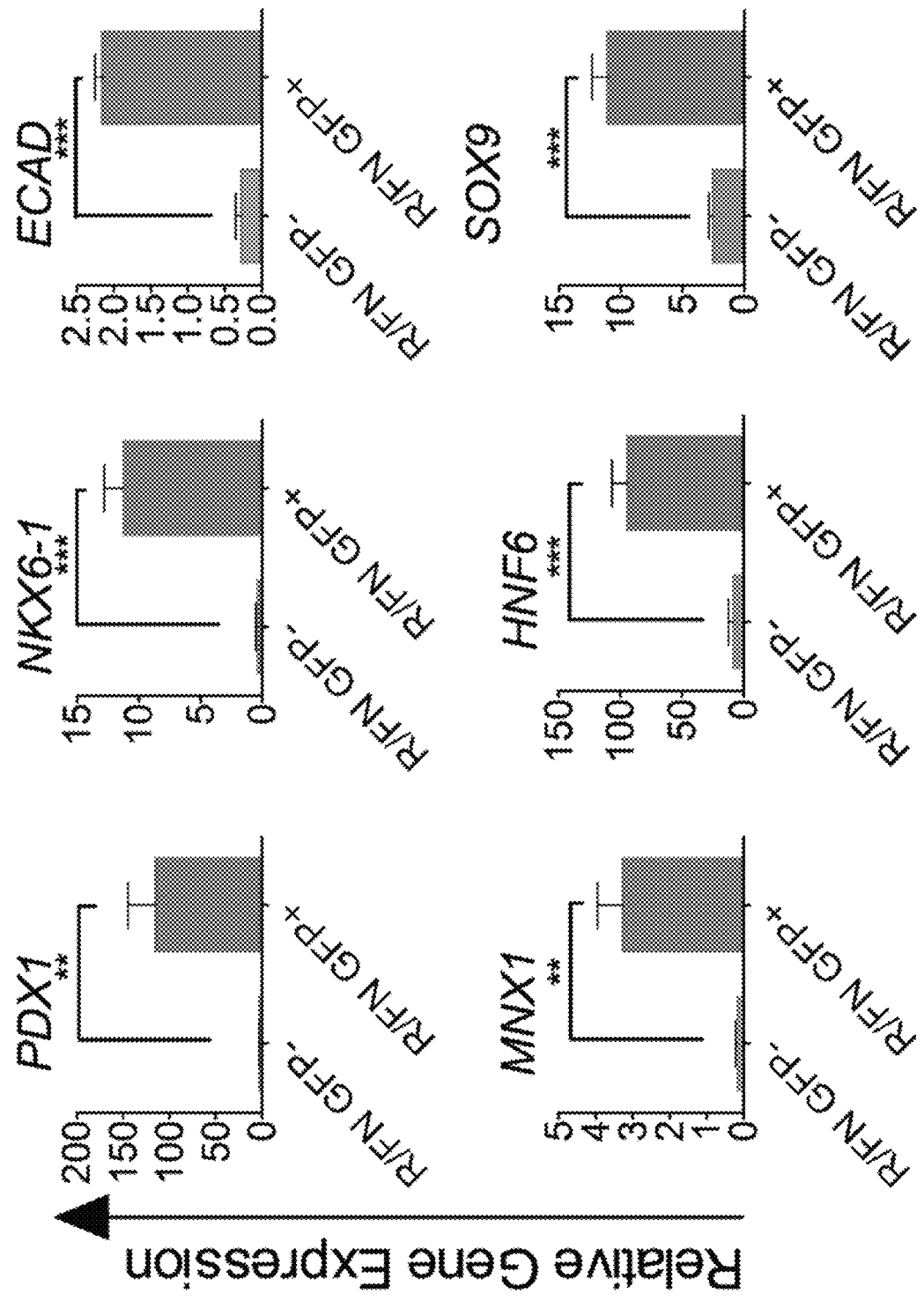
Figures 2E, 2F:
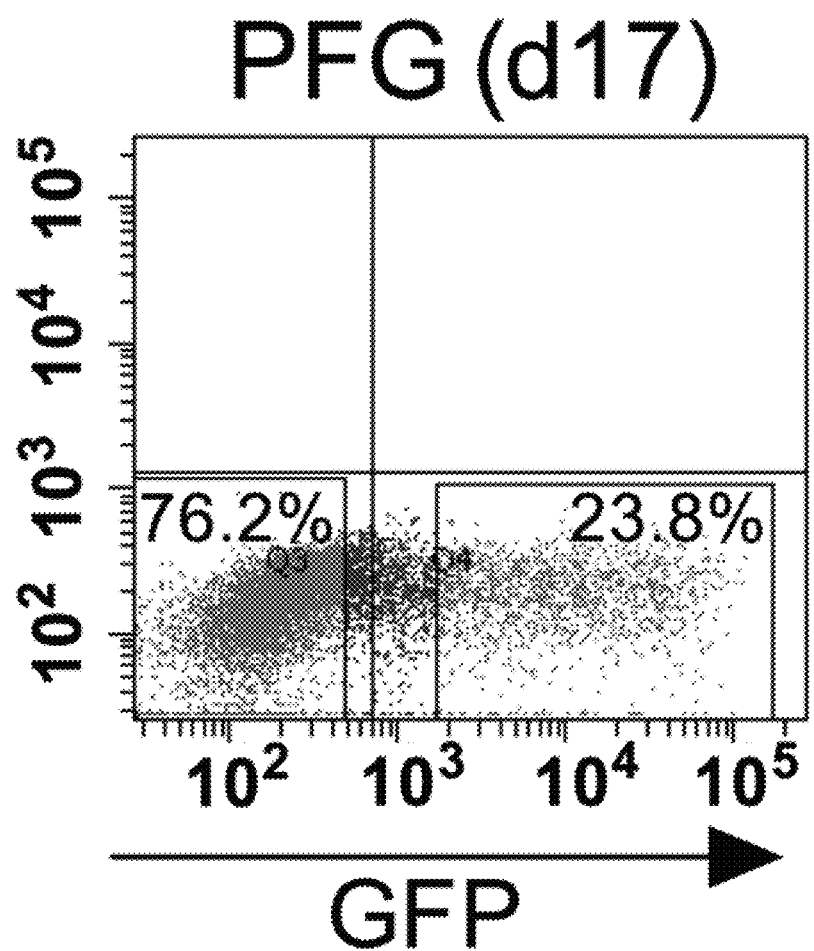
Figure 2G:
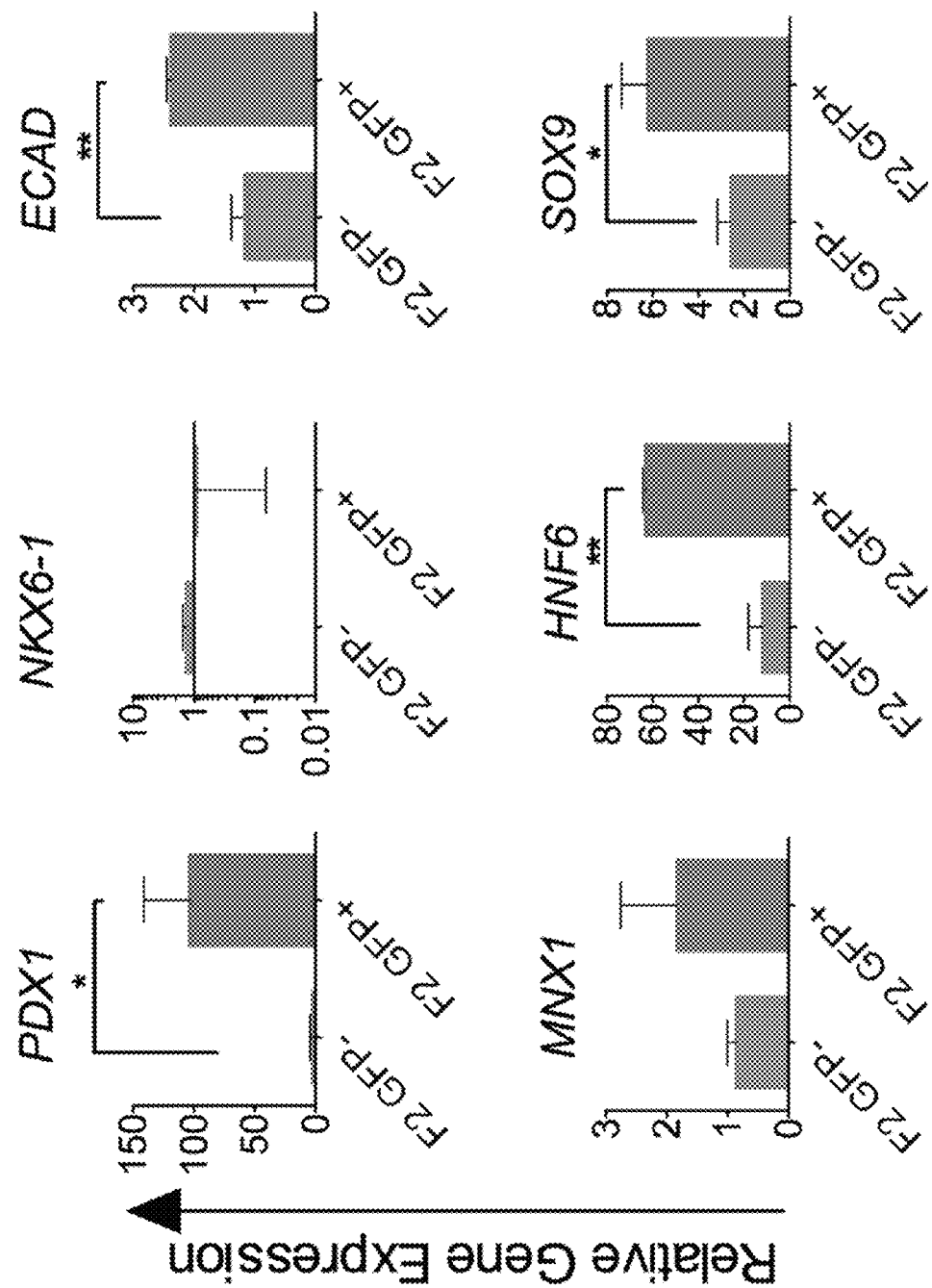

By modifying our previously published differentiation protocol (Amen et al., 2010) and combining it with the PDX1-eGFP reporter cell line described in example 2, we were able to FACS sort different subpopulations either co-expressing PDX1 and NKX6-1 (protocol A (PE)) or only expressing PDX1 while lacking NKX6-1 (protocol B (PFG)) (FIGS. 2A, 2B and 2D). To assess gene expression profiles of the FACS sorted eGFP+ and eGFP-cell populations mRNA levels of various pancreas-associated genes were quantified by qPCR (FIG. 2C and FIG. 2F). Expression of PDX1, NKX6-1, ECAD, MNX1, HNF6, and SOX9 were all significantly up-regulated in the eGFP+ cells versus the eGFP− cells obtained with protocol A (PE) (FIG. 2D). However, neither MNX1 nor more importantly NKX6-1 were significantly up-regulated in the eGFP+ cells obtained with protocol B (PFG) (FIG. 2G). These results suggest that the eGFP+ cells obtained with protocol A (PE) are pancreatic progenitor cells while the eGFP+ cells obtained with protocol B (PFG) are posterior foregut (endoderm) cells. Immunostainings of stage 3 cells (d17) confirmed the expression of NKX6-1, ECAD, HES1, and SOX9 in the pancreatic progenitors at protein level (FIG. 2F).

Figure 3A:
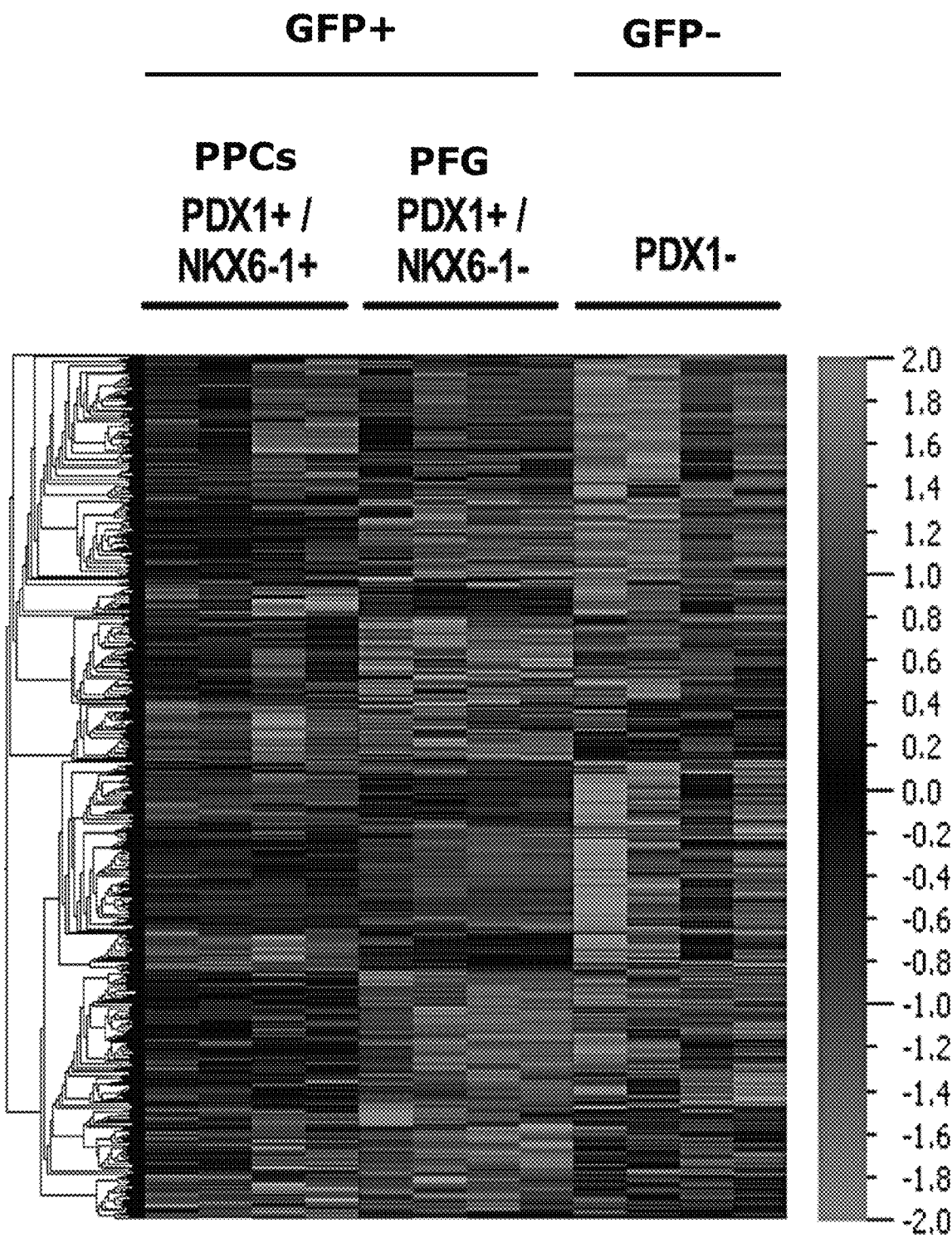
FIGS. 3A-3D. Microarray analysis was performed to compare the gene expression profiles of in vitro derived PDX1+/NKX6-1+ pancreatic progenitors (PPCs) vs PDX1+/NKX6-1- cells (PFG).
Figure 3B:
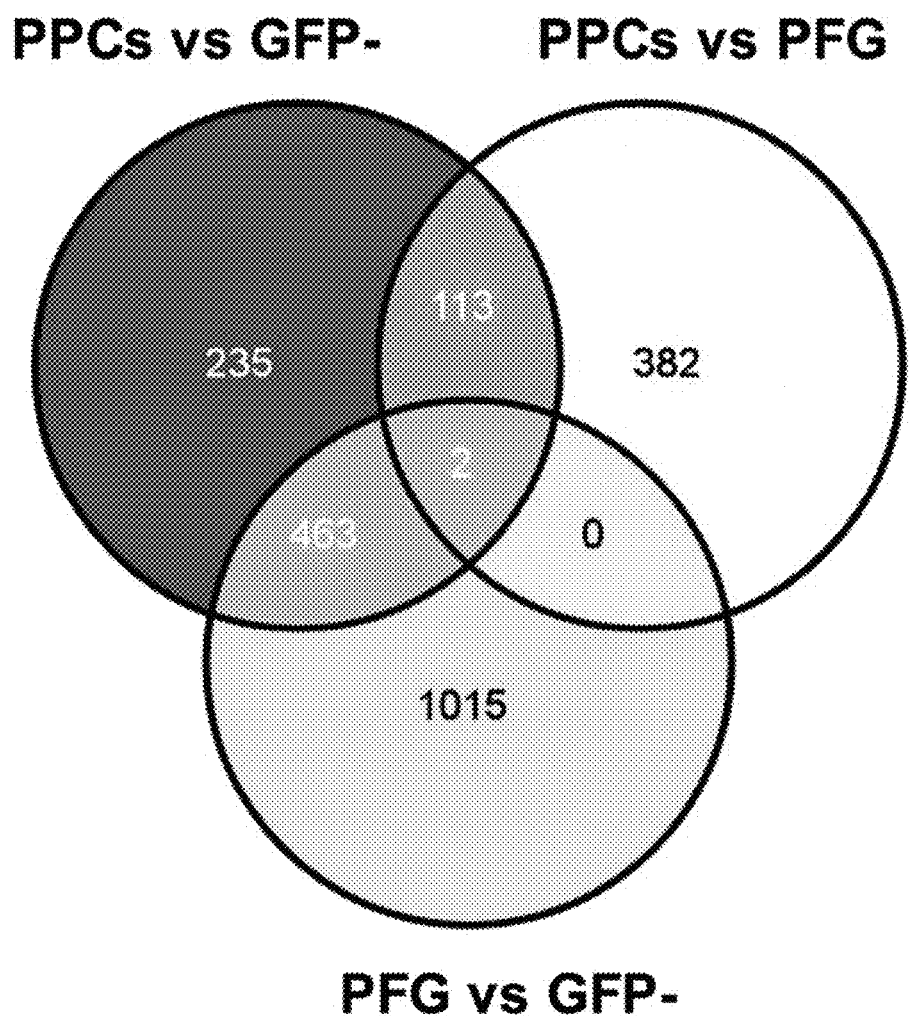
Figure 3C:
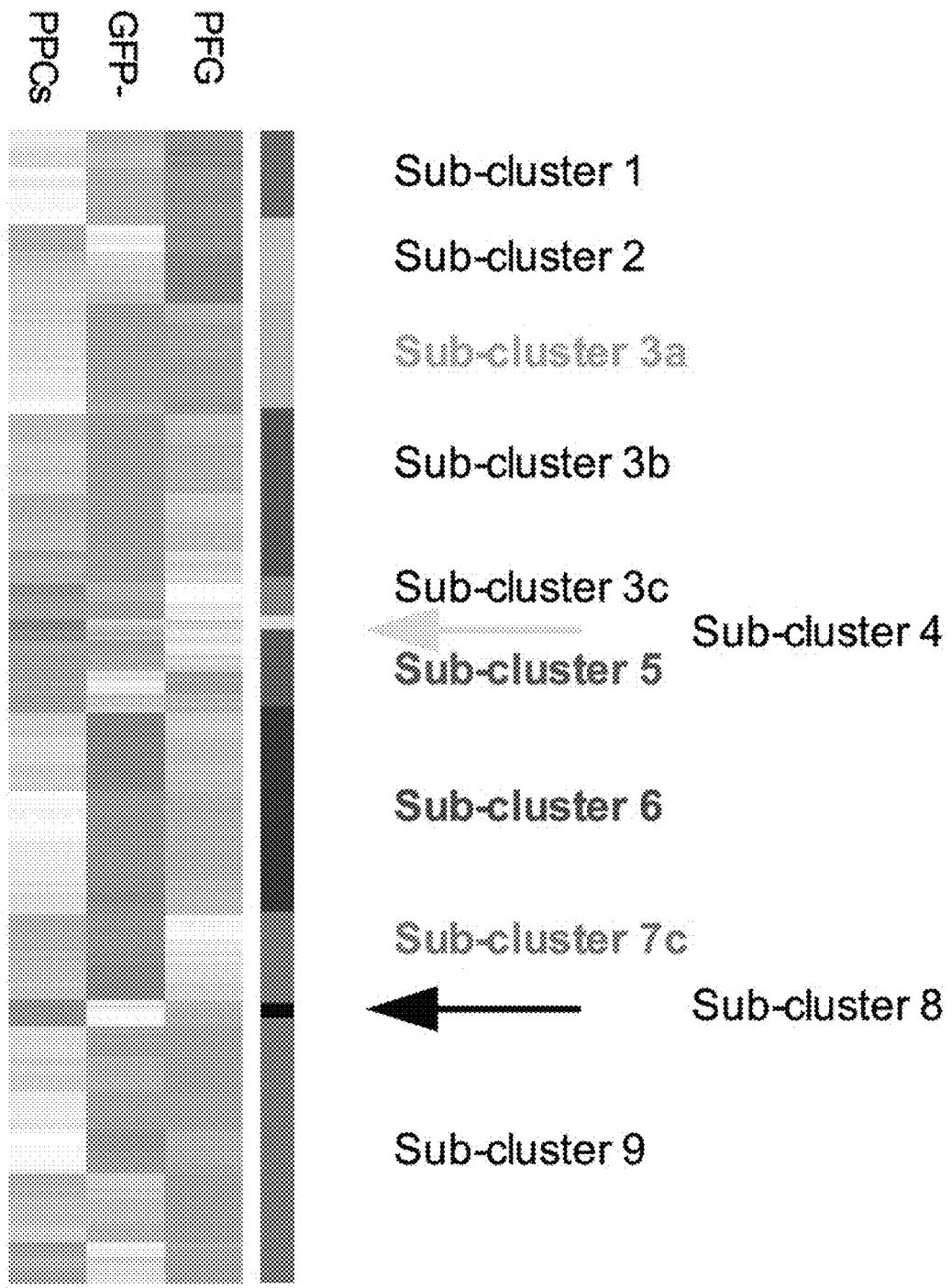
Figure 3D:
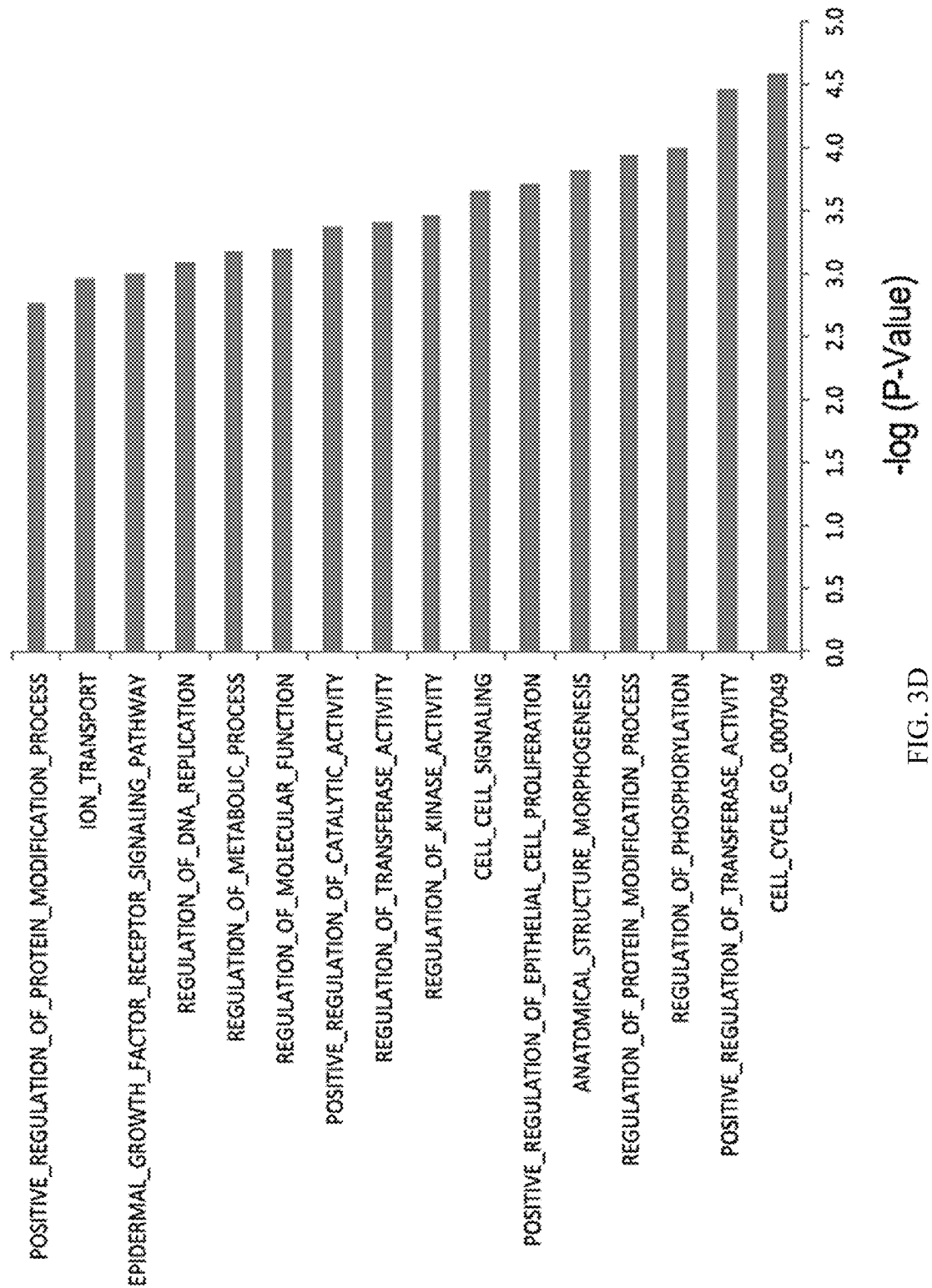

Example 4—Microarray Analysis was Performed to Compare the Gene Expression Profiles of In Vitro Derived PDX1+/NKX6-1+ Pancreatic Progenitors Versus PDX1+/NKX6-1− Cells In order to identify specific cell surface markers that would serve to enrich for pancreatic progenitors, we performed microarray analysis comparing gene expression patterns of the two distinct PDX1+ subpopulations corresponding to PDX1+ foregut endoderm (PFG) and the PDX1+/NKX6-1+ pancreatic endoderm (PPCs). Specifically, PDX1$^+$/NKX6-1 cells (referred to as PFG+), were compared with PDX1$^+$/NKX6-1$^+$ cells (referred to as PPCs), and the corresponding GFP− cells (FIG. 3A). We also compared gene expression patterns of PDX1+/NKX6-1− cells (F2 GFP+), PDX1+/NKX6-1+ cells (RFN GFP+), and the corresponding PDX1−/GFP− cells (RFN GFP−). To simplify the analysis only genes with p-values below 0.005 and a fold change above 1.4 were selected for further analysis. These cut-off values were determined based on the expression values for PDX1 and NKX6-1. Hierarchical clustering of these genes revealed enrichment of different genes in each group. Specifically, 382 genes were up-regulated/enriched in PPCs cells vs PFG cells, 698 genes were up-regulated in the PPCs+ vs GFP− cells. More interestingly, 115 genes were specifically up-regulated in the PPCs (the pancreatic progenitor cells characterized by the expression of PDX1 and NKX6-1) cells but down-regulated in PFG and GFP− cells (FIG. 3B). By applying hierarchical clustering to the average expression of all the replicates in each group, nine different sub-clusters were created (FIG. 3C).

Figure 4A:
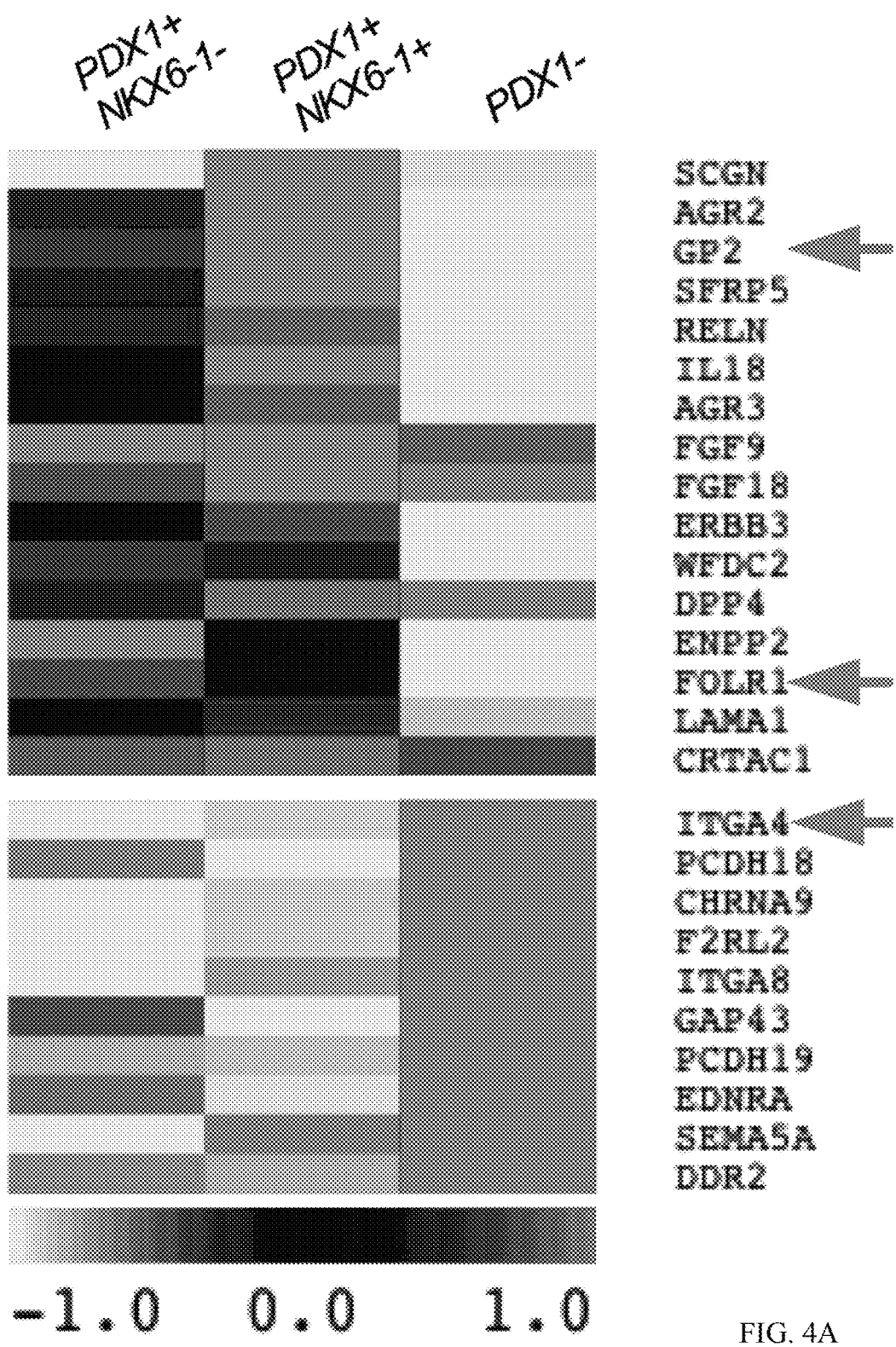
FIGS. 4A-4H. Novel cell surface markers expressed in hPSC derived PDX1+ pancreatic endoderm.
Figure 4B:
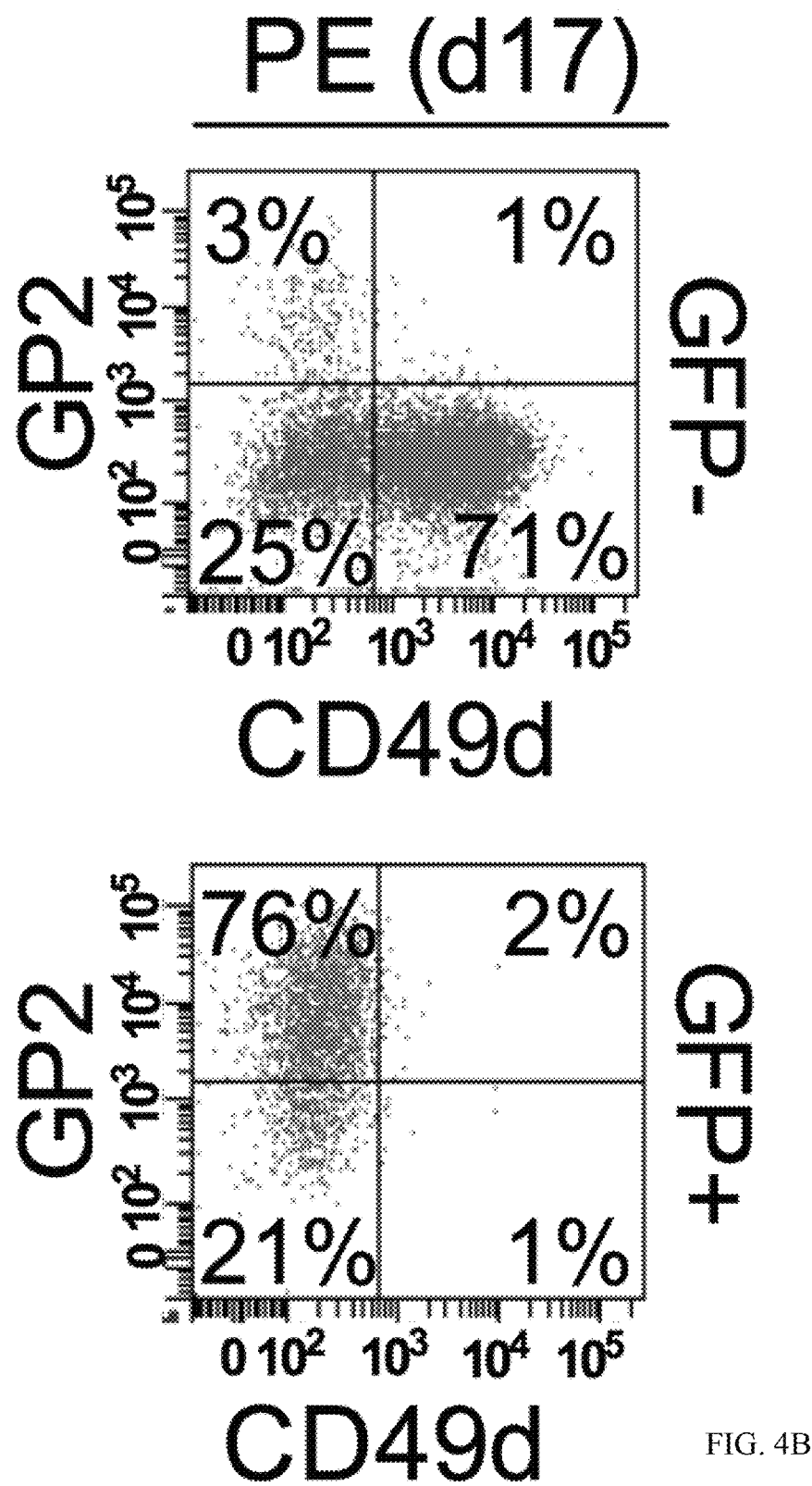
Figure 5A:
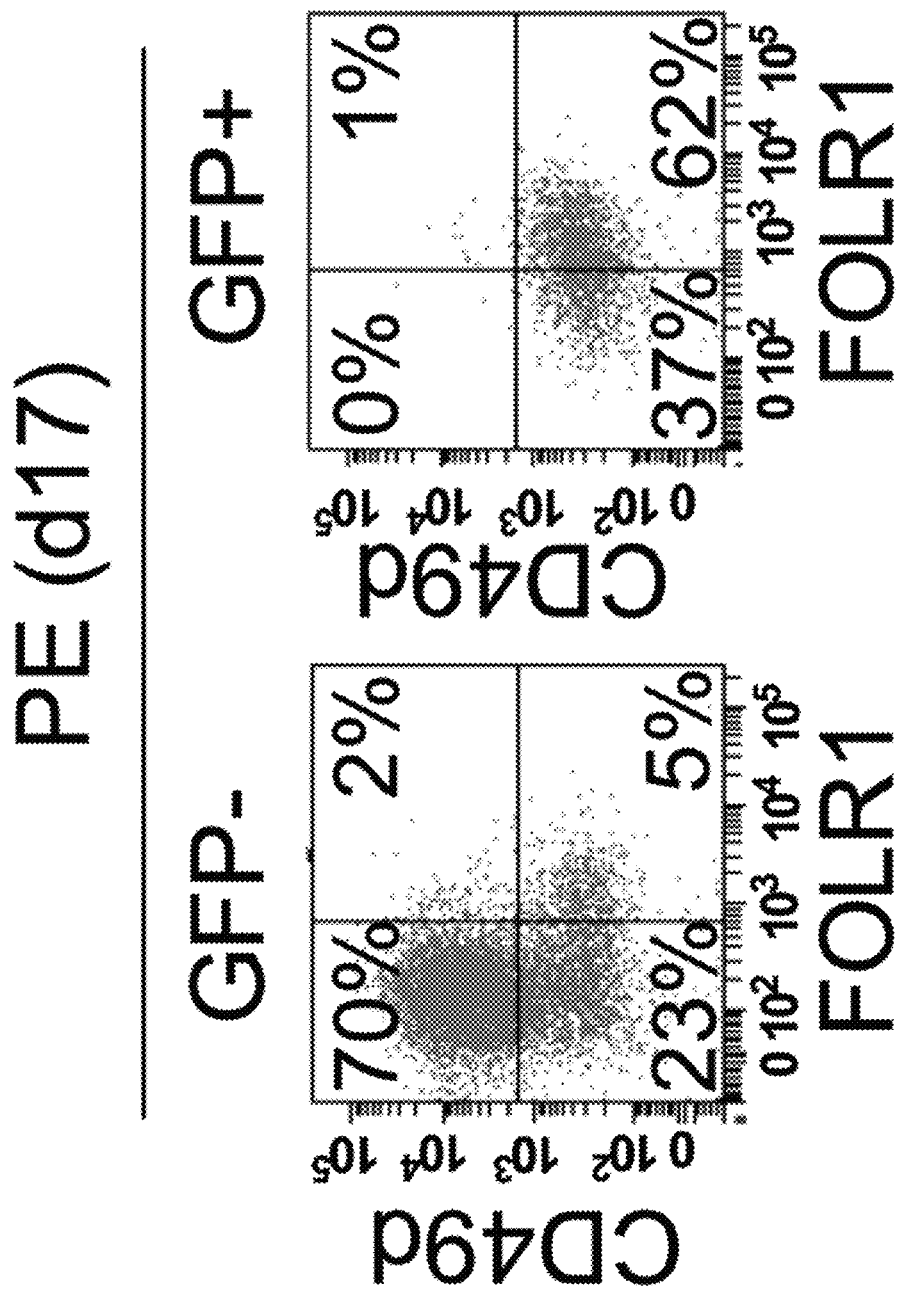
FIGS. 5A-5D. Characterization of FOLR1 expression in differentiated hPSCs.
Figure 5B:
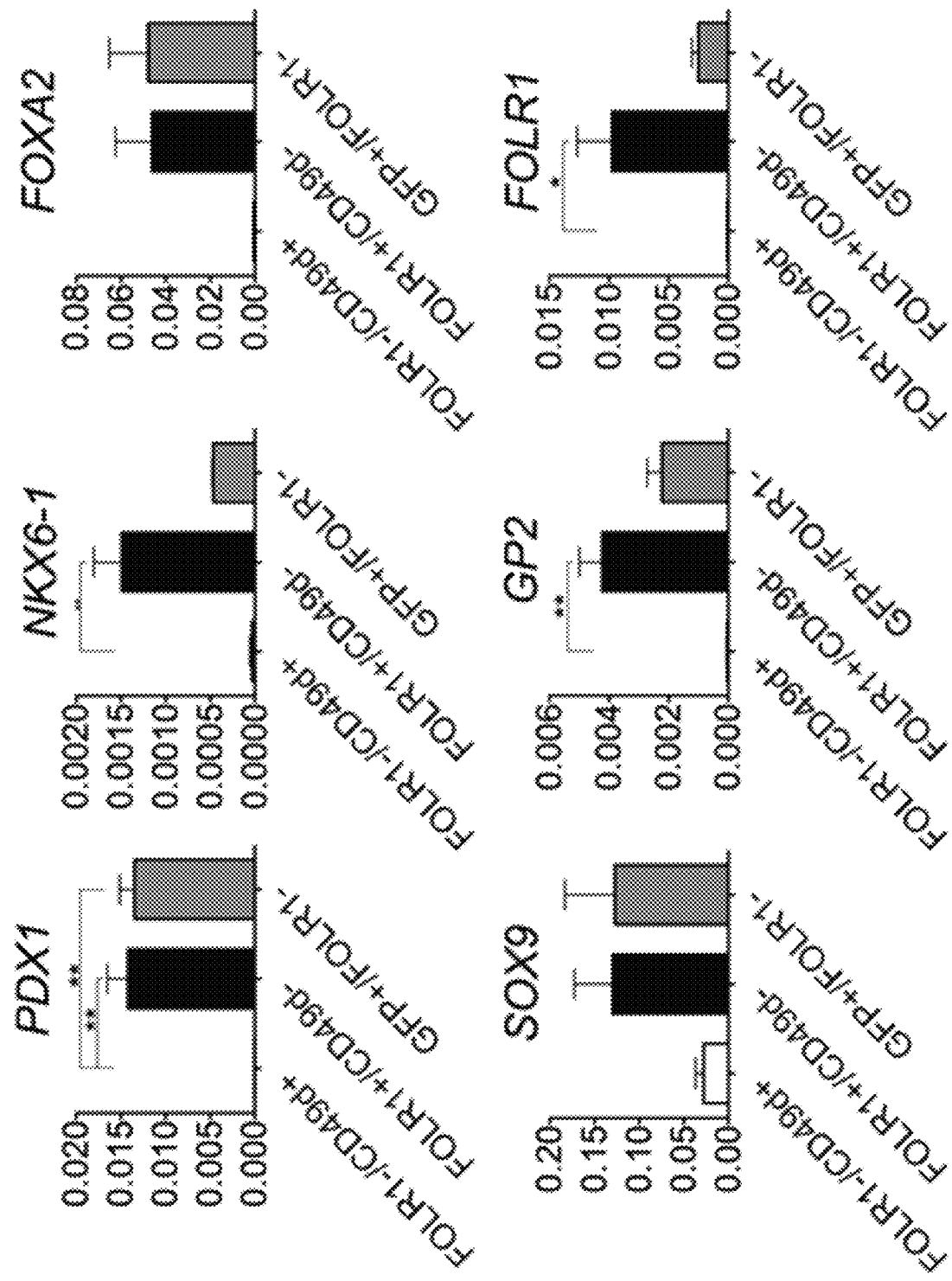
Figure 5B:
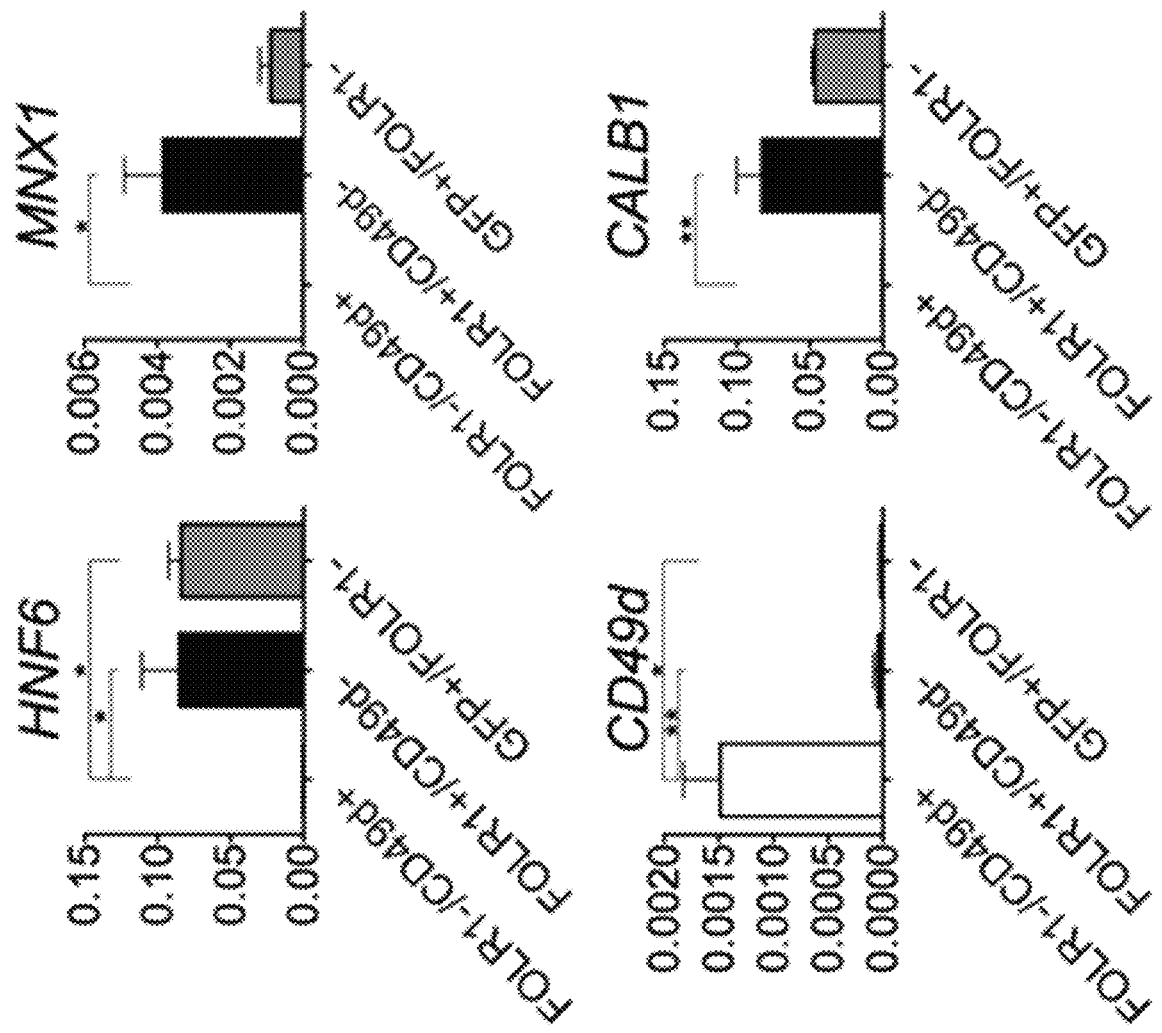

Example 5—Novel Cell Surface Markers Expressed in hESC Derived PDX1+ Pancreatic Endoderm Among the genes listed in sub-clusters 3a, 5, and 6 we identified the novel cell surface markers Integrin alpha 4 (ITGA4 or CD49d) enriched in the GFP− cells (Sub-cluster 3a), Folic receptor 1 (FOLR1) that recognizes PDX1+ cells irrespective of NKX6-1 expression (Sub-cluster 6), and glycoprotein 2 (zymogen granule membrane) (GP2) that is specifically enriched in the PDX1+/NKX6-1+ pancreatic progenitors (Sub-cluster 5). GP2, FOLR1, and CD49d were validated by flow cytometry for purification of PPCs derived from PDXeG cells (FIG. 4A). Candidate genes were validated by flow cytometry to identify cell surface markers for purification of hESC-derived pancreatic progenitor cells. Based on the availability of commercial antibodies, glycoprotein 2 (zymogen granule membrane) (GP2), folate receptor 1 (adult) (FOLR1) and CD49d (ITGA4) were selected and analyzed by flow cytometry. FIG. 4A shows the enrichment of genes localized in the plasma membrane or the extracellular region in the GFP+ and GFP− fractions. FIG. 4B and FIG. 5A show flow cytometric analysis of the selected cell surface markers GP2, CD49d (ITGA4), and FOLR1 performed on differentiated hESCs cultured on MEFs (day 17), confirming that GP2 and FOLR1 were highly expressed in the GFP+ cells whereas CD49d was enriched in the GFP-cells. More specifically, the majority of the GFP− cells (70-72%, about 71%) at day 17 expressed CD49d while 64-76% (about 76%) of the GFP+ cells co-expressed GP2. Importantly, only a low fraction of the GFP− cells (3-7%, about 3%) expressed GP2 and basically none (1-2%, about 1%) of the GFP+ cells expressed CD49d. Co-stainings with FOLR1 and CD49d showed the same staining pattern for CD49d, 70-73% (about 70%) of the GFP− cells at day 17 expressed CD49d whereas 41-62% (about 62%) of the GFP+ cells expressed FOLR1 (FIG. 5A).

Figure 4C:
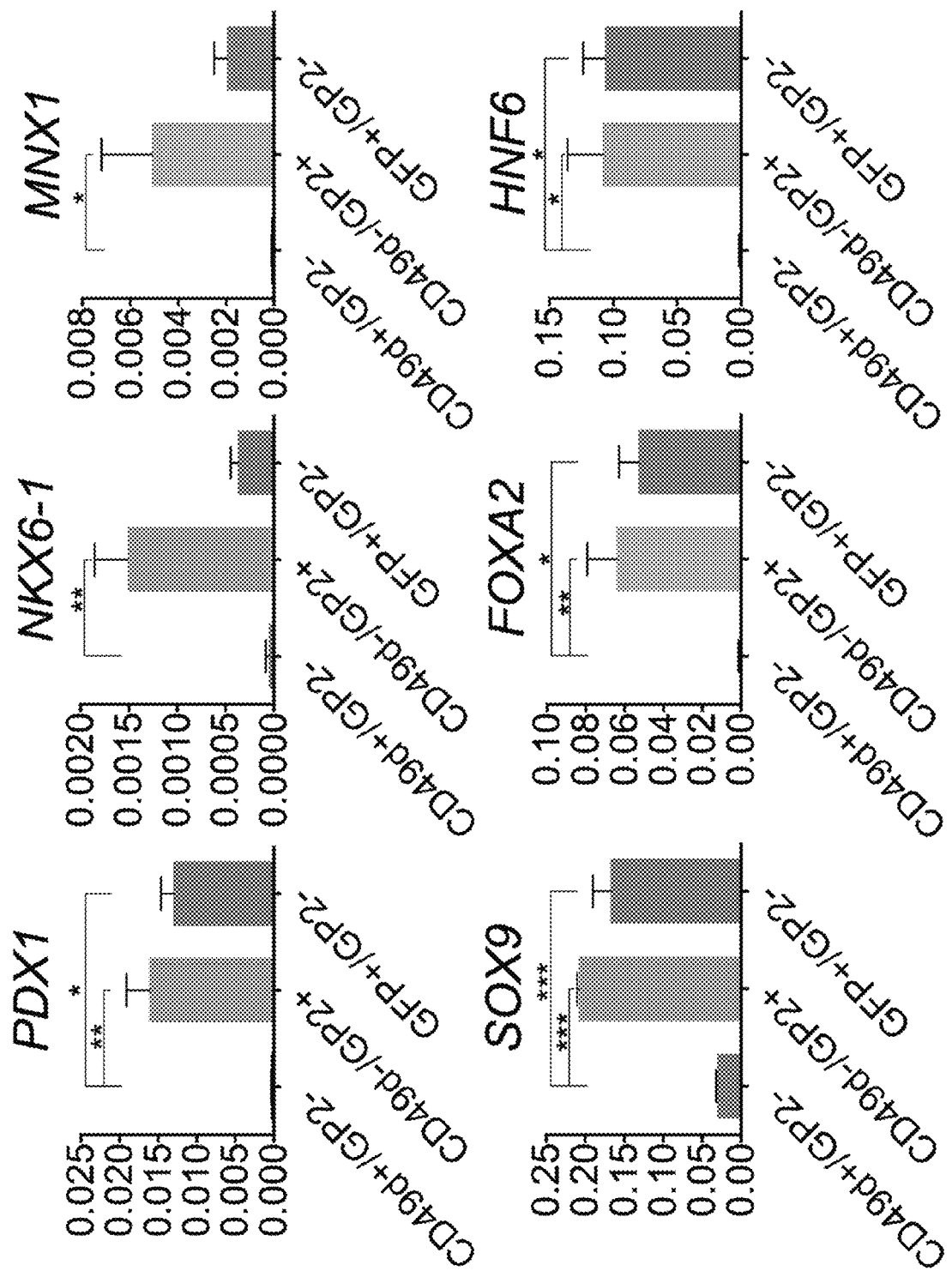
Figure 4C:
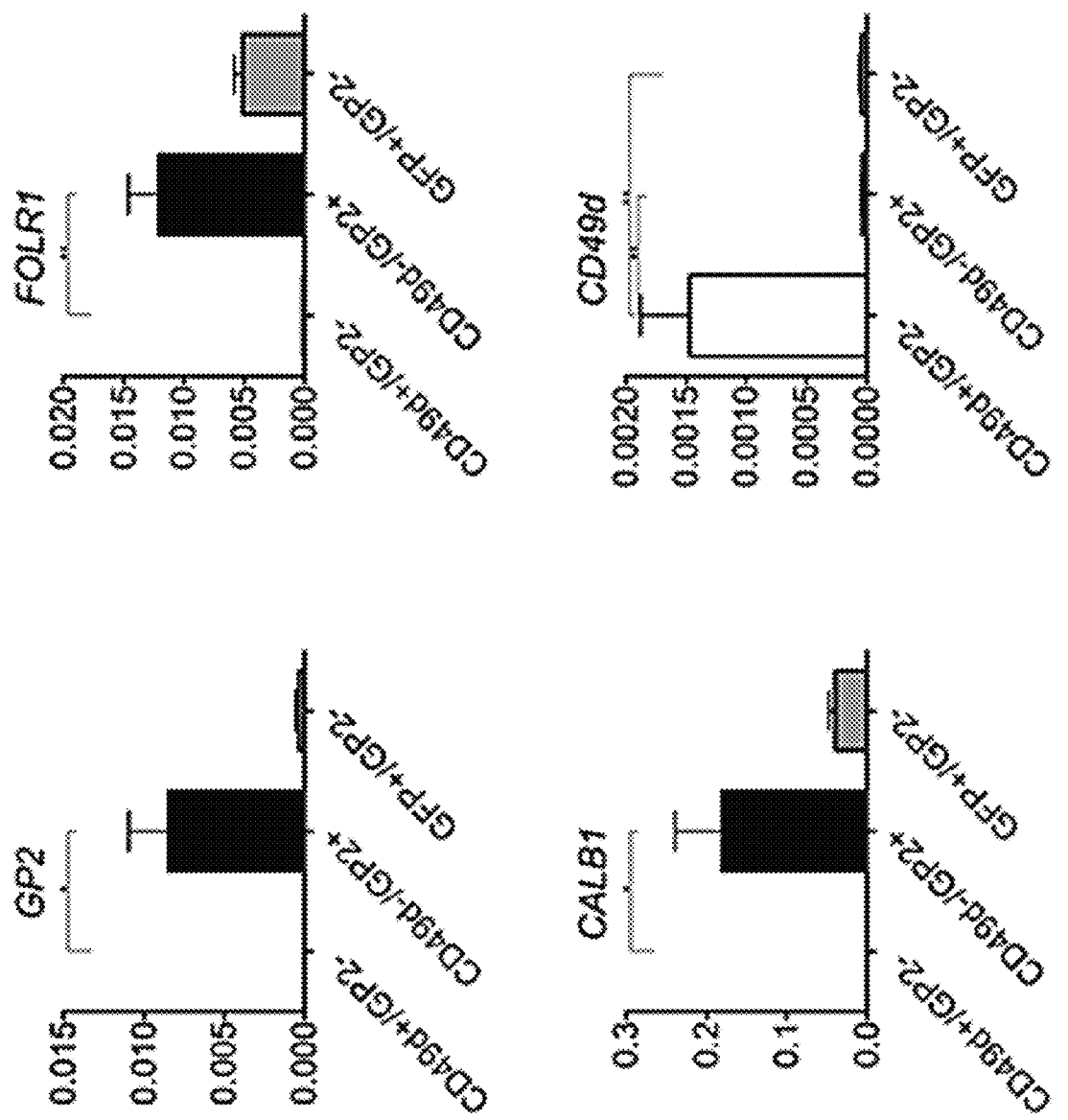
Figure 4D:
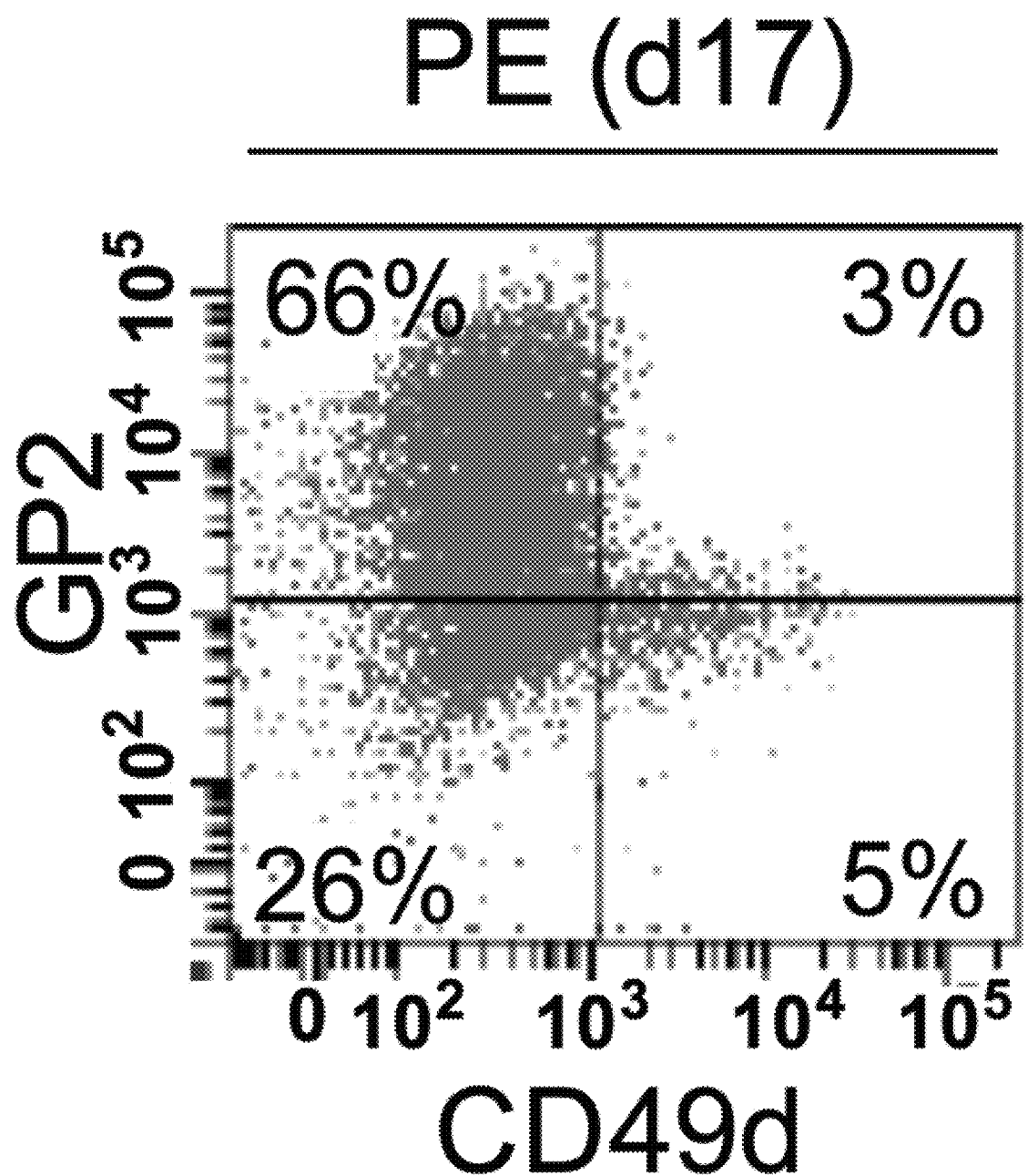

Gene expression analysis of the sorted cell populations showed that pancreatic endoderm markers and the novel cell surface markers were highly enriched in GP2+/CD49d− and FOLR1+/CD49d− sorted cell population (FIG. 4C and FIG. 4D).

The relative values for gene expression in cell populations dependent on GP2 expression (FIG. 4C) are shown in Table 1.

TABLE 1

| Gene | CD49d+/GP2− | CD49d−/GP2+ | GFP+/GP2− |
|---|---|---|---|
| PDX1 | 1 | 79.43925234 | 64.43679292 |
| NKX6-1 | 1 | 28.07471796 | 6.916959497 |
| FOXA2 | 1 | 70.28477547 | 57.69989047 |
| HNF6 | 1 | 95.92198582 | 94.5035461 |
| MNX1 | 1 | 107.1615812 | 41.10307224 |
| SOX9 | 1 | 6.819672131 | 5.498360656 |
| GP2 | 1 | 396.9765153 | 18.2205972 |
| FOLR1 | 1 | 96.72 | 41.208 |
| CD49d | 1 | 0.02622449 | 0.033469388 |
| CALB1 | 1 | 371.1526237 | 81.40750918 |

The relative values for gene expression in cell populations dependent on FOLR1 expression (FIG. 4D) are shown in Table 2.

TABLE 2

| Gene | FOLR1−/CD49d+ | FOLR1+/CD49d− | GFP+/FOLR1− |
|---|---|---|---|
| PDX1 | 1 | 259.502924 | 246.1622807 |
| NKX6-1 | 1 | 44.37113647 | 13.96219686 |
| FOXA2 | 1 | 71.78849145 | 74.47900467 |
| HNF6 | 1 | 119.2727273 | 117.4825175 |
| MNX1 | 1 | 537.2883727 | 123.8701553 |
| SOX9 | 1 | 4.657337639 | 4.562970936 |
| GP2 | 1 | 104.4978435 | 55.05853358 |
| FOLR1 | 1 | 108.1436464 | 27.90055249 |
| CD49d | 1 | 0.032021491 | 0.013566152 |
| CALB1 | 1 | 140.7758767 | 78.90902931 |

Altogether, these data indicate that CD49d is exclusively expressed in the GFP− cells and that GP2 marks the majority of the GFP+ cells. FOLR1 in contrast to GP2 however marks a minor portion of the GFP+ cells, making GP2 a more specific marker for recognizing PDX1+ pancreatic progenitor cells.

Figure 5C:
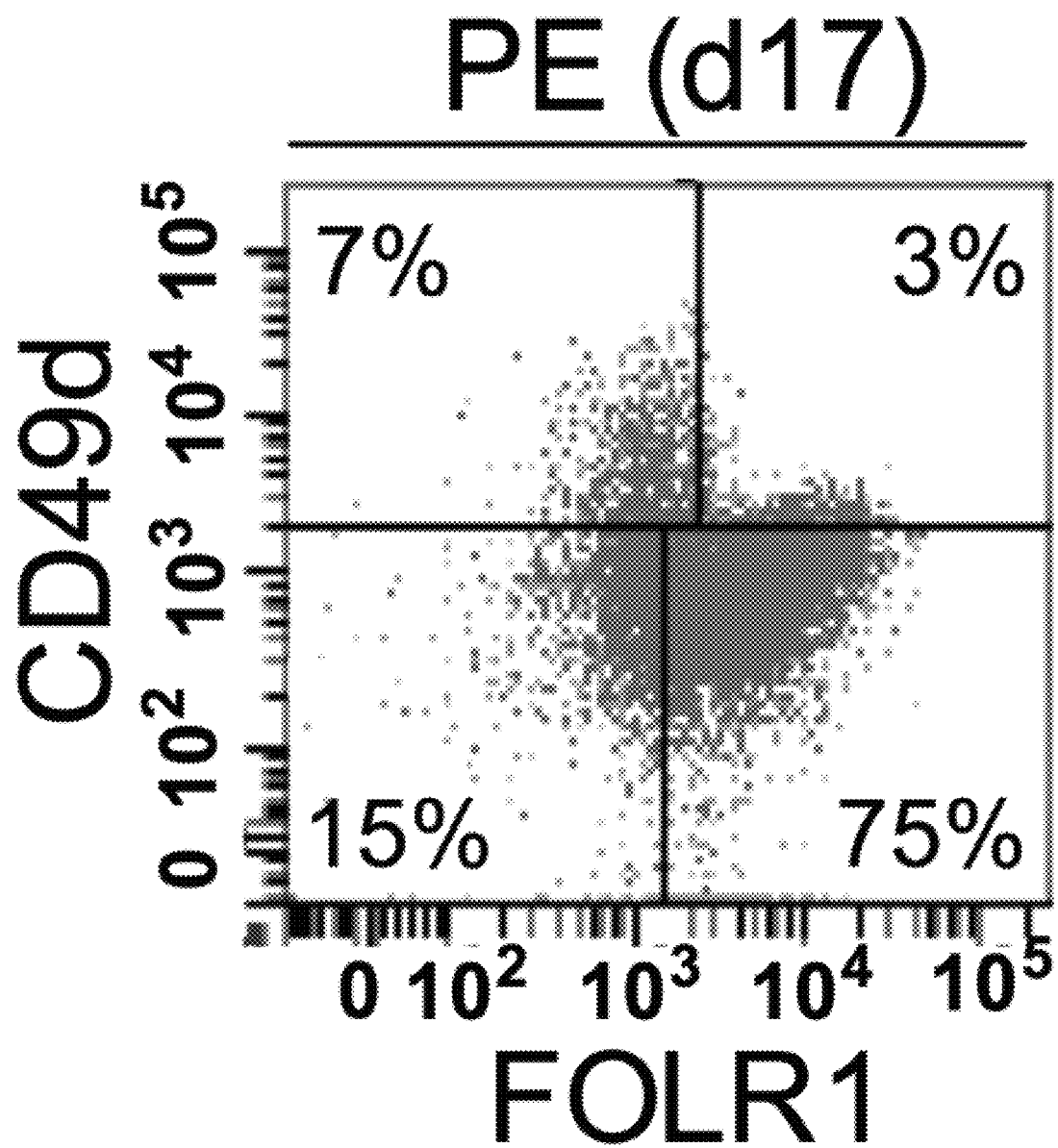

Example 6—Characterization of Novel Cell Surface Markers in a Genetically Untagged Cell Line Cultured in a Feeder Free System To investigate if our identified cell surface markers also could be used in a genetically unmodified cell line and to verify our newly identified markers, we used a genetically unmodified cell line, HUES4 cells cultured in feeder free conditions, to characterize the expression of CD49d, GP2, and FOLR1 by flow cytometry. The HUES-4 cell line was also used to generate the PDX1-eGFP cell line (FIGS. 4C and 5C). In general, our differentiation protocol works with higher efficiency in the defined feeder free culture system compared to culture on MEFs and as a consequence very few CD49d+ cells are observed.

Figure 5D:
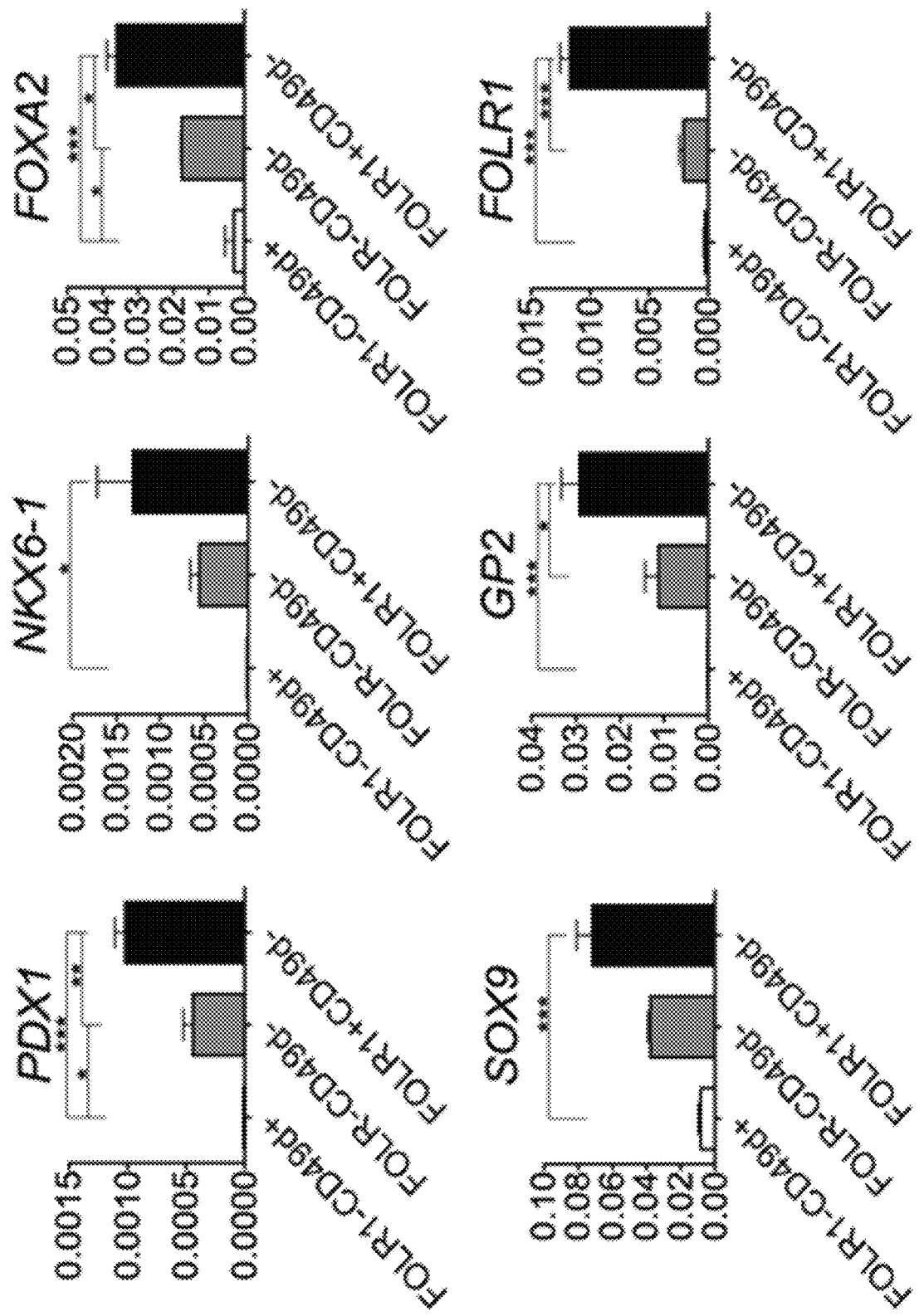
Figure 5D:
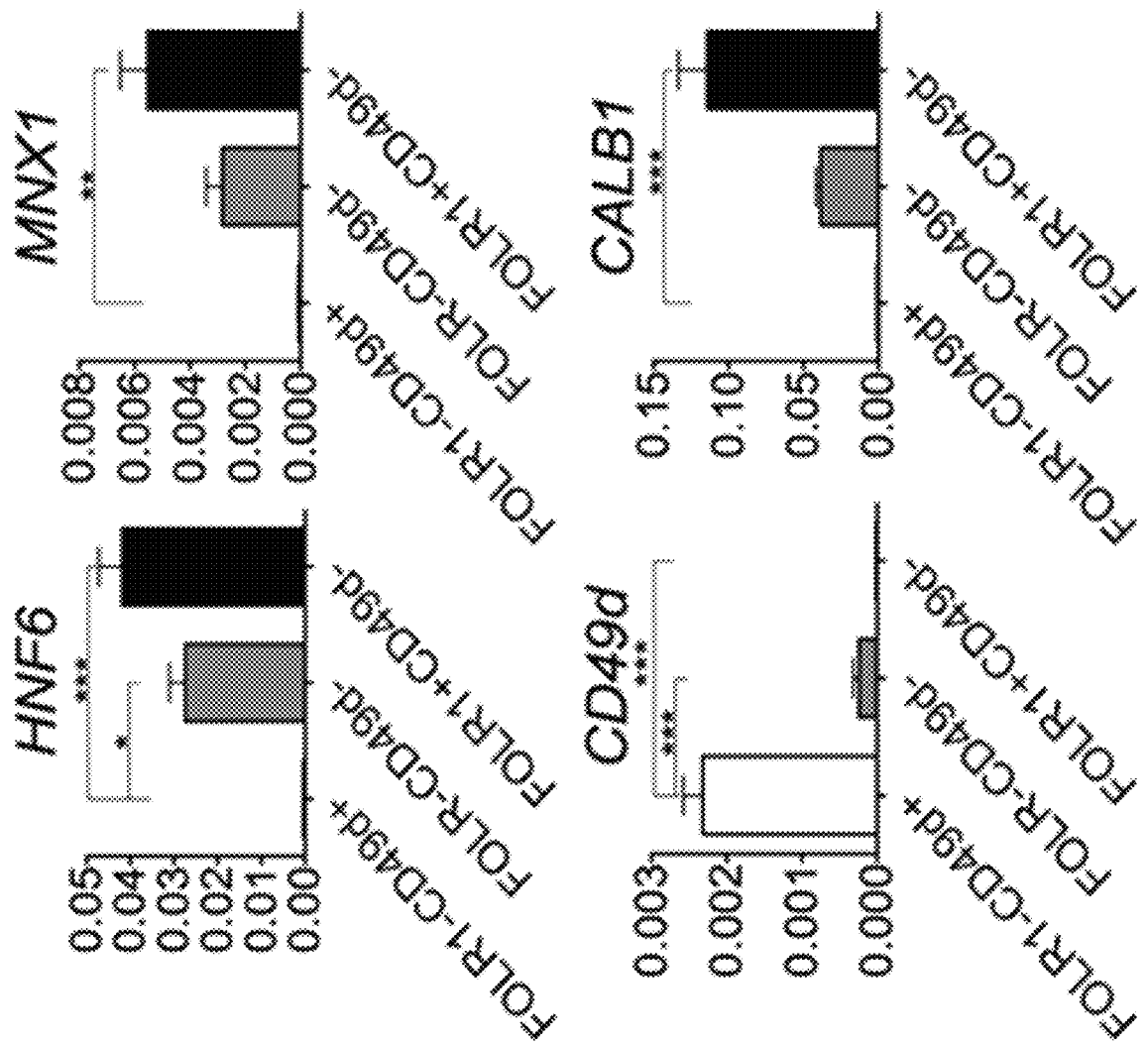

The following subpopulations were sorted and characterized by qPCR in differentiated hESCs from day 17; CD49d+/GP2, GP2−/CD49d−, and GP2+/CD49d− (FIG. 4D). The pancreatic markers PDX1, NKX6-1, SOX9, HNF6, FOXA2, MNX1 were all significantly enriched in the GP2+/CD49d− cells in comparison to the CD49d+/GP2− and GP2−/CD49d− cells. Importantly, while PDX1 was still detected in the GP2-CD49d− cells, these cells had low expression of NKX6-1 and GP2, indicating that these cells are PDX1+ posterior foregut cells. Moreover, lack of GP2 expression together with the observation that FOLR1 is still expressed in the GP2−/CD49d− cells indicates that GP2 specifically marks pancreatic progenitor cells while FOLR1 is more broadly expressed. Gene expression analysis of the subpopulations CD49d+/FOLR1−, FOLR1−/CD49d−, and FOLR1+CD49d− (FIG. 5D) showed that while all the pancreatic markers were indeed enriched in the FOLR1+/CD49d− cells, the FOLR1−CD49d− cells still contained PDX1, NKX6-1 expressing cells, indicating that FOLR1 has a somewhat lower specificity than GP2 in recognizing/labelling pancreatic progenitor cells. Hence, these data show that GP2 and FOLR1 specifically mark hESC-derived PDX1+/NKX6-1+ cells irrespective of whether they are derived in a defined feeder free culture system or on MEFs. Overall, our data indicates that GP2 specifically marks hPSC-derived PDX1+/NKX6-1+ PPCs, whereas FOLR1 recognizes both hPPCs and hPFCs lacking NKX6-1 expression.

The relative values for gene expression in cell populations dependent on FOLR1 expression (FIG. 4C) are shown in Table 3.

TABLE 3

| Gene | GP2−/CD49d+ | GP2−/CD49d− | GP2+/CD49d− |
| --- | --- | --- | --- |
| PDX1 | 1 | 48.03965133 | 142.8871763 |
| NKX6-1 | 1 | 4.573916565 | 94.66585662 |
| MNX1 | 1 | 36.98737595 | 128.0495962 |
| FOXA2 | 1 | 48.34355828 | 92.22903885 |
| SOX9 | 1 | 3.643922719 | 7.90576343 |
| HNF6 | 1 | 62.28685822 | 138.5492228 |
| GP2 | 1 | 31.15015974 | 849.8402556 |
| FOLR1 | 1 | 37.03353803 | 74.16154936 |
| CD49d | 1 | 0.040230358 | 0.010665158 |
| CALB1 | 1 | 62.13936973 | 424.7669774 |

The relative values for gene expression in cell populations dependent on GP2 expression (FIG. 5D) are shown in Table 4.

TABLE 4

| Gene | FOLR1−/CD49d+ | FOLR1−/CD49d− | FOLR1+/CD49d− |
| --- | --- | --- | --- |
| PDX1 | 1 | 44.41087613 | 102.7190332 |
| NKX6-1 | 1 | 40.03599712 | 94.81641469 |
| MNX1 | 1 | 35.98580841 | 70.19766853 |
| FOXA2 | 1 | 6.020408163 | 12.31292517 |
| SOX9 | 1 | 4.4509827 | 8.450041191 |
| HNF6 | 1 | 81.54761905 | 124.702381 |
| GP2 | 1 | 79.02097902 | 204.1958042 |
| FOLR1 | 1 | 8.366533865 | 46.61354582 |
| CD49d | 1 | 0.105603448 | 0.006073276 |
| CALB1 | 1 | 53.98601399 | 159.4405594 |

Figure 4E:
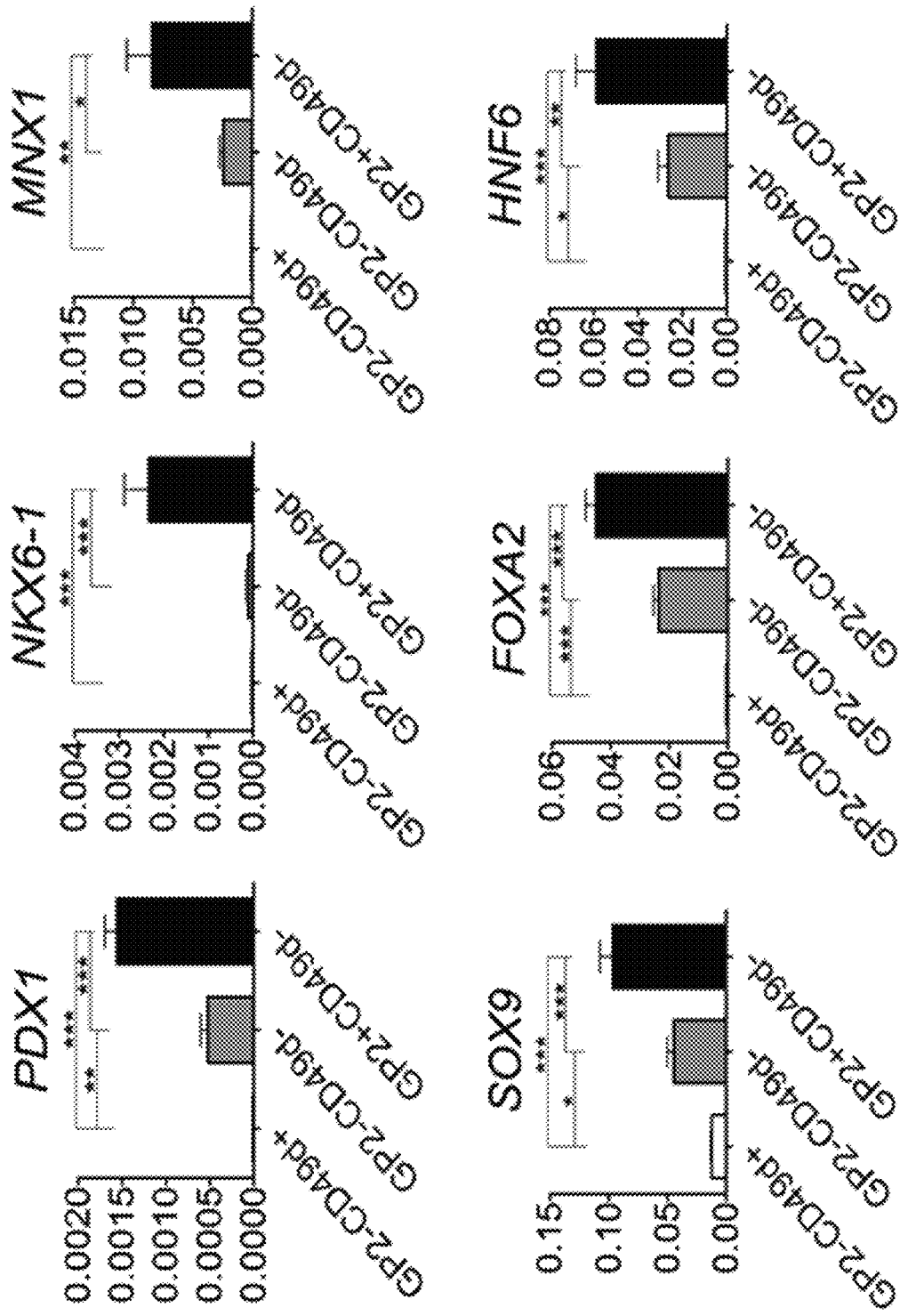
Figure 4E:
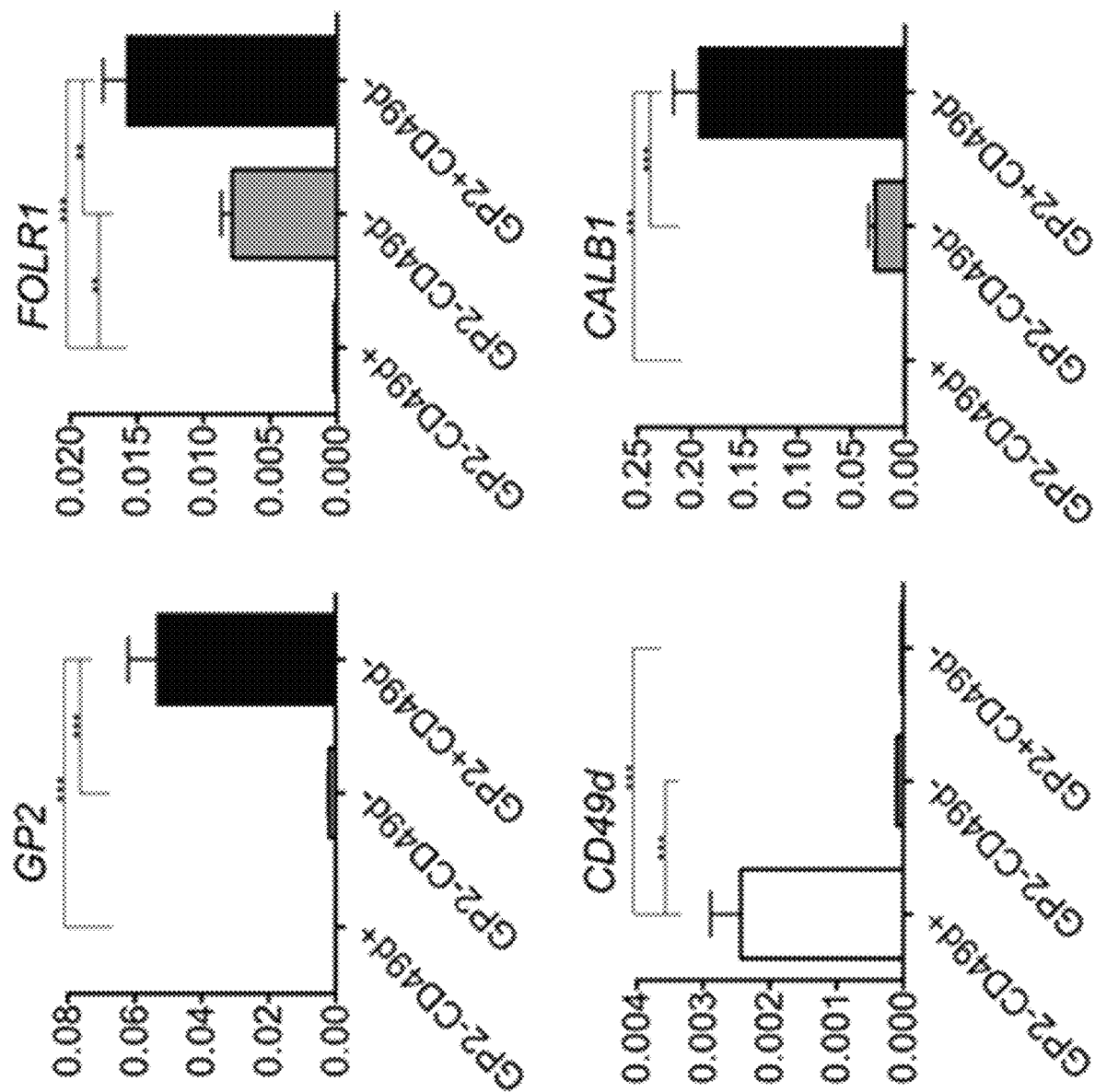
Figure 4F:
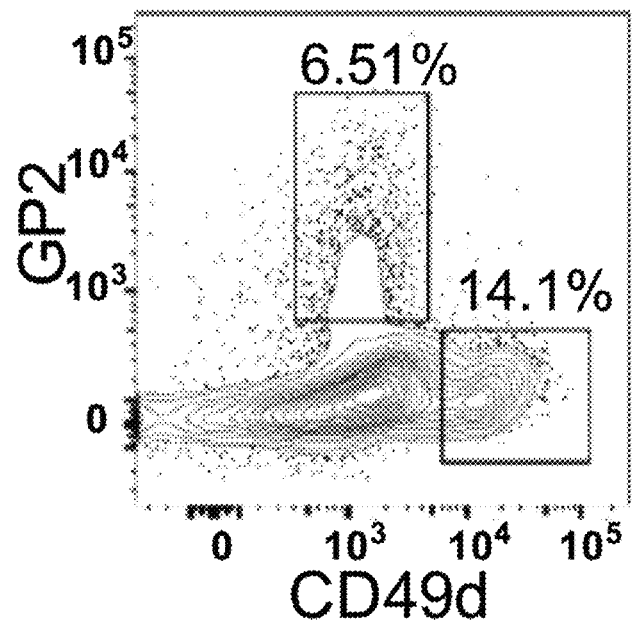
Figure 4G:
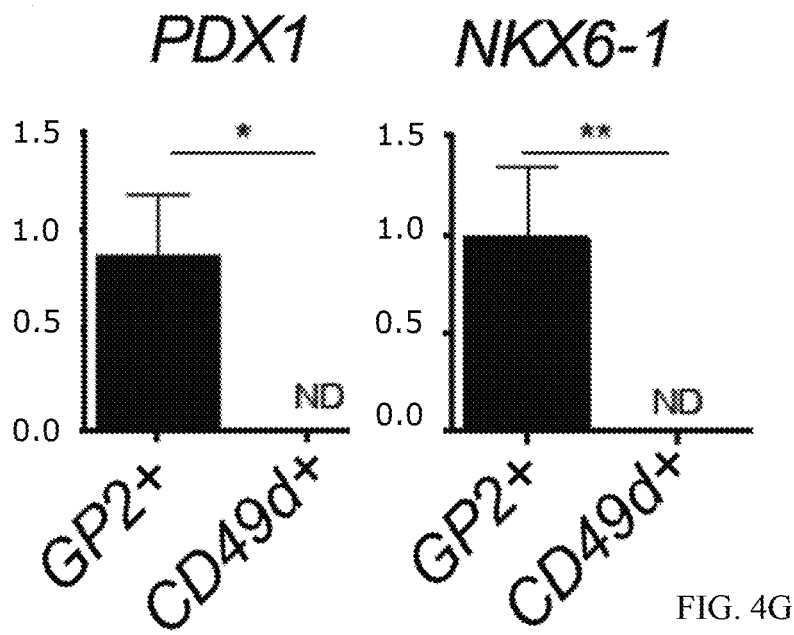
Figure 4H:
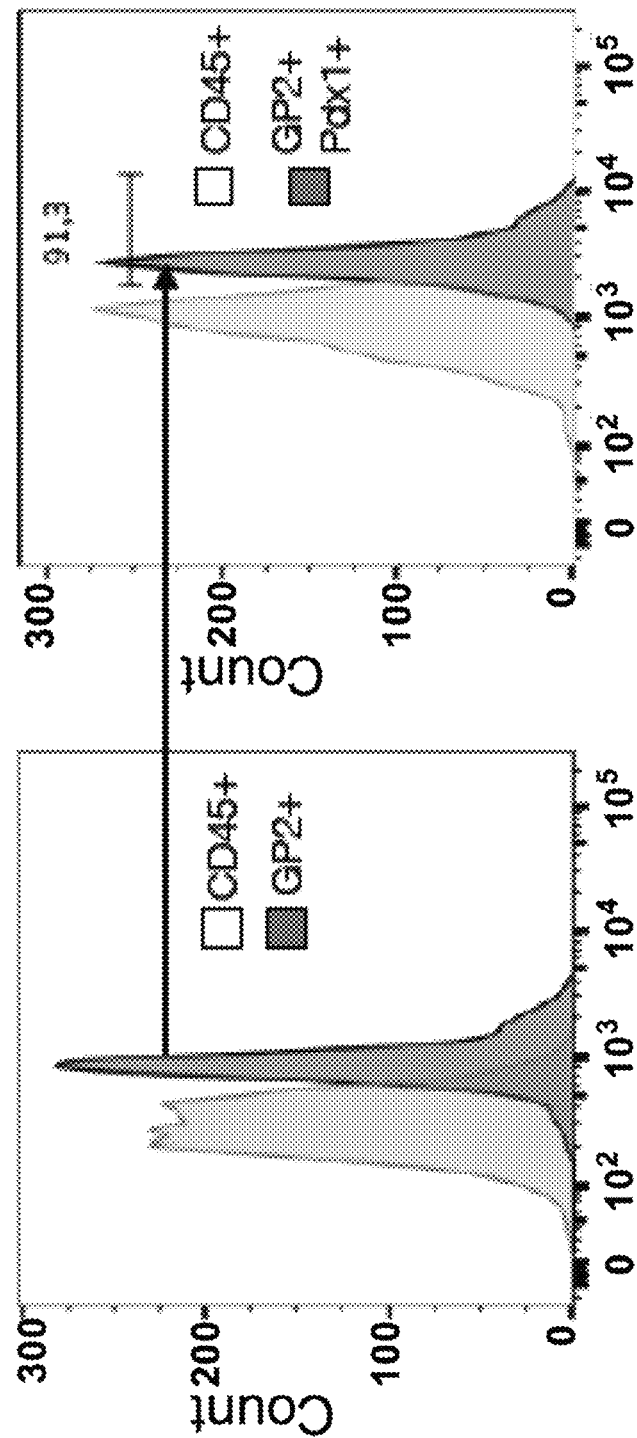

Example 7—Validation of the Novel Cell Surface Markers GP2 and CD49d in Human Foetal Pancreas In order to validate the GP2 and CD49d markers and in order to validate whether GP2 also plays a role in vivo, we used human foetal pancreas from 9.1 WD to examine the expression of GP2 and CD49d. We performed flow cytometric analysis of human foetal pancreas. Comparable to the hPSCs there was no overlap between GP2 and CD49d expression in the human foetal pancreas (FIG. 4E). PDX1 and NKX6-1 expression was analyzed in FACS sorted GP2+ and CD49d+ cell populations. PDX1 and NKX6-1 were significantly enriched in the GP2+ cells, with no expression detected on CD45+/CD31+ hematopoietic and endothelial cells used as a control (FIG. 4G).

Altogether, these results show that GP2+ cells both in hESCs and in human foetal pancreas mark pancreatic progenitors characterized by PDX1 and NKX6-1 expression and GP2 can be utilized to isolate PPCs from both hPSCs in vitro and human foetal pancreas in vivo.

Figures 6A, 6B:
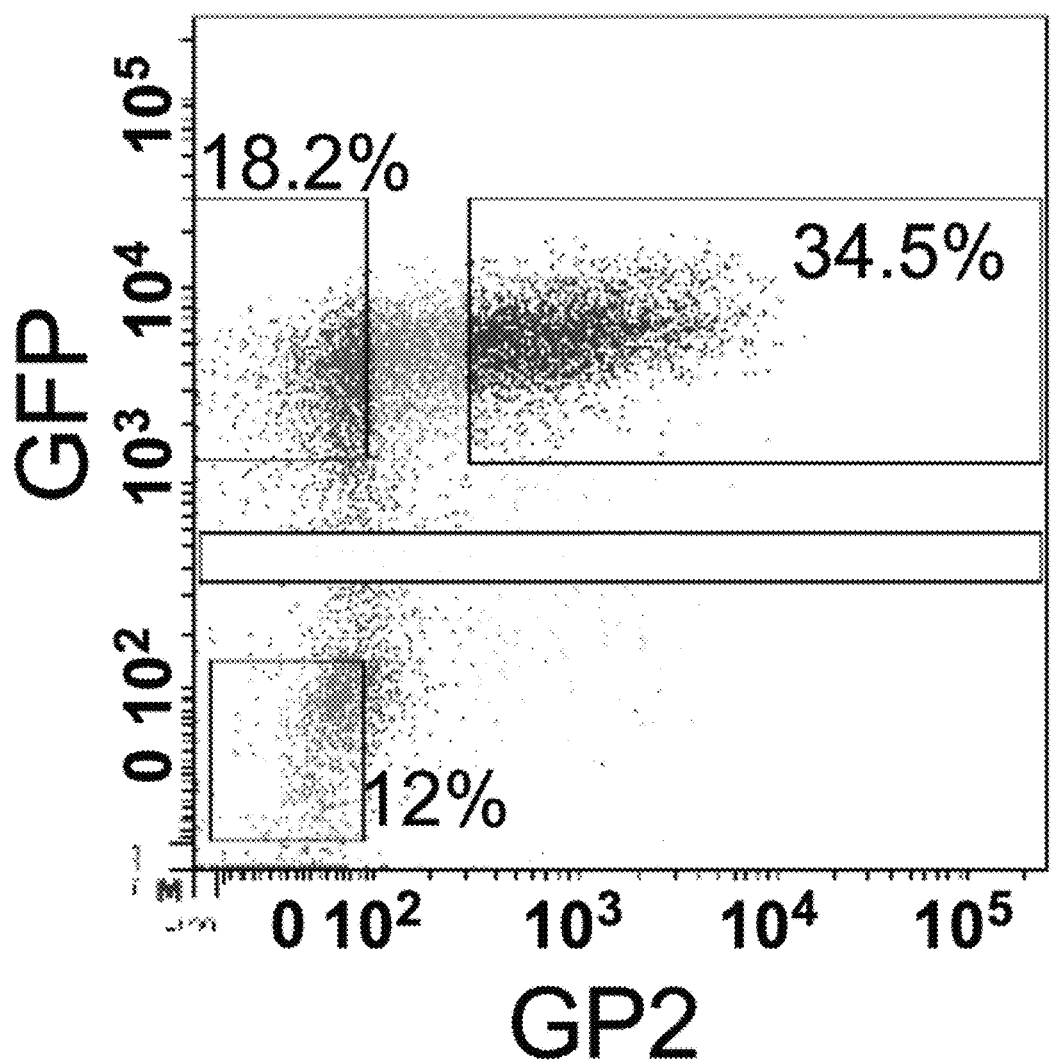
FIGS. 6A-6B. Validation of GP2 using an independent and previously published differentiation protocol.
Figure 6C:
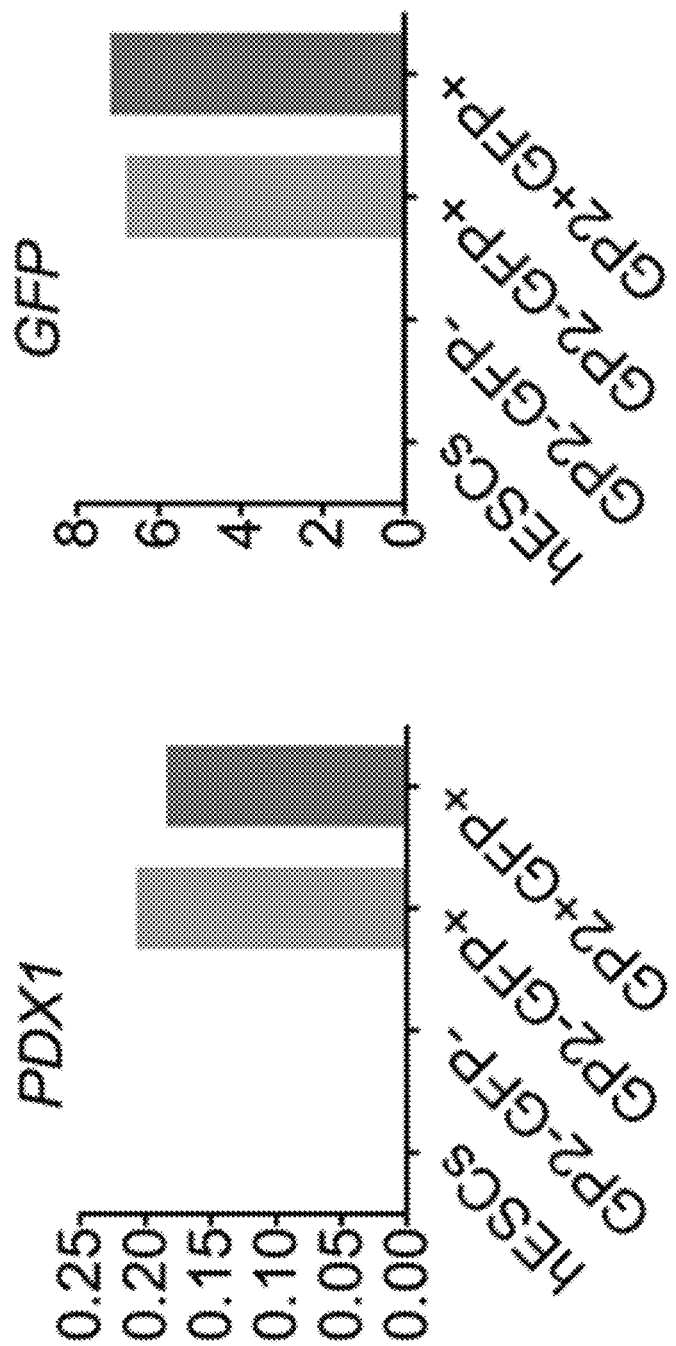
FIG. 6C) qPCR analysis of the sorted populations: GP2-GFP−, GP2-GFP+, and GP2+GFP+ cells showed that PDX1 and NKX6-1 expressing cells are significantly enriched in the GP2+GFP+ cell fraction in comparison to the GP2-GFP+ cell fraction. This data confirms that GP2 can be used to isolate human pancreatic progenitors co-expressing PDX1 and NKX6-1 from heterogeneous cell cultures.
Figure 6C:
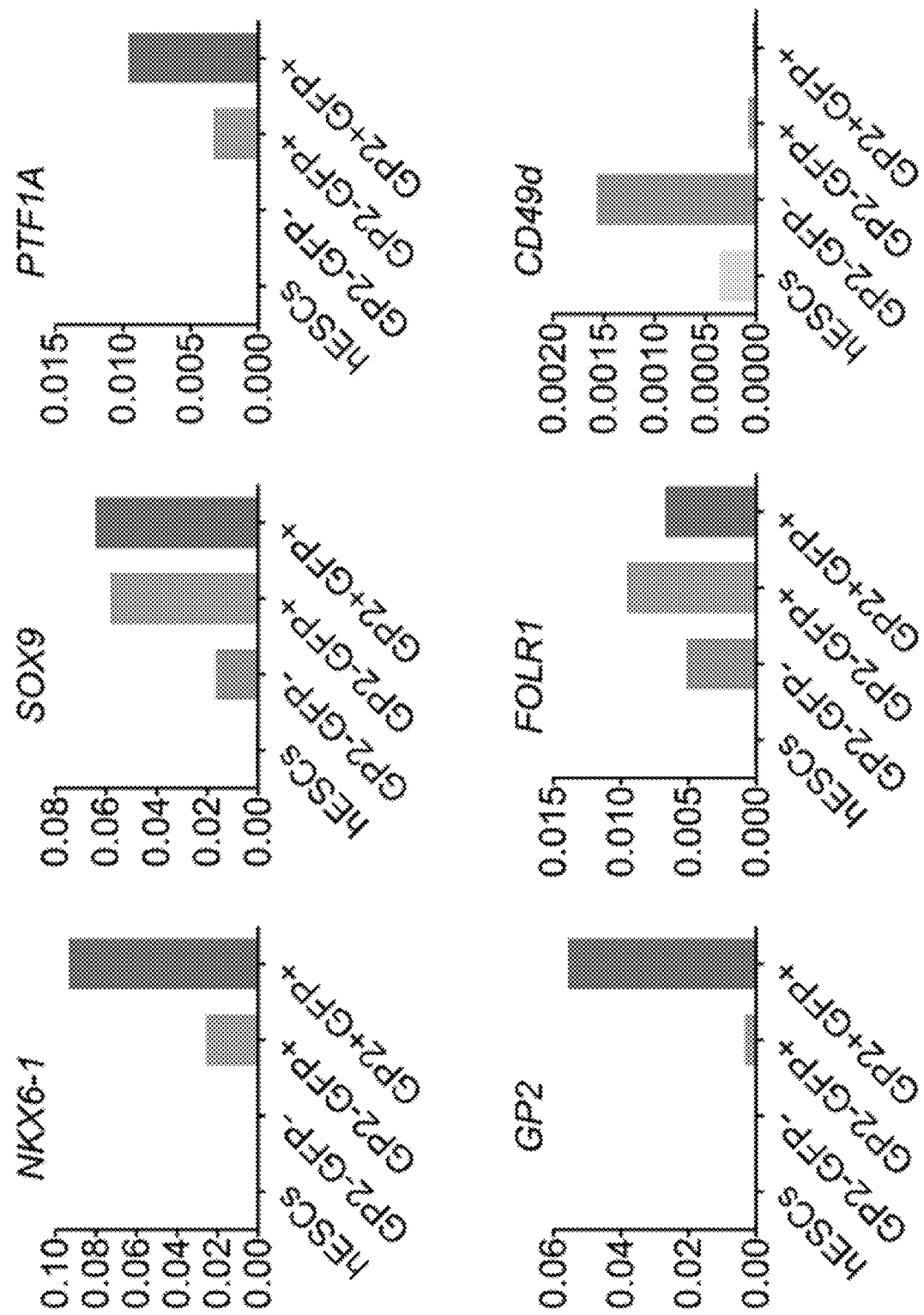

Example 8—Validation of GP2 Using an Independent and Previously Published Differentiation Protocol To corroborate our findings, the PDXeG cell line was differentiated according to a slightly modified version of a prior differentiation protocol published by Rezania et al. 2013 (FIG. 6A) and different subpopulations were sorted based on GP2 and GFP expression (FIG. 6B). In contrast to what we observed with our protocol, Rezania's protocol gives rise to a heterogeneous cell population consisting of GFP+/GP2− and GFP+/GP2+ cells (FIG. 6B). Gene expression analysis revealed that the GP2+GFP+ cells were significantly enriched for the PPC associated genes PDX1, NKX6-1, SOX9, GP2 and PTF1a, whereas the GP2−GFP− cells expressed high levels of CD49d (FIG. 6C). The highest level of FOLR1 was observed in the GP2−GFP+ cells, however FOLR1 was also expressed in the GP2+/GFP+ and GP2−/GFP− cells (FIG. 6C). Collectively, these findings together with the data shown above show that GP2 can be utilized for isolation of PDX1+/NKX6-1+ hPPCs from heterogeneous differentiation cultures independent of culture system or differentiation protocol.

Figure 7A:
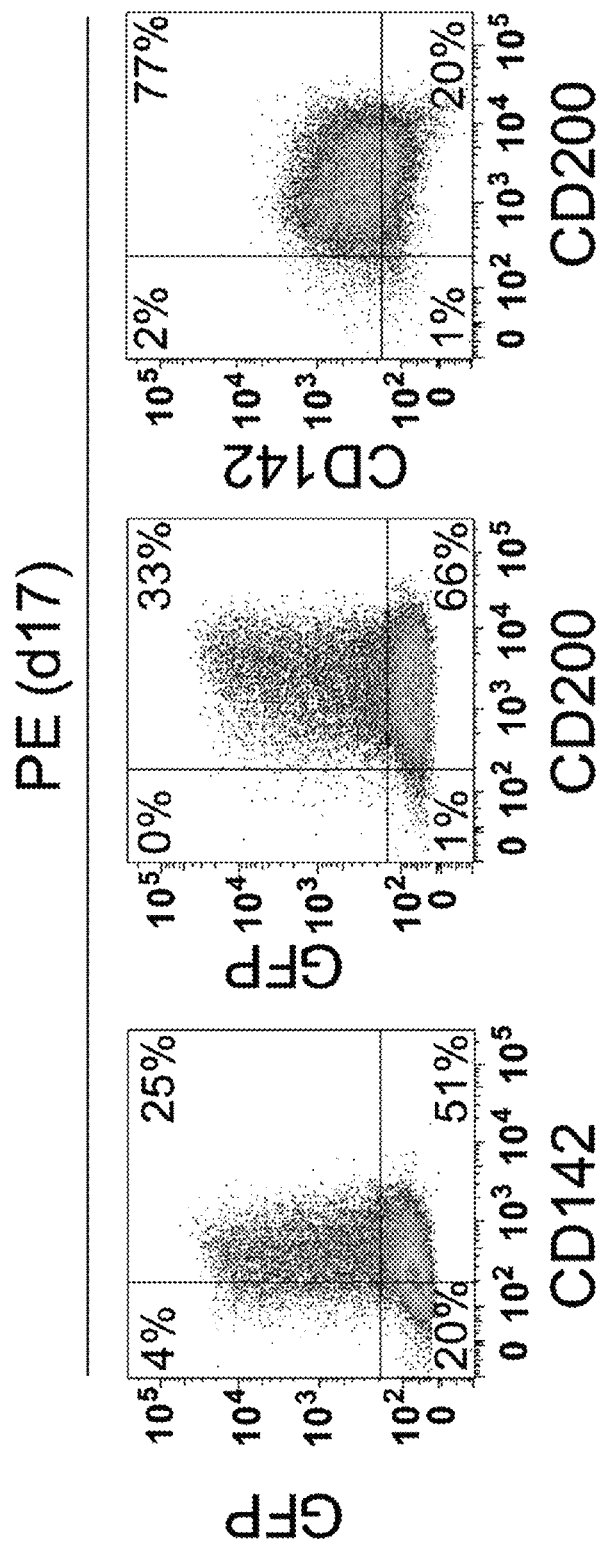
FIGS. 7A-7C. Characterization of previously published cell surface markers for purification of pancreatic progenitor cells.
Figure 7B:
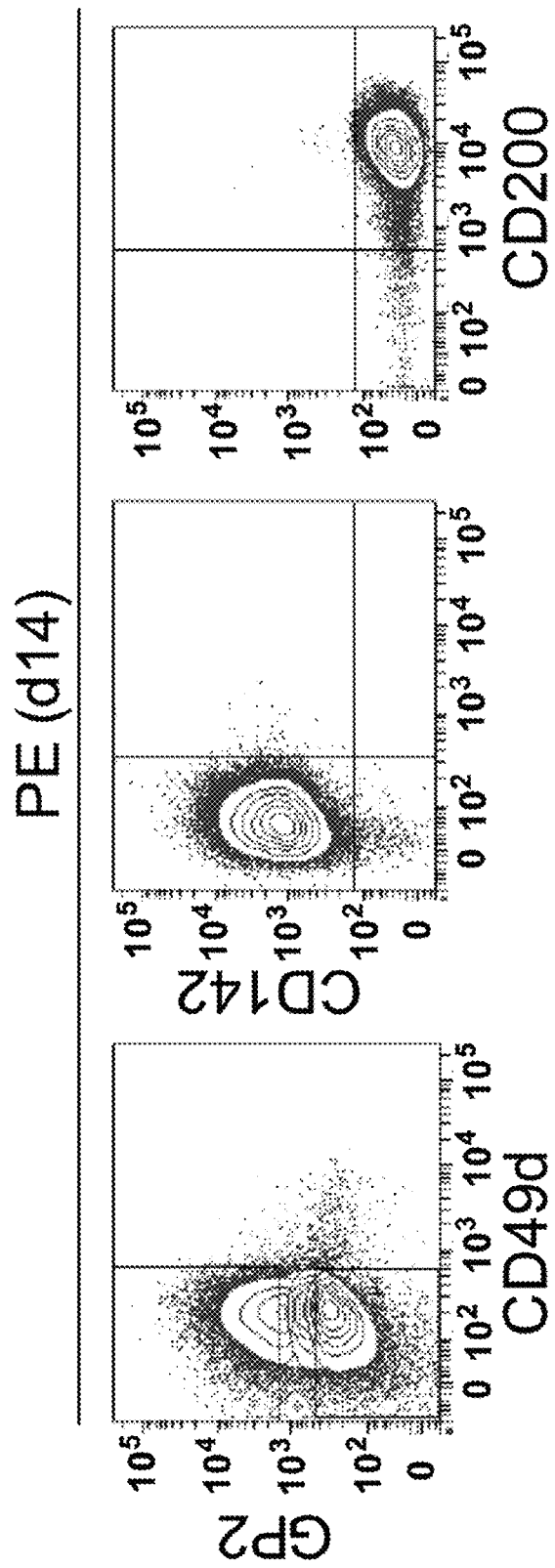
Figure 7C:
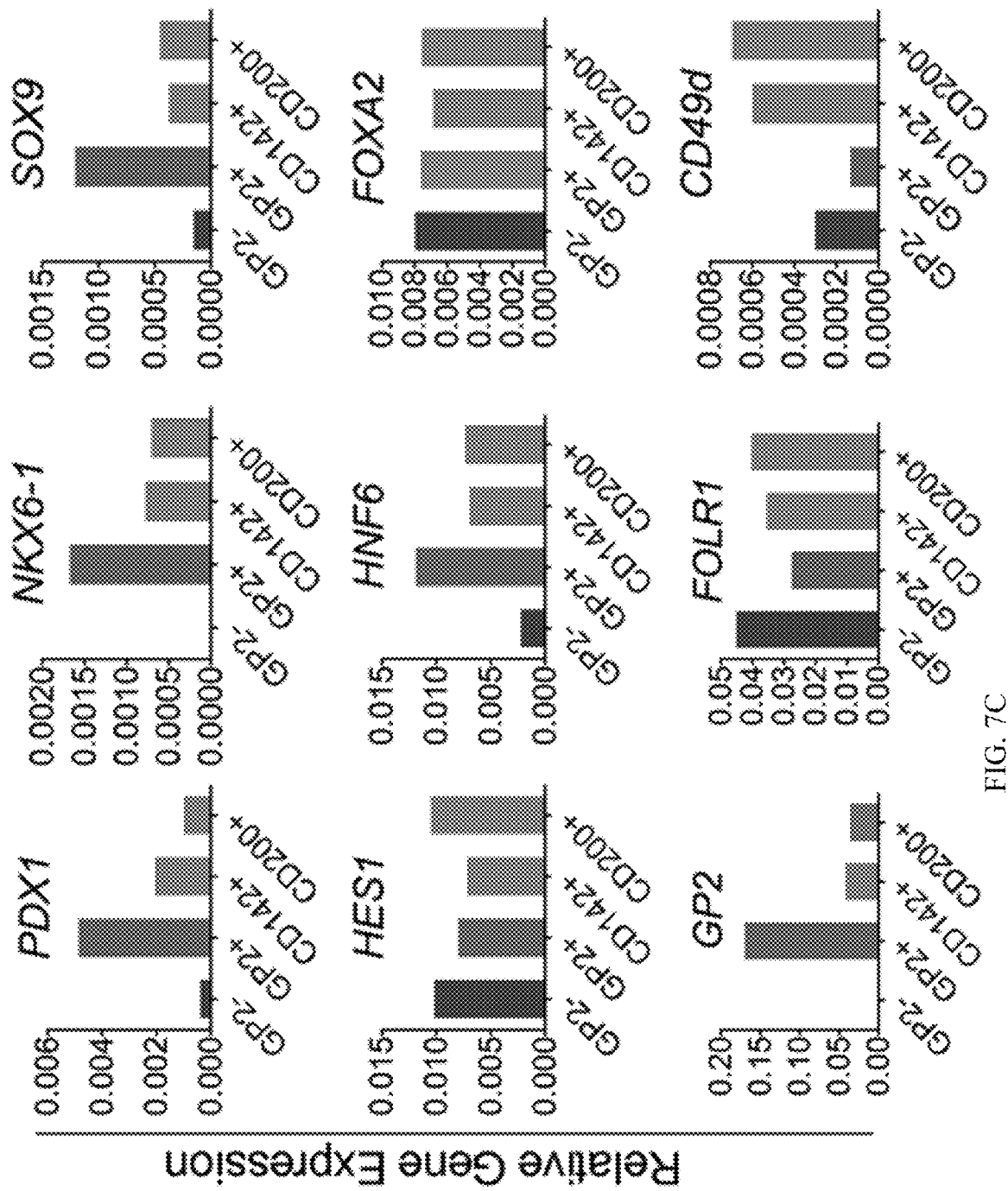

Example 9—Characterization of Currently Available Cell Surface Markers for Purification of Pancreatic Progenitor Cells Lastly, we examined the expression pattern of previously reported cell surface markers CD142, CD200 (Kelly et al., 2011) using the PDXeG reporter cell line cultured on MEFs and differentiated according to "protocol PE" (FIG. 7A). The majority of the GFP+ and GFP− cells are stained with CD142 and CD200, indicating that these surface markers do not faithfully mark the pancreatic progenitor population. By applying an independent and feeder free differentiation protocol published by Rezania et al. 2013 in combination with the genetically unmodified cell line HUES4, we assessed the specificity of our novel cell surface markers in parallel to the previously published CD142 and CD200. These results clearly show that GP2 is superior in labeling PDX1+/NKX6-1+ PPCs (FIGS. 7B and 7C).

Flow cytometric analysis of the previously identified cell surface markers CD142 and CD200 in the PDXeG reporter cell line cultured on MEFs (FIG. 7A) showed that the majority of the GFP+ and GFP− cells are stained with CD142 and CD200. Hence these markers are not specific enough in recognizing the PDX1+/NKX6-1+ cells in a heterogeneous stem cell culture.

Collectively, these findings show that the novel cell surface markers GP2, Cd49d, and FOLR1 can be used to isolate hESC-derived pancreatic progenitor cells and that the previously published CD200 and CD142 are not as specific as GP2 or FOLR1 in recognizing pancreatic progenitor cells.

Figure 8A:
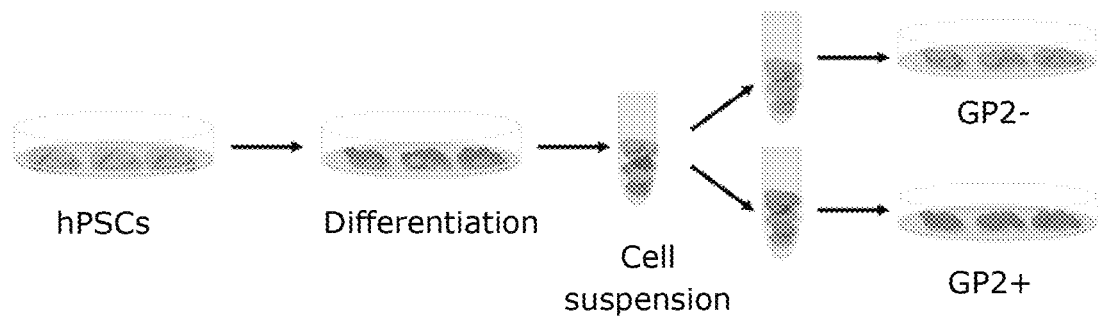
FIGS. 8A-8G. Differentiation of purified GP2+/CD49d− PPCs into glucose responsive insulin expressing cells.
Figure 8B:
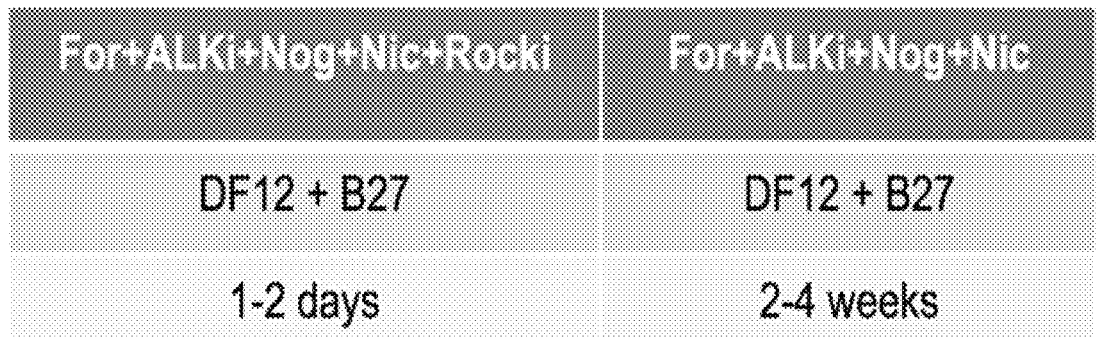
Figure 8C:
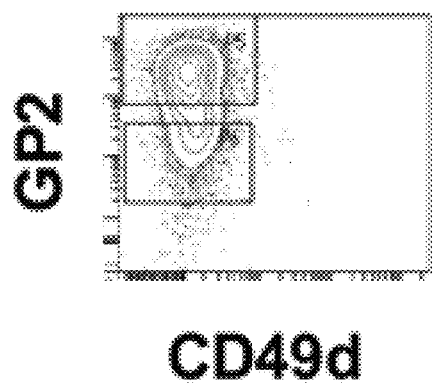
Figure 8D:
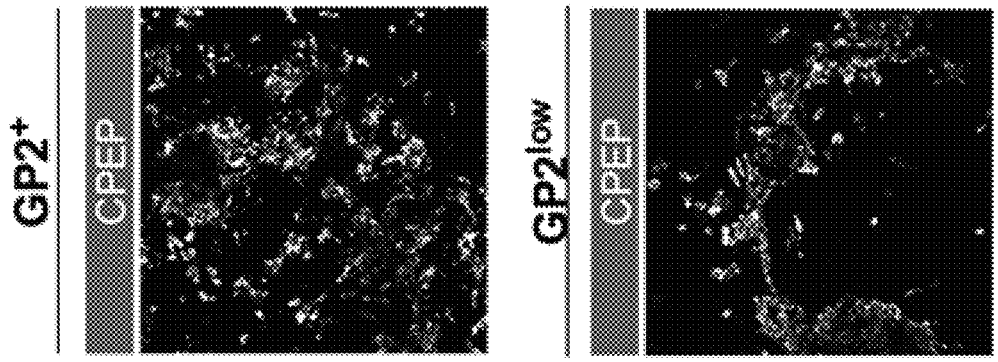

Example 10—Differentiation of Purified GP2+/CD49d− PPCs into Insulin Expressing Cells/Lineage Potential of Purified GP2+ hPPCs Towards the Beta Cell Lineage To show that the isolated GP2+/CD49d− pancreatic progenitor cells have the capacity to differentiate into insulin expressing cells, these cells were replated after FACS sorting (FIG. 8A). This replating experiment was performed using the genetically untagged cell line HUES4 (FIG. 8). Purified PPCs were replated on fibronectin-coated plates and differentiated further in the presence of Forskolin, ALKi, Noggin and Nicotinamide. During the initial 24-48 hours Rock inhibitor was also added to increase viability after the sorting (FIG. 8B). As extremely few CD49d+ cells appear in these cultures, GP2+ and the limited/few number of GP2 low expressing cells were sorted (FIG. 8C).

Figure 8E:
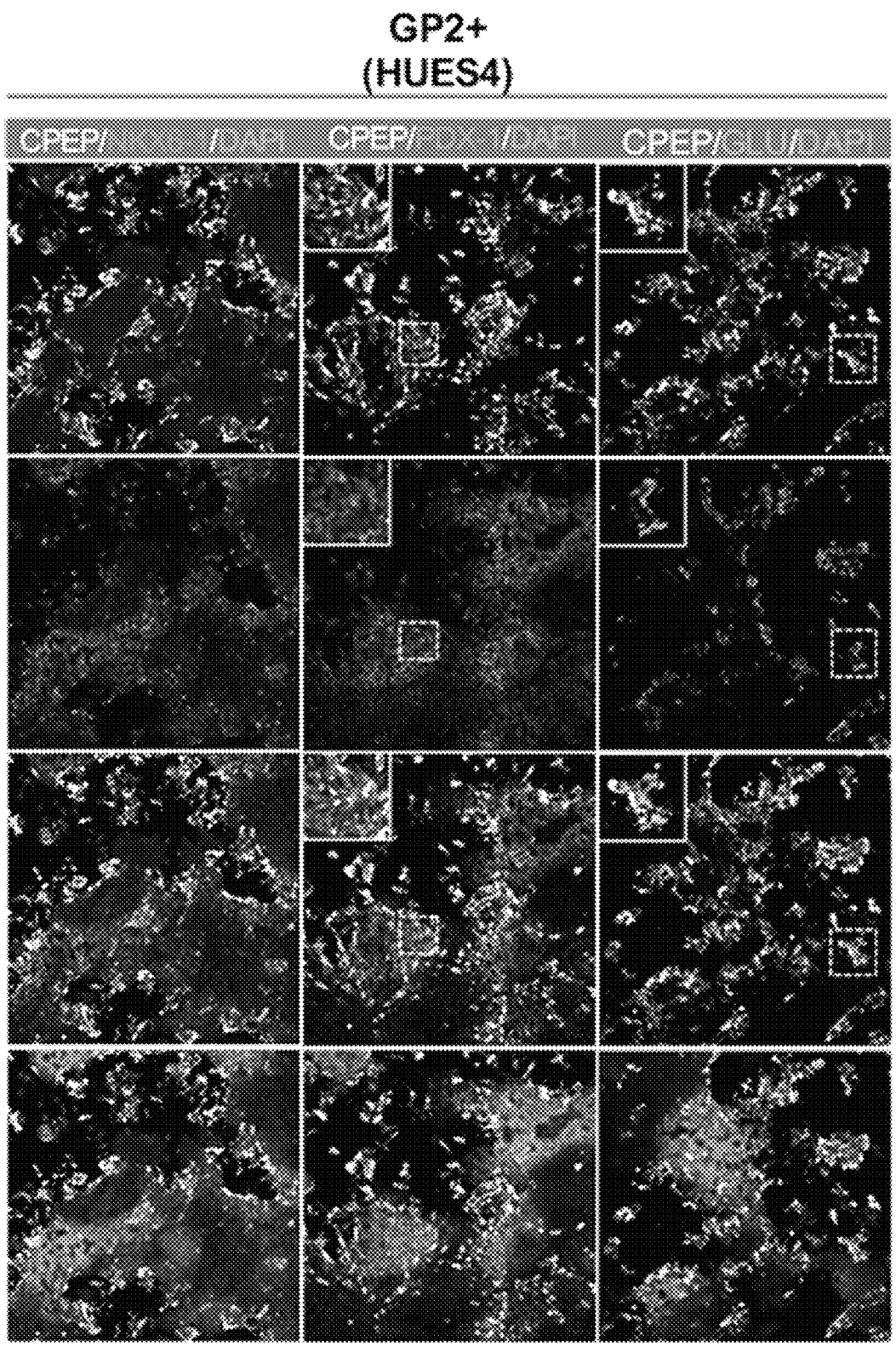
Figure 8F:
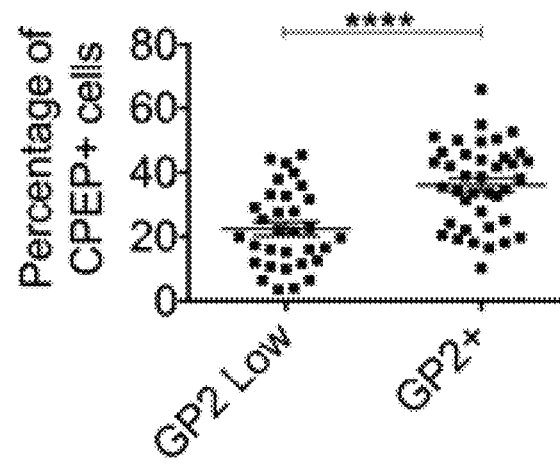
Figure 8G:
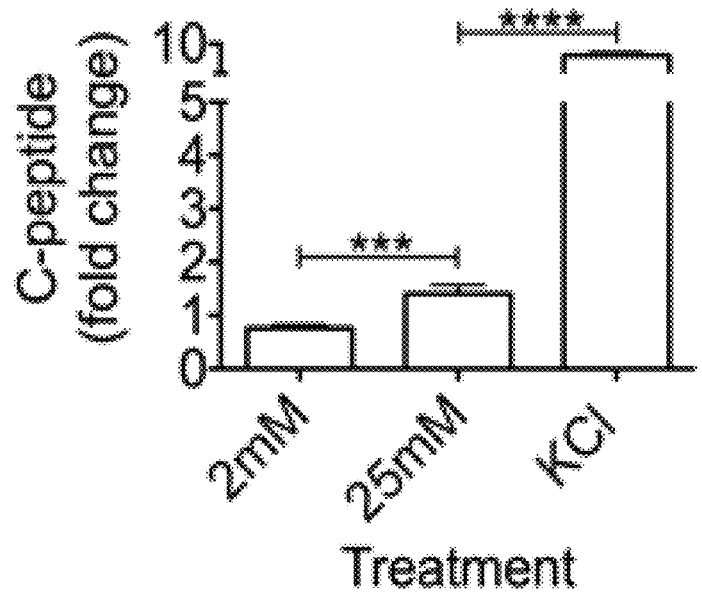

Differentiated GP2+(Cd49d−) cells showed significant enrichment of CPEP+ cells in comparison to the GP2$^{low}$ (CD49d−) cells (FIG. 8D), this was also confirmed by quantification of CPEP+ cells/DAPI area (FIG. 8F).

Immunofluorescence analysis of differentiated GP2+/CD49d− cells is shown in FIG. 8E. Finally, glucose stimulated insulin secretion analysis on the cells derived from the GP2+ PPCs confirmed that these cells are also glucose responsive (FIG. 5G). Thus, by using our modified protocol GP2+ PPCs can be differentiated to glucose responsive monohormonal C-peptide (CPEP)+ cells.

Example 11—CDKN1a Silencing Promotes Expansion of the GP2+ Human Pancreatic Progenitor Cells Among the genes that were enriched in the PDX1+/NKX6-1+ PPCs based on our microarray analysis we found several cell cycle specific genes, in particular CDKN1a and CDKN2a. To investigate whether these genes were important targets (involved) in the cell cycle machinery regulating the expansion of the pancreatic progenitors we performed siRNA-mediated knockdown of the chosen targets in the pancreatic progenitor cells from different time points. Indeed, knockdown of CDKN1a (FIG. 9B) in early pancreatic progenitor cells significantly elevated (>60% increase was observed, data not shown) the number of proliferating pancreatic progenitor cells in the G2/M phase (FIGS. 9C-E). This proliferative effect was absent if CDKN1a knockdown was performed in mature GP2+ pancreatic progenitors (FIGS. 9F-H). As expected, immunofluorescence staining with Ki67, confirmed notable increase of Ki67+ cells in the early pancreatic progenitors where CDKN1a was knocked down (FIG. 9I).

REFERENCES

Ameri J et al. (2010) Stem Cells 28(1):45-56
Aoi, T. et al. (2008) Nihon Rinsho. 66(5):850-6
Chung et al. (2008) Cell Stem Cell. 2(2):113-7.
D'Amour, K. A. et al. (2006) Nat Biotechnol. (11):1392-401.
Heins et. al. (2004) Stem Cells. 22(3):367-76.
Holland et al. (2006) Genesis 44(6):304-307
Jiang, J. et al. (2007), Stem Cells 25
Jiang, J. et al. (2011) Stem Cells. 29(4):609-17
Kelly et al. (2011) Nat Biotechnol. (29): 750-756.
Kroon, E. et al. (2008) Nat Biotechnol. 26(4):443-52.
Naujok and Lenzen (2012) Stem Cell Rev. 8(3):779-91.
Pagliuca et al. (2014) Cell. 159(2):428-39
Rezania et al. (2010) Eur J Pharmacol. 627(1-3):265-8
Rezania et al. (2012) Diabetes. 2012 August; 61(8):2016-29.
Rezania et al. (2013) Stem Cells 31(11):2432-42
Rezania et al. (2014) Nat Biotechnol. (32):1121-33.
Shapiro et al. (2000) N Engl J Med 343:230-238
Shapiro et al. (2001a) Best Pract Res Clin Endocrinol Metab 15:241-264
Shapiro et al. (2001b) British Medical Journal 322:861
Stadtfeld and Hochedlinger (2010) Genes Dev. 24(20):2239-63
Takahashi and Yamanaka (2006) Cell. 2006 Aug. 25; 126 (4):663-76
Takahashi et al. (2007) Cell 131 (5):861
Takashima et al. (2014) Cell. 158(6): 1254-1269
Tesar et al. (2007) Nature 448(7150):196-9
Thomson, A. et al. (1998) Science. 6; 282(5391):1145-7.
Wernig, M. et al. (2007) Nature. 448(7151):318-24
Yu et al., (2007) Science 318:5858
Yu J, et al. (2009) Science vol 324

Items

1. A method for isolating a population enriched for bona fide pancreatic progenitor cell, said method comprising the steps of:
   i) providing a cell population comprising at least one bona fide pancreatic progenitor cell, wherein the bona fide pancreatic progenitor cell expresses PDX1 and NKX6-1; and
   ii) exposing said cell population to:
      a) a first ligand which binds to a first marker specific for PDX1− cells and selecting the cells that do not bind to said first ligand from said cell population, thereby enriching the cell population for PDX1+ cells; and/or
      b) a second ligand which binds to a second marker specific for PDX1+ cells and selecting the cells that bind to said second ligand from the cells that do not bind to said second ligand, thereby enriching the cell population for PDX1+ cells; and/or
      c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells;
   thereby obtaining a cell population enriched for bona fide pancreatic progenitor cells.
2. The method according to item 1, wherein at least one of the first, second and third ligands is an antibody or fragment thereof.
3. The method according to any one of the preceding items, wherein the antibody is a monoclonal or polyclonal antibody.
4. The method according to any one of the preceding items, wherein at least one of the first, second and third ligands binds to a cell surface marker of the bona fide pancreatic progenitor cell.
5. The method according to any one of the preceding items, wherein at least one of the first, second and third ligands is conjugated to a label.
6. The method according to any one of the preceding items, wherein the expression of at least one of the first, second and third marker is detected by flow cytometry.
7. The method according to any one of the preceding items, wherein the cells are removed or selected by flow cytometry.

8. The method according to any one of the preceding items, wherein the first ligand is an antibody or fragment thereof directed against CD49d.
9. The method according to any one of the preceding items, wherein the second ligand is an antibody or fragment thereof directed against a target selected from the group consisting of: FOLR1, CDH1/ECAD, F3/CD142, PDX1, FOXA2, EPCAM, HES1 and GATA4.
10. The method according to any one of the preceding items, wherein the second ligand is an antibody or fragment thereof directed against FOLR1.
11. The method according to any one of the preceding items, wherein the third ligand is an antibody or fragment thereof directed against a target selected from the group consisting of: GP2, SCN9A, MPZ, NAALADL2, KCNIP1, CALB1, SOX9, NKX6-2 and NKX6-1.
12. The method according to any one of the preceding items, wherein the third ligand is an antibody or fragment thereof directed against GP2.
13. The method according to any one of the preceding items, wherein the first ligand is an antibody or fragment thereof directed against CD49d and the third ligand is an antibody directed against GP2.
14. The method according to any one of the preceding items, wherein the first ligand is an antibody or fragment thereof directed against CD49d, the second ligand is an antibody or fragment thereof directed against FOLR1 and the third ligand is an antibody or fragment thereof directed against GP2.
15. The method according to any one of the preceding items, wherein the bona fide pancreatic progenitor cells are derived from cells capable of differentiation such as human pluripotent stem cells.
16. The method according to any one of the preceding items, wherein the cells capable of differentiation are selected from the group consisting of human iPS cells (hIPSCs), human ES cells (hESCs) and naive human stem cells (NhSCs).
17. The method according to any one of the preceding items, wherein the cells capable of differentiation are derived from cells isolated from an individual.
18. The method according to any one of the preceding items, wherein at least one cell of the cell population enriched for bona fide pancreatic progenitor cells has the capability to differentiate further.
19. The method according to any one of the preceding items, wherein at least one cell of the cell population enriched for bona fide pancreatic progenitor cells has the capability to differentiate further into pancreatic hormone-producing cells.
20. The method according to any one of the preceding items, wherein at least one of the pancreatic hormone-producing cells is an insulin-producing cell and/or is responsive to glucose.
21. The method according to any one of the preceding items, wherein at least one cell of the cell population enriched for bona fide pancreatic progenitor cells can produce insulin-producing islet cells.
22. A method for producing a cell population enriched for bona fide pancreatic progenitor cells, said enriched cell population comprising at least 70% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells.
23. The method of item 22, said method comprising the steps of:
    i) providing a cell population comprising a bona fide pancreatic progenitor cell, wherein the bona fide pancreatic progenitor cell expresses PDX1 and NKX6-1; and
    ii) exposing said cell population to:
        a) a first ligand which binds to a first marker specific for PDX1− cells and selecting the cells that do not bind to said first ligand from said cell population, thereby enriching the cell population for PDX1+ cells;
        and/or
        b) a second ligand which binds to a second marker specific for PDX1+ cells and selecting the cells that bind to said second ligand from the cells that do not bind to said second ligand, thereby enriching the cell population for PDX1+ cells;
        and/or
        c) a third ligand which binds to a third marker specific for PDX1+ NKX6-1+ cells and selecting the cells that bind to said third ligand from the cells that do not bind to said third ligand, thereby enriching the cell population for PDX1+ NKX6-1+ cells.
24. The method of item 22 or 23, wherein the first ligand is an antibody or fragment thereof directed against CD49d, the second ligand is an antibody or fragment thereof directed against FOLR1 and the third ligand is an antibody or fragment thereof directed against GP2.
25. A cell population comprising at least 50% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells.
26. A cell population comprising bona fide pancreatic progenitor cells, obtainable by the method of any one of items 1 to 21.
27. The cell population according to item 26, wherein said cell population comprises at least 50% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells.
28. A cell population comprising bona fide pancreatic progenitor cells, obtainable by the method of any one of items 1 to 21 for treatment of a metabolic disorder in an individual in need thereof.
29. The cell population for treatment of a metabolic disorder in an individual in need thereof according to item 28, wherein said cell population comprises at least 50% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells.
30. A cell population enriched for bona fide pancreatic progenitor cells according to any one of items 25 to 29 for treatment of a metabolic disorder in an individual in need thereof
31. The cell population of item 30, wherein the metabolic disorder is diabetes mellitus, such as insulin-dependent diabetes mellitus, non-insulin-dependent diabetes mellitus, malnutrition-related diabetes mellitus, type 1 diabetes, type 2 diabetes or unspecified diabetes mellitus.

32. A method of treatment of a metabolic disorder in an individual in need thereof, wherein the method comprises a step of providing a cell population according to any one of items 25 to 29.

33. The method according to item 32, said method further comprising a step of transplanting at least part of said cell population into said individual.

34. The method according to any one of items 32 to 33, said method further comprising a step of inducing differentiation of at least part of cell population into insulin-producing cells and optionally a step of isolating said insulin-producing cells.

35. The method according to any one of items 32 to 34, wherein the step of inducing differentiation of at least part of cell population into insulin-producing β-cells comprises the step of incubating at least part of said cell population in the presence of a Yap1 inhibitor, thereby obtaining a cell population enriched for insulin-producing β-cells.

36. The method according to item 35, wherein the Yap1 inhibitor is verteporfin.

37. The method according to any of items 32 to 36, wherein the insulin-producing β-cells have increased expression of at least one of Insm-1, Isl-1, MafA and MafB compared to cells that have been incubated in the absence of the Yap1 inhibitor.

38. The method according to any one of items 32 to 37, wherein the insulin-producing β-cells have increased insulin area compared to the insulin area in cells obtained when the cell population is incubated in the absence of Yap1 inhibitor.

39. The method according to any one of items 32 to 36, said method further comprising a step of transplanting said insulin-producing cells into said individual.

The invention claimed is:

1. A method for isolating a cell population enriched for bona fide pancreatic progenitor cells, the method comprising:
   i) providing a cell population comprising at least one bona fide pancreatic progenitor cell, wherein the bona fide pancreatic progenitor cell expresses PDX1 and NKX6-1; and
   ii) exposing the cell population to a ligand which binds to a marker specific for PDX1+NKX6-1+ cells, wherein the marker is selected from SCN9A, NAALADL2, KCNIP1 and CALB1, and selecting the cells that bind to the ligand from the cells that do not bind to the ligand, thereby enriching the cell population for PDX1+NKX6-1+ cells;
   thereby obtaining a cell population enriched for bona fide pancreatic progenitor cells.

2. The method according to claim 1, wherein the ligand is an antibody or fragment thereof.

3. The method according to claim 2, wherein the ligand is an antibody or fragment thereof directed against SCN9A, NAALADL2, KCNIP1 or CALB1.

4. The method according to claim 3, further comprising exposing the cell population to an antibody or fragment thereof directed against CD49d and selecting the cells that do not bind to the antibody or fragment thereof directed against CD49d from the cells that do bind the antibody or fragment thereof directed against CD49d prior to exposing the cell population to an antibody directed against SCN9A, NAALADL2, KCNIP1 or CALB1.

5. The method according to claim 1, wherein the cells are removed or selected by flow cytometry.

6. The method according to claim 1, wherein the bona fide pancreatic progenitor cells are derived from cells capable of differentiation selected from human iPS cells (hIPSCs), human ES cells (hESCs) or naive human stem cells (NhSCs).

7. The method according to claim 6, wherein the cells capable of differentiation are derived from cells isolated from an individual.

8. The method according to claim 1, wherein at least one cell of the cell population enriched for bona fide pancreatic progenitor cells has the capability to differentiate further into pancreatic hormone-producing cells.

9. The method according to claim 1, wherein CDKN1a or CDKN2a is inactivated in the cell population provided in i).

10. The method according to claim 9, wherein CDKN1a and/or CDKN2a is inactivated by knock-down, deletion, silencing or repression.

11. The method according to claim 1, wherein the starting cell population is a pancreatic progenitor population expressing PDX1.

12. The method according to claim 11, wherein inactivation of CDKN1a and/or CDKN2a results in an increase in the proportion of cells entering replicating stage compared to the proportion of cells entering replicating stage when CDKN1a and/or CDKN2a is not inactivated.

13. The method according to claim 12, wherein the increase is at least 1.5-fold.

14. A method for producing a cell population enriched for bona fide pancreatic progenitor cells, the enriched cell population comprising at least 70% bona fide pancreatic progenitor cells, the method according to claim 1.

15. A method of treatment of a metabolic disorder in an individual in need thereof, wherein the method comprises:
   a) providing a cell population enriched for bona fide pancreatic progenitor cells according to the method of claim 1;
   b) transplanting at least part of the cell population into the individual;
   and/or
   c) inducing differentiation of at least part of the cell population into insulin-producing cells, isolating the insulin-producing cells, and transplanting at least part of the insulin producing cells into the individual;
   thereby treating the metabolic disorder.

16. A cell population comprising at least 50% bona fide pancreatic progenitor cells, such as at least 75% bona fide pancreatic progenitor cells, such as at least 80% bona fide pancreatic progenitor cells, such as at least 85% bona fide pancreatic progenitor cells, such as at least 90% bona fide pancreatic progenitor cells, wherein at least 34% of the cells of the cell population express GP2.

17. The cell population according to claim 16, wherein at the most 2% of the cells of the cell population express CD49d.

18. A method for treatment of a metabolic disorder in an individual in need thereof, wherein the method comprises:
   a) providing the cell population of claim 16, and
   b) transplanting at least part of the cell population into the individual,
   thereby treating the metabolic disorder.

* * * * *